(12) United States Patent
Mandelis et al.

(10) Patent No.: US 9,131,170 B2
(45) Date of Patent: Sep. 8, 2015

(54) METHOD AND APPARATUS FOR PERFORMING HETERODYNE LOCK-IN IMAGING AND QUANTITATIVE NON-CONTACT MEASUREMENTS OF ELECTRICAL PROPERTIES

(71) Applicants: Andreas Mandelis, Scarborough (CA); Alexander Melnikov, Mississauga (CA)

(72) Inventors: Andreas Mandelis, Scarborough (CA); Alexander Melnikov, Mississauga (CA)

( * ) Notice: Subject to any disclaimer, the term of this patent is extended or adjusted under 35 U.S.C. 154(b) by 272 days.

(21) Appl. No.: 13/827,110

(22) Filed: Mar. 14, 2013

(65) Prior Publication Data

US 2013/0278749 A1    Oct. 24, 2013

Related U.S. Application Data

(60) Provisional application No. 61/623,676, filed on Apr. 13, 2012.

(51) Int. Cl.
 *H04N 5/33* (2006.01)
 *G01N 21/64* (2006.01)
 *G01N 21/95* (2006.01)

(52) U.S. Cl.
 CPC ............ *H04N 5/33* (2013.01); *G01N 21/6489* (2013.01); *G01N 21/9501* (2013.01)

(58) Field of Classification Search
 CPC .. H04N 5/33; G01N 21/9501; G01N 21/6489
 USPC ............ 348/86, 87; 250/338.1, 341.1, 341.4, 250/341.5, 341.7, 341.8
 See application file for complete search history.

(56) References Cited

U.S. PATENT DOCUMENTS

| | | |
|---|---|---|
| 4,950,897 A | 8/1990 | Mandelis et al. |
| 5,667,300 A | 9/1997 | Mandelis et al. |
| 6,584,341 B1 | 6/2003 | Mandelis et al. |
| 7,045,786 B2 * | 5/2006 | Mandelis et al. .......... 250/341.1 |

(Continued)

OTHER PUBLICATIONS

Melnikov et al. "Infrared lock-in carrierography (photocarrier) radiometric imaging) of Si solar cells". JAP 107, 114513. Dec. 2010, pp. 1-11.*

(Continued)

*Primary Examiner* — Christopher S Kelley
*Assistant Examiner* — Zhihan Zhou
(74) *Attorney, Agent, or Firm* — Lynn C. Schumacher; Stephen W. Leonard; Hill & Schumacher

(57) ABSTRACT

Methods are provided for producing optical carrierographic images of a semiconductor sample. Focused and spatially overlapped optical beams excite carriers across within the semiconductor sample, where the optical beams are modulated such that a beat frequency is substantially less than either modulation frequency. An infrared detector detects infrared radiation emitted from the semiconductor sample in response to absorption of the optical beams, thereby obtaining a plurality of carrierographic signals at different points in time during at least one beat period, which are processed with a lock-in amplifier, with a reference signal at the beat frequency, to obtain an amplitude signal and a phase signal. Carrierographic lock-in images of the sample are obtained in a scanning configuration, or in an imaging format using an imaging detector. The images carry quantitative information about recombination lifetimes in substrate Si wafers and electrical parameters in solar cells, namely photogeneration current density, diode saturation current density, ideality factor, and maximum power photovoltage.

40 Claims, 36 Drawing Sheets

(56) References Cited

U.S. PATENT DOCUMENTS

| | | |
|---|---|---|
| 7,116,421 B2 | 10/2006 | Garcia et al. |
| 7,525,661 B2 | 4/2009 | Mandelis et al. |
| 7,729,734 B2 | 6/2010 | Mandelis et al. |
| 8,306,608 B2 | 11/2012 | Mandelis et al. |
| 2002/0011852 A1 | 1/2002 | Mandelis et al. |
| 2011/0118571 A1 | 5/2011 | Mandelis et al. |
| 2013/0102865 A1 | 4/2013 | Mandelis et al. |

OTHER PUBLICATIONS

P. Würfel, T. Trupke, T. Puzzer, E. Schäffer, W. Warta, S. W. Glunz, "Diffusion lengths of silicon solar cells from luminescence images." J. Appl. Phys. 101, 123110 (2007).

J. A. Gisecke, M. Kasemann, W. Warta. Determination of local minority carrier diffusion lengths in crystalline silicon from luminescence images. J. Appl. Phys. 106, 014907 (2009).

D. Guidotti, J. S. Batchelder, J. A. Van Vechten, and A. Finkel. Nondestructive depth profiling of carrier lifetimes in full silicon wafers. Appl. Phys. Lett. 48, 68 (1986).

S. Herlufsen, K. Ramspeck, D. Hinken, A. Schmidt, J. Müller, K. Bothe, J. Schmidt, and R. Brendel. Dynamic photoluminescence lifetime imaging for the characterisation of silicon wafers. Phys. Stat. Sol. RRL 1, (2010).

A. Mandelis, J. Batista and D. Shaughnessy. Infrared photocarrier radiometry of semiconductors: Physical principles, quantitative depth profilometry, and scanning imaging of deep subsurface electronic defects. Phys. Rev. B, 67 205208 (2003).

A. Melnikov, A. Mandelis, J. Tolev, P. Chen, and S. Huq. Infrared lock-in carrierography (photocarrier radiometric imaging) of Si Solar cells. J. Appl. Phys. 107, 114513 (2010).

T. Ikari T, A. Salnick and A. Mandelis. Theoretical and experimental aspects of three-dimensional infrared photothermal radiometry of semiconductors. J. Appl. Phys. 85, 7392 (1999).

S. Grauby, B. C. Forget, S. Hole and D. Fournier. High resolution photothermal imaging of high frequency phenomena using a visible charge coupled device camera associated with a multichannel lock-in scheme. Rev. Sci. Instrum. 70, 3603 (1999).

J. Tolev, A. Mandelis, and M. Pawlak. Nonlinear Dependence of Photocarrier Radiometry Signals from p-Si Wafers on Optical Excitation Intensity. J. Electrochem. Soc. 154, H938 (2007).

A. Mandelis. Coupled ac photocurrent and photothermal reflectance response theory of semiconducting p-n junctions. I J. Appl. Phys., 66, 5572 (1989).

T. Trupke, R. A. Bardos, M. C. Schubert and W. Warta. Photoluminescence imaging of silicon wafers. Appl. Phys. Lett. 89, 044107 (2006).

W. Shockley and H. J. Queisser. Detailed Balance Limit of Efficiency of p-n Junction Solar Cells. J. Appl. Phys. 32, 510 (1961).

A. Mandelis Laser Infrared Photothermal Radiometry of Semiconductors: Principles and Applications to Solid State Electronics. Solid-State Electron. 42, 1, pp. 1-15 (1998).

J. Isenberg and W. Warta. Spatially Resolved Evaluation of Power Losses in Industrial Solar Cells by Illuminated Lock-in Thermography. Progr. Photovoltaics: Research and Applications 12, pp. 339-353 (2004).

O. Breitenstein M. Langenkamp, O. Lang and A. Schirrmacher. Shunts due to laser scribing of solar cells evaluated by highly sensitive lock-in thermography. Solar Energy Mater. Solar Cells 65, 55-62 (2001).

M. Kasemann, M. C. Schubert, M. The, M. Köber, M. Hermle, and W. Warta. Comparison of luminescence imaging and illuminated lock-in thermography on silicon solar cells. Appl. Phys. Lett. 89, 224102 (2006).

J. Batista, A. Mandelis and D. Shaughnessy. Temperature dependence of carrier mobility in Si wafers measured by infrared photocarrier radiometry. Appl. Phys. Lett. 82, No. 23, 4077 (2003).

Absil, E. et al., Photothermal heterodyne holography of gold Nanoparticles, Opt. Exp. 18 (2), 780-786 (2010).

Grauby, S. et al., High resolution photothermal imaging of high frequency phenomena using a visible charge coupled device camera associated with a multichannel lock-in scheme, Rev. Sci. Instr. 70 (9), 3606-3608 (1999).

Grauby, S. et al., Quantitative thermal imaging with CCD array coupled to an heterodyne multichannel lock-in detection, Anal. Sci. 17, s67-s69 (2001).

Suck, S. Y. et al., Frequency-resolved temperature imaging of integrated circuits with full field heterodyne interferometry, Appl. Phys. Lett. 96, 121108 (2010).

* cited by examiner

METHOD AND APPARATUS FOR PERFORMING HETERODYNE LOCK-IN IMAGING AND QUANTITATIVE NON-CONTACT MEASUREMENTS OF ELECTRICAL PROPERTIES

CROSS-REFERENCE TO RELATED APPLICATION

This application claims priority to U.S. Provisional Application No. 61/623,676, titled "METHOD AND APPARATUS FOR PERFORMING HETERODYNE LOCK-IN CARRIEROGRAPHIC IMAGING" and filed on Apr. 13, 2012, the entire contents of which is incorporated herein by reference.

BACKGROUND

The present disclosure relates apparatus and methods of non-contact, optical, characterization of semiconductors and semiconductor devices. More particularly, the present disclosure relates to the optical characterization of solar cells.

The modern solar cell industry has moved toward GW-scale production, with quality control becoming a critical factor [15]. Conventionally, the I-V characteristics are obtained by attaching a resistive load or a power source to the irradiated solar cell to measure and evaluate its efficiency. This practice cannot meet the needs of mass production.

Non-destructive and non-contacting methods for optoelectronic diagnostics of solar cells at all stages of the fabrication process are in strong demand. Several such methodologies have been developed for analyzing the excess charge carrier lifetime of Si wafers in a short time, including Carrier Density Imaging (CDI) [16]. Microwave photoconductance decay (MW-PCD) is a "golden standard" method for imaging lifetimes, including short recombination lifetimes, but it is much more time-consuming [17].

Imaging techniques based on quasi-steady-state (DC) electroluminescence (EL) and photoluminescence (PL) are widely used for qualitative and quantitative characterization of silicon solar cells [1-3]. PL imaging (PLI) is a fast non-destructive and non-contacting camera based diagnostic method which has been used for detecting electronic and other defects associated with crystal imperfections and handling of solar cells [3, 18-20]. However, DC PL cannot monitor the optoelectronic carrier kinetics of surface and near-subsurface regions due to its depth-integrated character through the signal dependence on the DC carrier diffusion length [3].

Harmonic and square-wave modulated photoluminescence [4a,b] is generally a non-linear process of electron-hole band-to-band recombination at high photoexcitation densities, with signals quadratic in the excess photocarrier density. With Si substrates, modulated photoluminescence requires very high frequencies (100 kHz-10 MHz) to monitor fast (~2.9 μs) interband-gap decay times [4a], whereas camera-based dynamic photoluminescence imaging of solar cells is attainable at very low frequencies (~25 Hz) [4b].

PL is a radiative emission process which can be interfered with by broad spectral contributions, such as overlapping thermal emissions due to lattice absorption, non-radiative recombination and thermal photon emission (Planck radiation). Laser-induced infrared photocarrier radiometry (PCR) [5, 27] is a quantitative dynamic near-infrared (NIR) modulated PL, spectrally-gated to filter out the thermal infrared component of the radiative emission spectrum from de-exciting free photocarriers, which is governed by the Law of Detailed Balance on which the non-equilibrium kinetics of optoelectronic device operation is based [21].

The infrared spectral complement of PCR concerns Planck (blackbody) thermal emissions due to nonradiative carrier de-excitations and can be detected using photothermal radiometry (PTR), a modulated thermal-wave generation and detection method [22]. The imaging equivalent of PTR is lock-in thermography (LIT) which has also been used to investigate local power losses in solar cells [23-25]. PCR has proven to be an effective non-contact methodology for the measurement of transport properties in semiconductors [5,26].

Lock-in carrierography (LIC), the dynamic imaging extension of PCR, was recently introduced using a spread super-band-gap laser beam and a near-infrared (NIR) InGaAs camera [6]. However, in implementing this technique, only low modulation frequencies (≤10 Hz) could be used in order to maximize image signal-to-noise ratio (SNR) through oversampling.

There remains a need for improved spatial (radial and axial) resolution characteristic of optoelectronic defects at frequencies much higher than those achievable by today's state-of-the-art InGaAs camera capabilities.

SUMMARY

Methods are provided for producing optical carrierographic images of a semiconductor sample. Focused and spatially overlapped optical beams excite carriers across within the semiconductor sample, where the optical beams are modulated such that a beat frequency is substantially less than either modulation frequency. An infrared detector detects infrared radiation emitted from the semiconductor sample in response to absorption of the optical beams, thereby obtaining a plurality of carrierographic signals at different points in time during at least one beat period, which are processed with a lock-in amplifier, with a reference signal at the beat frequency, to obtain an amplitude signal and a phase signal. Carrierographic lock-in images of the sample are obtained in a scanning configuration, or in an imaging format using an imaging detector.

Accordingly, in one aspect, there is provided a method of producing an optical carrierographic image of a semiconductor sample, the method comprising:

a) generating a first modulation signal having a first modulation frequency and a second modulation signal having a second modulation frequency, wherein a beat frequency between the first modulation frequency and the second modulation frequency is substantially less than both the first modulation frequency and the second modulation frequency;

b) generating a reference signal having a reference frequency equal to the beat frequency;

c) providing a first optical beam and a second optical beam, the first optical beam and the second optical beam having wavelengths selected for excitation of carriers within the semiconductor sample;

d) focusing and spatially overlapping the first optical beam and the second optical beam onto a location of the semiconductor sample;

e) modulating the first optical beam according to the first modulation signal and modulating the second optical beam according to the second modulation signal;

f) detecting, with an infrared detector, infrared radiation emitted from the semiconductor sample in response to absorption of the first optical beam and the second optical beam, and obtaining a plurality of carrierographic signals at different points in time during at least one beat period; and g) providing the reference signal to a lock-in amplifier and processing the carrierographic signals with the lock-in amplifier to obtain an amplitude signal and a phase signal.

In another aspect, there is provided a method of measuring the effective lifetime of carriers in a semiconductor substrate using lock-in-carrierography, the method comprising:

measuring lock-in-carrierography images of the semiconductor substrate at a plurality of modulation frequencies, each lock-in-carrierography image comprising a plurality of lock-in-carrierography signals corresponding to different locations of the substrate;

fitting a frequency dependence of the lock-in-carrierography signals from the lock-in-carrierography images to a rate equation model having the effective lifetime as a parameter; and calculating the effective lifetime at a plurality of locations of the semiconductor substrate.

In another aspect, there is provided a method of optically measuring one or more electrical parameters of a solar cell using lock-in-carrierography, the method comprising:

determining a mathematical relationship between a lock-in-carrierographic signal and one or more electrical properties of the solar cell, the mathematical relationship involving a calibration factor relating the lock-in-carrierographic signal to an electrical model of the solar cell;

measuring a plurality of lock-in-carrierography images of the solar cell;

calculating average signals from the lock-in-carrierography images; and determining the one or more electrical parameters by fitting the mathematical relationship to the average signals.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 35(a)-(d) correspond to FIGS. 33(a)-(d), respectively; bin size=0.25.

FIGS. 38(a)-(d) correspond to FIGS. 34(a)-(d), respectively. Bin size=0.002.

DETAILED DESCRIPTION

Figure 1A:
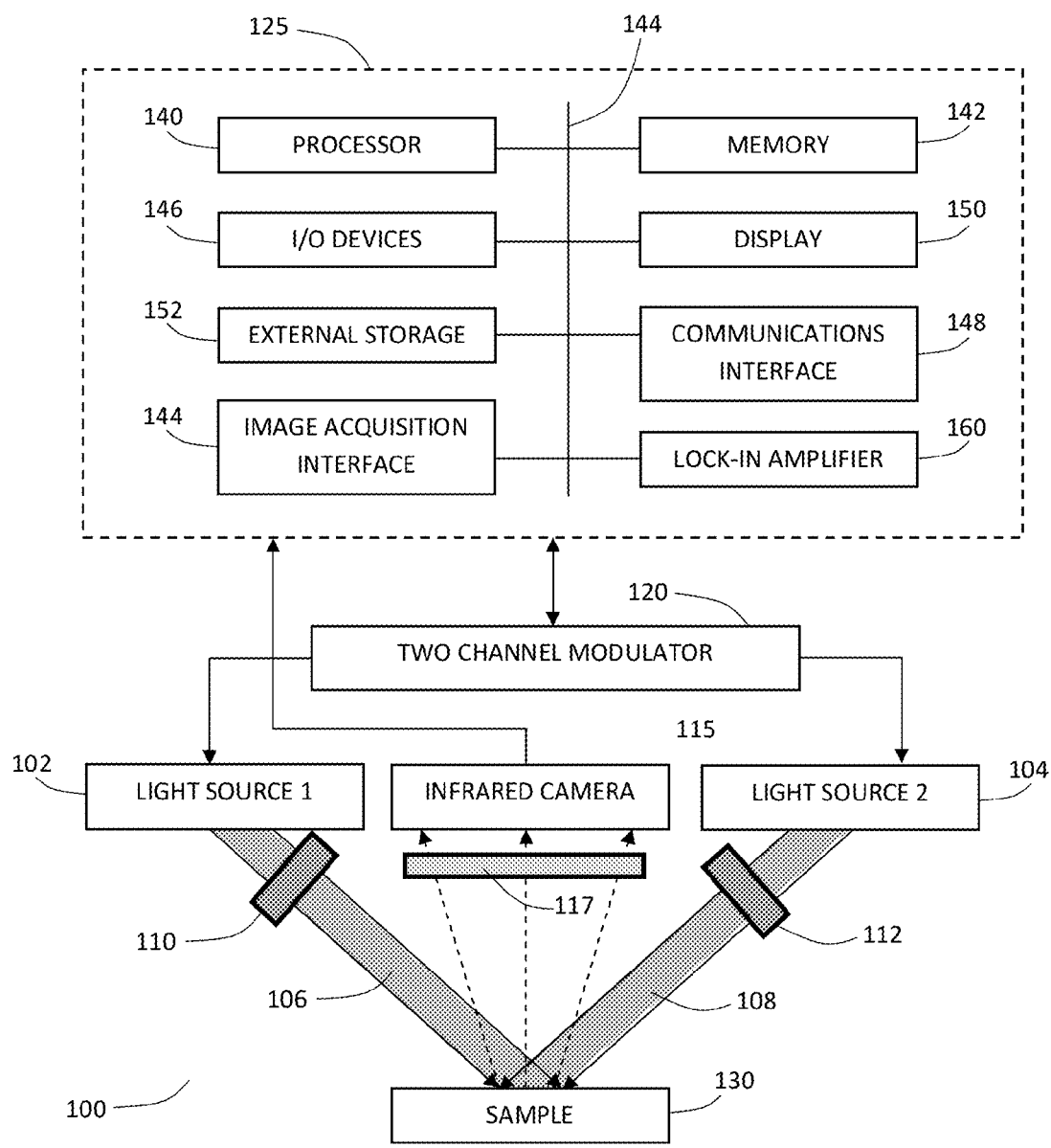
FIG. 1 provides (a) an illustration of an apparatus for heterodyne lock-in carrierographic imaging, (b) an example implementation of a heterodyne imaging carrierography apparatus, and (c) and example implementation of a scanning carrierography imaging apparatus.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

Embodiments of the present disclosure provide methods and apparatus for non-contact optical measurement of semiconductors and semiconductor devices using heterodyne lock-in carrierography, a photocarrier-density-wave imaging modality. As will be described below, the use of a heterodyne lock-in method enables the high-frequency (in the kHz range) carrierographic imaging with a spatial resolution exceeding that of known DC or sub kHz imaging methods.

The need for high-frequency imaging (for example, several kHz for silicon) can be understood in terms of the diffusive character of recombination which is controlled by the carrier AC diffusion length [6,7]

$$L_e(\omega) = \sqrt{\frac{D^*\tau}{1+i\omega\tau}} \quad (1)$$

where $D^*$ is the ambipolar carrier diffusivity and $\tau$ is the minority carrier recombination lifetime (~1 μs-10 ms). $L_e(\omega)$ is also a measure of the photo-excited carrier wavelength which decreases with increasing frequency and acts as the free carrier-density wave (CDW) probe of optoelectronic inhomogeneities and defect distributions across an area illuminated with superband-gap light, thus increasing spatial resolution commensurate with the value of the photo-carrier wavelength, $\lambda_{PC}=2\pi|L_e(\omega)|$.

The CDW is characterized by the strength of the carrierographic signal, which is determined by the linear or non-linear integral over the solar-cell thickness of the depth-dependent carrier density wave $\Delta N(z, \omega))$ [5,8]. This fact is expressed as Equation 21 below, which represents the thickness-averaged, but laterally spatially resolved, density of free photo-excited carriers which can recombine radiatively. The exponent $\gamma$ in Equation 21 is the degree of non-linearity of the recombination process, indicating the radiative recombination probability into valence and trap states. Unlike DC photoluminescence, the spatial resolution of carrierographic imaging depends on modulation frequency and its contrast arises from local variations in modulated CDW amplitude and phase related to the recombination lifetime r and other transport properties.

Two instrumental parameters of the NIR camera are the main limitations that have precluded high-frequency lock-in carrierographic imaging in the past: the exposure time and the period (or frame rate). The raster scan period limitation can be overcome by using undersampling (skipping one or more cycles while pacing over pre-determined fractions of a period through phase locking). For example, this method has been applied to lock-in thermography [9]. However, decreasing exposure time with increasing frequency leads to severe compromise of image quality due to the concomitant decrease in the number of recombination photons captured and thus in image signal-to-noise ratio (SNR) degradation.

Embodiments of the present disclosure overcome these limitations through the use of heterodyne imaging, enabling high-frequency CDW images consistent with carrierography requirements, but without stringent exposure time or frame rate limitations that have plagued past efforts.

In other embodiments, methods are provided for establishing relationships between surface-averaged distributions of optoelectronic energy conversion efficiencies and output photovoltages of entire Si solar cells, and radiative recombination modulated emission images. According to such embodiments, material and/or device properties, such as the solar efficiency and photovoltage, can be measured without the need for contacting electrodes.

In some embodiments disclosed herein, quantitative carrierography (CG) is employed and treated as a non-equilibrium excess photocarrier PL imaging technique, involving the treatment of radiative emission fluxes from semiconductors as representative of the non-equilibrium carrier densities that generated them in the sense of their Planck (blackbody) equivalent [8], also as expressed by the non-equilibrium physics of the generalized Planck law of radiation for non-black bodies [28].

Selected embodiments of the disclosure are now illustrated by way of example with reference to FIG. 1, which provides example apparatus 100 for performing lock-in carrierography. FIG. 1(a) schematically shows an example apparatus that includes two light sources 102 and 104 emitting beams 106 and 108, respectively, optional beam conditioning optics 110 and 112, imaging camera 115, a two-channel modulation source 120, and a control, data acquisition and processing unit 125.

In some embodiments, semiconductor sample 130 may be a solar cell, for example a crystalline or multicrystalline silicon solar cell.

Beams 106 and 108 are obtained from light sources 102 and 104 respectively, and are passed through optional beam conditioning elements 110 and 112 and subsequently spatially overlapped onto semiconductor sample 130. Light sources 102 and 104 have average wavelengths that span an electronic band gap of the semiconductor sample, such that the absorption of beams 106 and 108 by sample 130 leads to the optical excitation of electron-hole pairs within sample 130. Light sources 102 and 104 may have substantially equal wavelengths or average wavelengths. Although example embodiments of the present disclosure involve the use of lasers as light sources, it is to be understood that light sources need not be coherent sources of light.

Optional beam conditioning elements 110 and 112 may be provided to obtain a substantially homogeneous beam profile when beams 106 and 108 illuminate the surface of sample 130. Suitable beam conditioning elements include beam collimators and/or beam diffusers.

Imaging camera 115 is an infrared imaging camera configured to detect photoluminescence from semiconductor sample 130. As discussed further below, a suitable imaging camera is an InGaAs imaging camera. Imaging camera 115 is spectrally filtered by filter 117 in order to avoid the detection of scattered light from beams 106 and 108. The camera can also be fitted with additional filters to highlight or block imaging contrast of specific infrared emissions such as from oxygen precipitates in dislocations (spectrally gated carrierography).

Modulation source 120 is configured to directly or indirectly modulate the intensity of beams 106 and 108. In one example embodiment in which light sources 102 and 104 are current-driven sources such as a laser or a light emitting diode, each channel of modulation source may modulate the drive current of light sources 102 and 104, as shown. Alternatively, modulation source 102 may be configured to modulate the optical beams 106 and 108 emitted by light sources 102 and 104, respectively, for example, via external modulation devices such as optical choppers, acousto-optic or electro-optic modulators.

As shown in FIG. 1(a), in one embodiment, control, data acquisition and processing unit 125 may include an image acquisition interface (such as a frame grabber) 135, a processor 140, a memory 142, a system bus 144, one or more input/output devices 146, and a plurality of optional additional devices such as communications interface 148, display 150, and external storage 152. Control, data acquisition and processing unit 125 also includes a lock-in amplifier 160.

It is to be understood that the apparatus is not intended to be limited to the components shown in the Figure. For example, the apparatus may include one or more additional processors. Furthermore, it is to be understood that lock-in amplifier 160 may be provided as a hardware or software device. In one example implementation, in which lock-in amplifier 160 is provided in a software implementation, images may be captured at sub-period phases (such as 0-0 degrees, ¼-90 degrees, ½-180 degrees, ¾-270 degrees) and processed with a lock-in software scheme without the need of a separate hardware lock-in amplifier (such as hardware-based lock-in amplifiers that are only configured to process one signal at a time).

Using a lock-in amplifier (either hardware-based or software-based) provides the added ability to perform wide photocarrier radiometric (PCR) frequency scans at particular locations by focusing one of the laser beams and employing a single element detector (such as a single element InGaAs detector) in the scheme of FIG. 1(*a*) (for example, as shown in FIG. 1(*c*)). Such a PCR embodiment may yield quantitative recombination lifetime and surface recombination velocity measurements which can be used to calibrate carrierographic images in effective lifetime values. These transport parameters may by extracted from PCR frequency scans [5,13,14]. The latter include well-known formulas described in Ref. [5] involving bulk lifetime and surface recombination velocity combinations.

One or more components of control, acquisition, and processing unit 125 may be provided as an external component that is interfaced to a processing device. For example, frame grabber 135 may be an external frame grabber or may reside on a card directly interfaced with a computing device. In another example embodiment, lock-in amplifier 160 may be an external lock-in amplifier that is connected to processor 140.

Lock-in amplifier 160 is configured for processing image data obtained from image acquisition interface 135 based on a reference signal provided by modulation source 120. Accordingly, image data is decoded by control and processing unit 125 into both amplitude and phase images. Additionally, modulation source 120 is synchronized with the acquisition of images from imaging camera 115, such that a given number of image frames may be obtained per modulation period for processing by the lock-in amplifier. In selected embodiments described below, image frames may be collected by undersampling or oversampling.

Embodiments of the disclosure can be implemented via processor 140 and/or memory 142. For example, the functionalities described below can be partially implemented via hardware logic in processor 140 and partially using the instructions stored in memory 142. Some embodiments are implemented using processor 140 without additional instructions stored in memory 142. Some embodiments are implemented using the instructions stored in memory 142 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

Direct Lock-in Carrierography

Although the apparatus of FIG. 1 is configured for heterodyne lock-in carrierography, the apparatus may also be employed to perform direct lock-in carrierography. The present section considers the embodiment of direct lock-in carrierography and its limitations, before heterodyne lock-in carrierography is addressed in the following section. To perform direct lock-in carrierography, only one light source is employed, or both light sources 102 and 104 are provided with a common average wavelength and are modulated with a common modulation signal (e.g. a two-channel generator produces the same waveform for current modulation of both light sources). Infrared radiation is detected from semiconductor sample 130 using imaging camera 125, and amplitude and phase images are obtained by lock-in synchronously acquired image frames.

Figure 2:
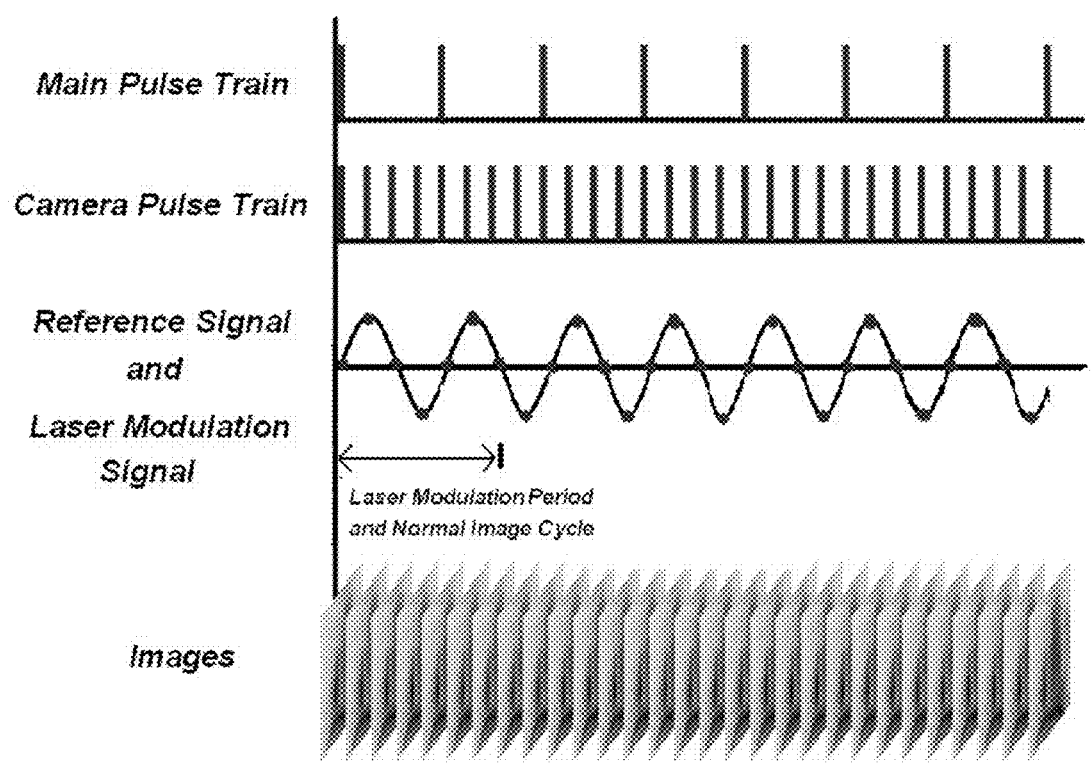
FIG. 2 illustrates a method of generating images at 10 Hz with twofold oversampling.

When performing full-frame direct lock-in imaging, the maximum modulation frequency for the light source is determined by the full-frame rate of the imaging camera. In one embodiment, this upper limit is imposed by the maximum full-frame rate of the imaging camera so as to allow for oversampling (such as fourfold oversampling) images collected at each modulation period [6]. Oversampling enables a high SNR construction and storage of lock-in in-phase (IP) and quadrature (O) images above the conventional twofold oversampling rate used in lock-in thermography with computer-generated amplitude and phase images derived from the IP and Q images [6]. FIG. 2 shows a conventional method of generating lock-in images at 10 Hz via twofold oversampling.

As shown in the Figure, with twofold oversampling, images are generated at phases of 0, $\pi/2$, $\pi$, and $3\pi/2$ of each modulation cycle. Once generated, the images are run through a computerized low-band pass filter to demodulate the carrierographic response and amplitude and phase images are derived. With fourfold oversampling, contrast of the IP and Q images is enhanced.

Figure 3:
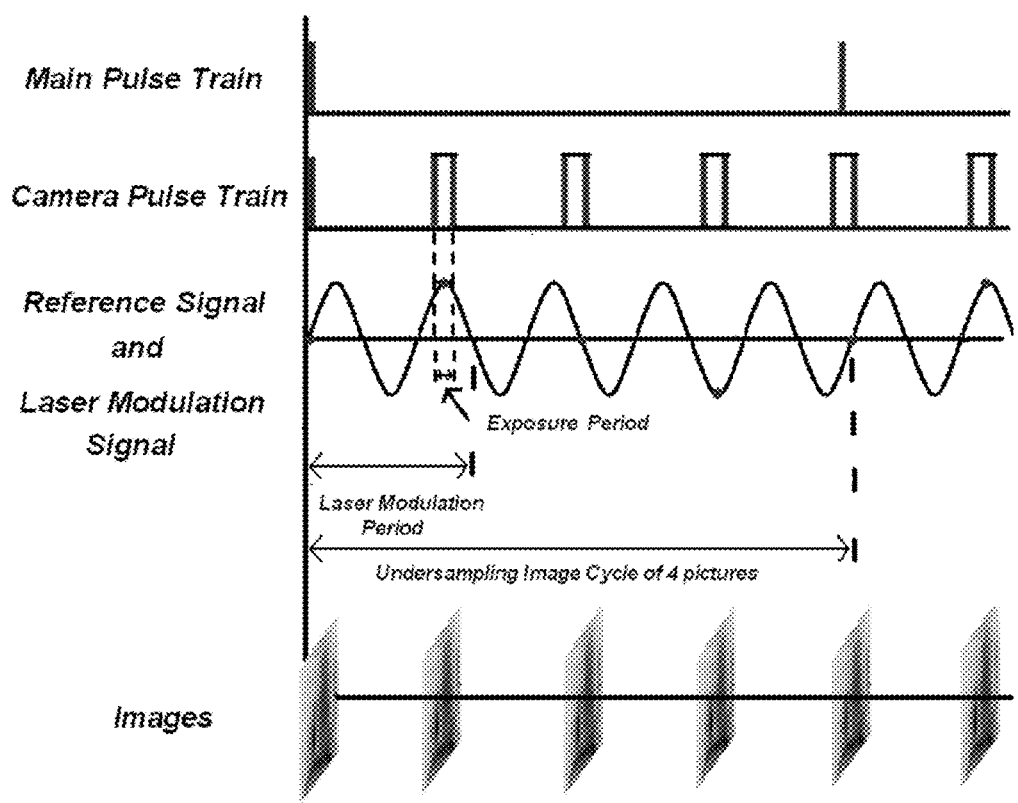
FIG. 3 illustrates the undersampling method of generating images by skipping modulation cycles.

However, at full-frame, the maximum frame rate of a typical InGaAs camera is approximately 10 Hz, which is problematic, since many of the features of shallow junction devices like solar cells can only be observed with modulation frequencies on the order of kHz. Although these frequencies can be attained by windowing the full frame to a smaller frame of 16×16 pixels, this leads to long image acquisition times of the full surface area, or poor resolution results, or degraded signal quality due to small exposure time, and maximum frame rate around 3 kHz for imaging a small fraction of the surface at high spatial resolution. Alternatively, an undersampling method for generating images can be introduced as shown in FIG. 3.

The undersampling method takes the same 4 images at 0, $\pi/2$, $\pi$, and $3\pi/2$ phases, but skips one or more cycles in between each image. FIG. 3 depicts an example showing undersampling in which one cycle is skipped for each image. By skipping more cycles, higher modulation frequencies can be achieved while keeping the camera frame rate low. Therefore, frequencies of the order of 1 kHz can be achieved with full-frame 320×256 pixels that provide high-resolution amplitude and phase images.

Unfortunately, as higher modulation frequencies are reached, problems arise with the undersampling method, which reduce the fidelity of the processed images. These problems include the multiplicative nature of small timing errors and the decreasing resolution with exposure time. It is noted that for error minimization, two cycles of images are taken, so the first cycle can be compared to the second. One cycle of images can be defined as iteration cycle. The correlation cycle, that is, the lock-in image processing cycle, consists of two iteration cycles in this case. The repetition of image acquisition is very important as it reinitializes the acquisition to the initial phase of 0 every other cycle. In this manner, the amplified error does not build up.

Exposure period is the time allowed for the carrierographic response to be viewed by the recording medium. As seen in FIG. 3, the exposure period decreases as the modulation frequency increases, since it is proportional to the period of the modulation signal. So, at high frequencies, the integration time is extremely small and the numbers of photons generating the camera signal is also very small.

Figure 4:
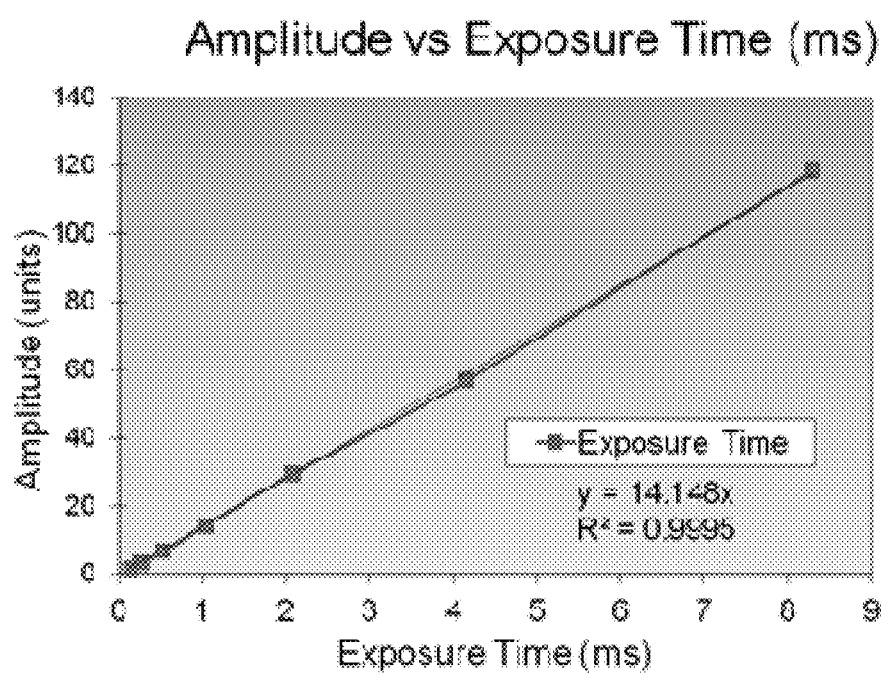
FIG. 4 plots the experimental dependence of camera signal amplitude on camera exposure time.

FIG. 4 illustrates how there is a linear relationship between the exposure time and the amplitude because the number of photons captured per unit exposure time is fairly constant. However, as the exposure time decreases, the quality of the picture decreases drastically. This is because at very high frequencies, the amplitude will be extremely small.

Therefore, attempts to increase the frequency of direct lock-in carrierographic image detection are hindered by poor spatial resolution when reducing the pixel count, and by poor signal-to-noise ratio when employing undersampling.

Heterodyne Lock-in Carrierography

The aforementioned problems can be overcome by employing heterodyne carrierography. Referring again to FIG. 1(a), an example heterodyne apparatus is realized by configuring two channel modulation source 120 to modulate light source 102 and light source 104 (or beams 106 and 108) with different frequencies.

Unlike the direct lock-in carrierography embodiment described above, the reference signal of the present heterodyne embodiment is not one of the modulation signals. Instead, the reference signal involves the beat frequency between the two modulation signals, and may be provided as a signal having a frequency equal to the difference in frequencies of the two modulation signals (or as the sum of the two signals). The reference signal may be generated externally by an additional one-channel modulation source (not shown) that is connected to control, acquisition and processing unit 125 and/or two channel modulation source 120 to enable synchronization. Alternatively, the reference signal, and optionally the two modulation signals, may be generated by control, acquisition and processing unit 125.

Figure 5:
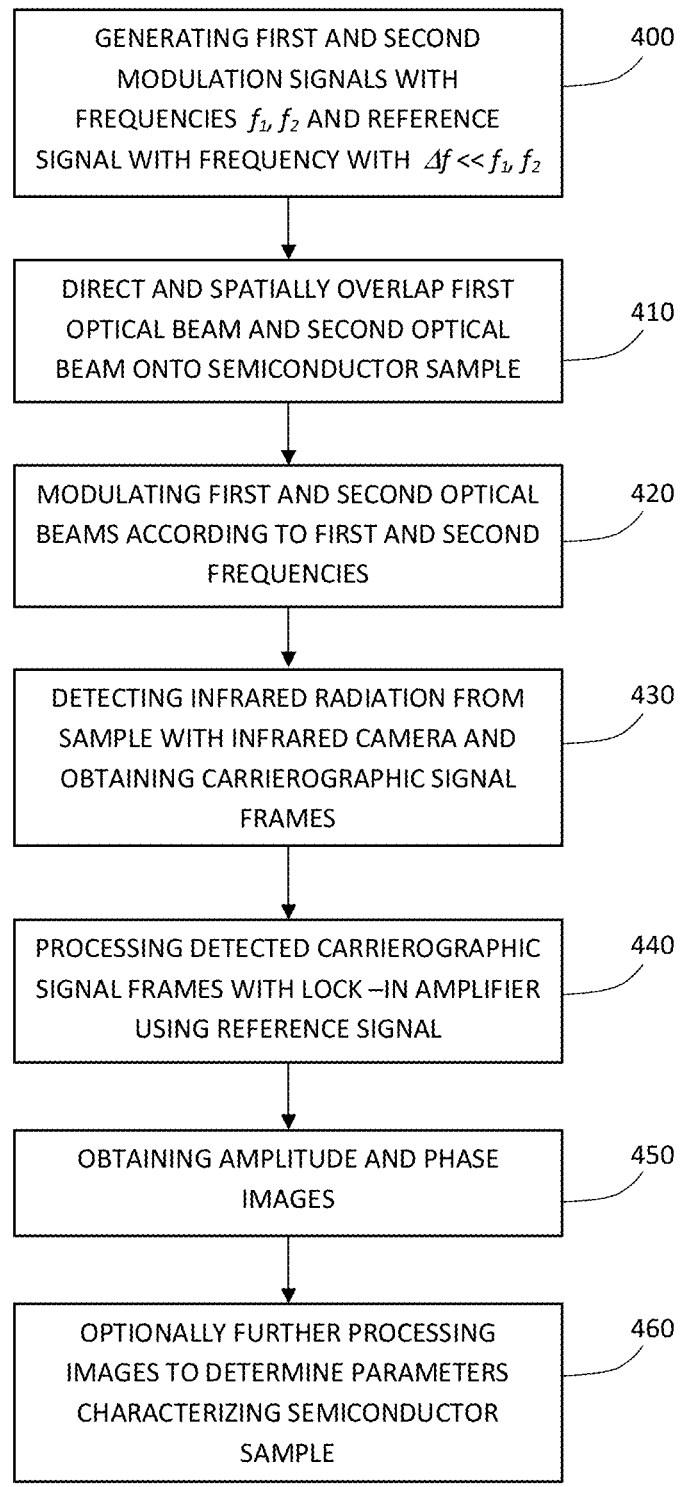
FIG. 5 is a flow chart illustrating a method of performing heterodyne imaging carrierography.

FIG. 5 provides a flow chart illustrating a method of heterodyne lock-in carrierographic imaging. In step 400, two modulation signals are generated (for example, via sinusoidal or square-waveform modulation) with frequency $f_1$ and $f_2=f_1+\Delta f$, $\Delta f \ll \{f_1,f_2\}$ respectively. As described below, these signals can be generated using a two-channel function generator. A reference signal having a frequency $\Delta f$ is also provided for subsequent lock-in processing of the carrierographic signals.

First and second optical beams are then directed and spatially overlapped onto the semiconductor sample in step 410. The optical beams have a wavelength selected to excite carriers in the semiconductor sample. The optical beams may be super-bandgap sources such as super-bandgap lasers. The first and second optical beams may have approximately equal average wavelengths. In step 420, prior to obtaining an image, the first and second optical beams are modulated in intensity according to the first and second modulation signals, respectively.

Infrared radiation emitted by the semiconductor sample in response to the absorption of the first and second modulated optical beams is then detected, in step 430, as a plurality of carrierographic signal frames, which are measured at selected points in time over at least one beat cycle (or beat period or interval). The detected carrierographic signal frames are provided to the lock-in amplifier in step 440, and amplitude and phase images are obtained in step 450. As will be further discussed below, the amplitude and/or phase images may be processed to infer one or more properties of the semiconductor sample, as shown in step 460.

Unlike the preceding direct lock-in carrierography embodiments, in which the modulation frequency was limited to approximately a few hundreds of Hz or less, the present heterodyne embodiment may involve modulation frequencies up to tens of kHz, or even beyond 100 kHz. In one embodiment, the modulation frequencies $f_1$ and $f_2$ are in the range of 1 to 100 kHz, and the beat frequency $\Delta f$ is selected to lie within the bandwidth of the imaging camera. In other embodiments, the modulation frequencies $f_1$ and $f_2$ may be in the range of 1 to 10 kHz, 10 to 50 kHz, 50 to 100 kHz, or greater than 100 kHz. It should be mentioned that no upper-frequency limit exists other than that imposed in practice by near-zero signals at very high frequencies due to plunging carrier-density wave amplitudes for $f \gg 1/(2\pi\tau)$.

An example range for the beat frequency $\Delta f$, which satisfies the condition of $\Delta f \ll \{f_1,f_2\}$, is approximately 5 to 100 Hz. It will be understood that the value of the beat frequency depends on the intensity of radiative recombination emissions. At high intensity smaller exposure times can be used and therefore higher beat frequencies. The beat frequency $\Delta f$ may be in the range of 5 to 100 Hz. In other example embodiments, the beat frequency $\Delta f$ may be in the range of 5 to 10 Hz, 10 to 20 Hz, 20 to 50 Hz, 50 to 100 Hz, or greater than 100 Hz.

In one embodiment, the modulation of the two light sources 102 and 104 (or beams 106 and 108) is activated at the first sampling instant and is stopped after each correlation period/cycle. As used herein, the phrase "correlation period" means the lock-in image processing period. This period depends on beat frequency, number of images per one iteration cycle, number of undersamplings, and number of iteration cycles used to average images in order to maximize SNR.

Amplitude and phase images are obtained from IP and Q images at the beat frequency $\Delta f$. The camera (or detector) exposure time may be selected to provide a sufficient signal to noise ratio. In one embodiment, the exposure time is selected to be the maximum available exposure time.

As noted above, any or all modulation signals can be produced by the data acquisition module USB 6259 without an additional function generator. Additionally, for heterodyne methods, the modulation signal may be used as the sum of two signals with frequencies $f_1$ and $f_2$, such that $f_1,f_2 \gg \Delta f = |f_1-f_2|$.

It will be recognized that the present methods do not require a local oscillator for heterodyne detection, unlike previously implemented diffusion-wave and other conventional heterodyne methods such as thermal-wave imaging. Previously known heterodyne detection methods (such as thermal wave imaging) require a local oscillator as the second wave with which the oscillating output is mixed to produce a signal at $\Delta f$. The present methods, which employ an imaging camera (such as an InGaAs camera) or a scanning system with a single detector, are suitable for obtaining images at very high frequencies (e.g. >several kHz, as needed for electronic process monitoring), compared to $\ll 1$ kHz for thermal-wave imaging. Obtaining images at such high frequencies introduces additional constraints in undersampling, also in view of the need for fast full surface area monitoring of semiconductor devices (such as solar cells) which exacerbates the time-spatial resolution problem. Furthermore, the present methods are different from known heterodyne detection methods due to the fact that the carrierographic heterodyne images are non-linear in nature (unlike thermal waves), with the result that there would be no heterodyne image in conventional heterodyne detection methods if the signal producing this image was not proportional to the excess free-carrier density wave to a power>1 (γ exponent in Equation 21, below). It is for this reason that two signals from the sample itself must be employed for heterodyne detection in the present methods, rather than a local oscillator and a sample signal (which would not work in the present case).

In order to overcome the severe frame-rate (undersampling) and exposure-time issues limiting direct high-frequency lock-in carrierography imaging, the present heterodyne scheme was introduced as described above. This scheme has the (stroboscopic) advantage of down-shifting the operating frequency into the range of the infrared camera capture capabilities even without undersampling, allowing one to optionally set the exposure time at the maximum value (as per the infrared camera's specifications) to yield optimum image SNR.

Figure 1B:
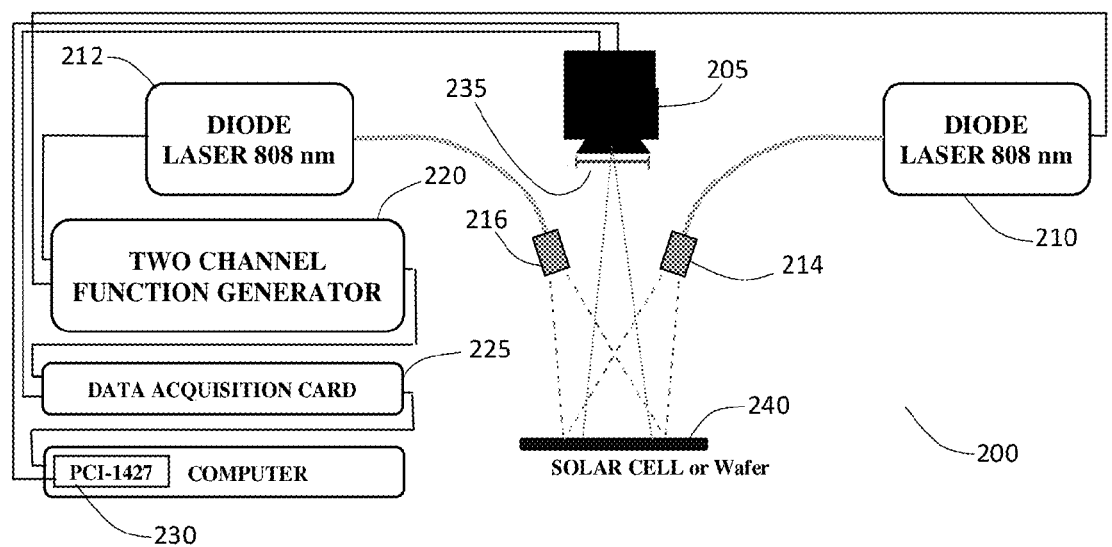
Figure 1C:
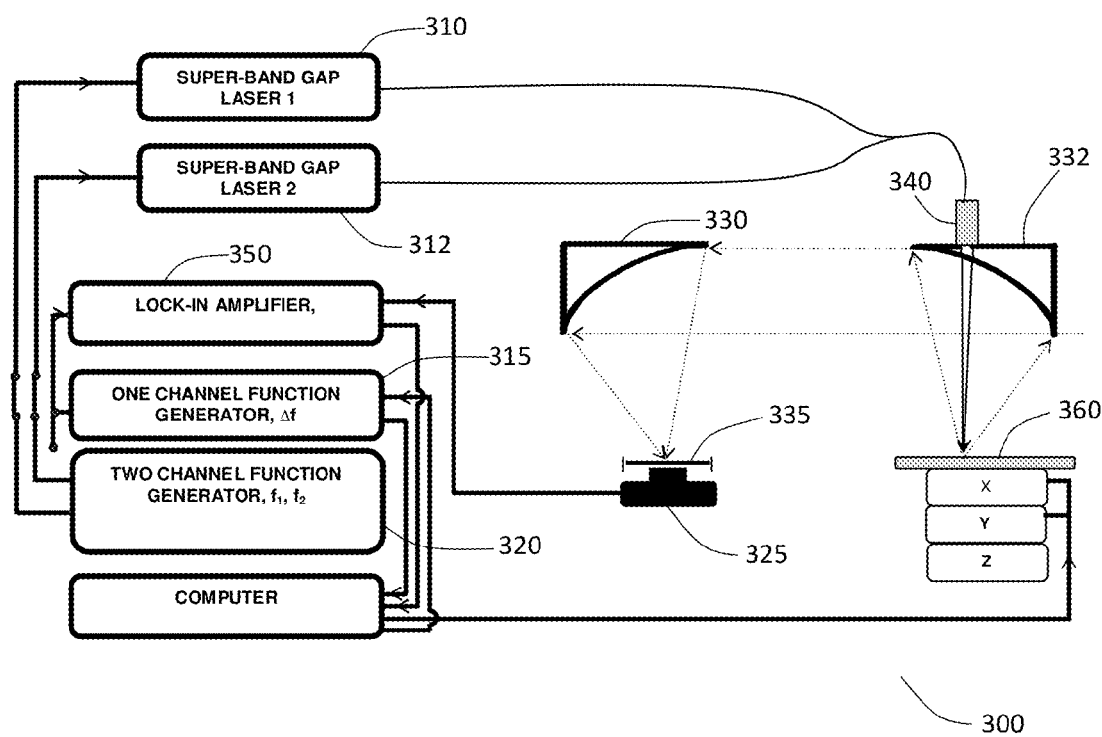

Example implementation of apparatus for performing lock-in heterodyne carrierography are shown in FIGS. 1(b) and 1(c), as further described in Example 1 below.

As further described below, the present method of heterodyne carrierography may be employed for the characterization of semiconductors and semiconductor devices, such as solar cells. In one example implementation, in which the semiconductor sample is a solar cell, the frequencies of the first and second modulating signals are selected such that the resulting carrierographic signal is sensitive to recombination lifetime limiting defect- and/or trap-state densities with minimal or no optical flooding artifacts as well as to the nonlinearity of the carrierographic signal to which it owes its origin.

In one embodiment, the heterodyne carrierography methods of the present disclosure may be employed for obtaining quantitative measurements of short lifetimes including the near-junction region in junction devices like solar cells, for which near-infrared cameras are too slow. Because areas with small lifetime have a low photoluminescence intensity, lock-in measurements are the preferable method for small signal measurements. According to PCR theory, the amplitude and phase PCR signal have their highest sensitivity to lifetime at a frequency around $f=1/(2\pi\tau)$. The present heterodyne method allows the spatial resolution of areas with low lifetime at the optimal frequency with max camera exposure time. The quantitative lifetime may be obtained in the manner outlined above using direct local lock-in PCR measurements, or on an image scale using a calibrated setup, with the calibration curve based on independent PCR frequency measurements in regions of several lifetime values fitted to PCR theory [5] and interpolated for amplitude and phase images within the range.

In another embodiment, the heterodyne carrierography methods of the present disclosure may be employed to perform high spatial and axial resolution lifetime profilometry. As was mentioned above, the main spatial resolution controller is the diffusion length of minority carrier waves, which approximately determines the spatial resolution (see Eq. 1). For example, to obtain high resolution, the dimensions of contrast-generating features such as electronic fault structures should be large or on the order of the ac diffusion length at the probe frequency. For example, by selecting at least 40 kHz modulation frequencies for the first and second optical beams, a lateral spatial resolution of approximately 90 microns of less may be achievable instead 280 microns in the case of dc photoluminescence images (silicon parameters: diffusion coefficient 20 $cm^2/s$, lifetime 40 microseconds). There is a trade-off between spatial resolution in regions characterized by short lifetime which tends to enhance spatial resolution, and the concomitant small carrierographic amplitude in those regions which degrades SNR.

In another example implementation, the heterodyne carrierography methods of the present disclosure may be employed for the detection of optoelectronic defect structures in semiconductor devices such as multicrystalline Si solar cells. These defects can be present in the original substrate e.g. as dislocations, grain boundaries, defect clusters etc, or can appear as the result of mechanical treatments. The spatial resolution of such defects is higher than dc photoluminescence imaging or low frequency lock-in carrierography.

As further shown and described below, the present methods may be used as a rapid imaging technology for contactless optoelectronic quality control of semiconductor substrates and junction devices such as solar cells at various stages of the fabrication process. According to selected embodiments, the resulting image may be of superior lateral spatial resolution than dc images such as photoluminescence and microwave photoconductivity, providing images with high axial resolution (equal to a carrier-wave diffusion length), thereby producing imaging contrast sensitive to local subsurface optoelectronic structures unlike the aforementioned imaging methods which produce images integrated over the full thickness of the wafer/substrate. In some example implementations, the heterodyne carrierography methods of the present disclosure may be employed for the characterization of semiconductor junctions such as a p-n junction. For example, by selecting modulation frequencies in the range of 2-100 kHz, which depends on minority carrier lifetime, suitable spatial resolution may be provided for resolving photon emission by band-to-defect recombining photocarriers within shallow subsurface depths commensurate with the diffusive boundary ranges of the p-n junction. As mentioned above, the depth resolution is limited by the carrier-wave diffusion length. Additionally, to improve depth resolution short wavelength excitation light sources are preferable with optical absorption depths commensurate with the p-n junction depth.

Digital Heterodyne Signal Processing

The processing of carrierographic images using heterodyne methods, as per the embodiments of the present disclosure, is now further explained. In the present section, the method of digital heterodyne signal processing is introduced. This is unlike the conventional heterodyne methods based on a beat formed using a local oscillator. In the sections that follow, the nonlinear aspect of the heterodyne measurement in semiconductors is further considered, and applications of the heterodyne methods to the high-frequency optical carrierography are presented.

A digital lock-in correlation procedure is performed as follows: In the case of n frames per correlation cycle, the intensity of each frame $I_j(x,y)$ is averaged through a desired number m of measurement repetitions:

$$I_j(x, y) = \frac{1}{m}\sum_{k=1}^{m} I_{j,k}(x, y), \quad (2)$$

where $I_{j,k}(x,y)$ is the value of the (x,y) pixel at the j-th frame ($1 \le j \le n$) for the k-th repetition ($1 \le k \le m$).

For harmonic modulation In-phase and Quadrature images are calculated from equations (3) and (4), respectively:

$$S^0(x, y) = \sum_{j=1}^{n} [I_j(x, y)\sin(2\pi f t_j)], \quad (3)$$

$$S^{90}(x, y) = \sum_{j=1}^{n} \{I_j(x, y)[-\cos(2\pi f t_j)]\} \quad (4)$$

Then, the lock-in amplitude and phase are calculated from equations (5) and (6)

$$\text{Amplitude}(x, y) = \left[[S^0(x, y)]^2 + [S^{90}(x, y)]^2\right]^{0.5} \quad (5)$$

$$\text{Phase}(x, y) = \tan^{-1}\left(\frac{S^{90}(x, y)}{S^0(x, y)}\right) \quad (6)$$

The digital heterodyne measurement technique is based on the same principle. For heterodyne lock-in imaging a sample is under modulated illumination with two different frequencies, $f_1$ and $f_2$. Lock-in processing is performed by the foregoing technique with frequency $$\Delta f = |f_1 - f_2|. \quad (7)$$

In order to effectively perform the present heterodyning method, the frequencies are synchronized. In one embodiment, synchronization is performed for all three frequencies; lock-in frequency $\Delta f$, modulation frequency $f_1$, and modulation frequency $f_2$; at the first frame for each correlation period.

Heterodyne Lock-in Carrierography of Non-Linear Optoelectronic Processes in Semiconductors Conventional lock-in heterodyne detection is by nature a non-linear process as it mixes different frequencies generating beat signals at $\Delta f = |f_1 - f_2|$ following low-pass filtering (LPF), which $\Delta f$ can be detected with a lock-in amplifier. In conventional heterodyne processing, one uses a local oscillator to generate an electrical (or other type of wave) signal at $f_1$ and mixes the said signal with the $f_2$ output of the physical process to which heterodyning is applied. The result is a high-to-low frequency shift and detection at the low beat frequency of high-frequency signals from physically linear processes (i.e. the output signal magnitude is linearly proportional to the excitation power or intensity).

Unlike conventional heterodyning, the present carrierography embodiment involves a non-linear physical optoelectronic process which does not lend itself to mixing with an external local oscillator and produces no signal under this condition.

The following analysis is provided to clarify the present methods of processing images for non-linear optoelectronic heterodyne lock-in carrierographic imaging. The analysis makes use of the trigonometric identity:

$$\sin(\alpha)\sin(\beta) = \frac{1}{2}\cos(\alpha-\beta) - \frac{1}{2}\cos(\alpha+\beta). \quad (8)$$

Any time-dependent non-linear signal $S(t)$ can be written as $$S(f(t)) = a_0 + a_1 f(t) + a_2 f(t)^2 + a_3 f(t)^3 + \ldots \quad (9)$$

In the case where $f(t)$ consists of two harmonic functions at frequencies $f_1$ and $f_2$, it can be written as $$f(t) = F[(A_1 \sin(2\pi f_1 t + \phi_1) + A_2 \sin(2\pi f_2 t + \phi_2)]. \quad (10)$$

The third term in Eq. (9) leads to the cross-product and its decomposition according to Equation (8)

$$2a_2 A_1 A_2 \sin(2\pi f_1 t + \phi_1)\sin(2\pi f_2 t + \phi_2) = a_2 A_1 A_2 \{\cos[2\pi(f_1-f_2)t + \phi_1 - \phi_2] - \cos[2\pi(f_1+f_2)t + \phi_1 + \phi_2]\} \quad (11)$$

This gives rise to the new frequency $\Delta f = f_1 - f_2$ following low-pass filtering (LPF).

To understand and simulate the heterodyne carrierographic signal and its non-linear physical origins, the two constituent signals can be written as $$S_1(t) = 0.5[1 + \sin(2\pi f_1 t)], \quad (12)$$

$$S_2(t) = 0.5[1 + \sin(2\pi f_2 t)]. \quad (13)$$

The time-dependence of the resulting carrierography (or PCR) signal can be expressed as $$S^*(t) = [S_1(t) + S_2(t)]^\gamma, \quad (14)$$

where $\gamma$ is the nonlinearity coefficient which arises due to the physics of the probabilistic radiative recombination mechanism underlying the carrierography (radiometrically captured) photon emissions [13] and or presence of p-n junction [14]. The spatial dependence of the signal has been omitted for clarity in this consideration.

In the example case of 16 images per correlation cycle, the signal generating each image pixel can be expressed as $$I_j^* = \int_{t_j}^{t_j+t_0} S^*(t) dt, \quad (15)$$

where $1 \leq j \leq 16$ and $t_0$ is the exposure time.

The reference signal is $$S_{ref}(t) = \sin[2\pi(\Delta f)t]. \quad (16)$$

In-phase and Quadrature signals are given according to equations 3 and 4, respectively:

$$S_*^0 = \sum_{j=1}^{16} [I_j \sin(2\pi(\Delta f)t_j)], \quad (17)$$

$$S_*^{90} = \sum_{j=1}^{16} \{I_j[-\cos(2\pi(\Delta f)t_j)]\} \quad (18)$$

Heterodyne amplitude and phase can be calculated according to Eqs. 5, 6, respectively, as $$A_H = \left[(S_*^0)^2 + (S_*^{90})^2\right]^{0.5} \quad (19)$$

and $$\Phi_H = \tan^{-1}\left(\frac{S_*^{90}}{S_*^0}\right) \quad (20)$$

Figure 6:
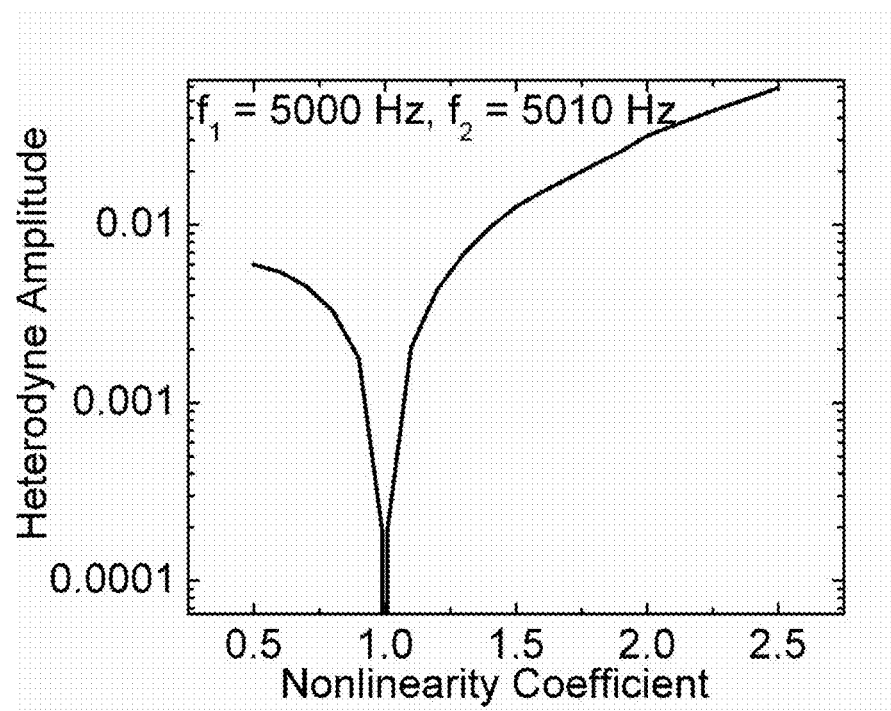
FIG. 6 plots the simulated dependence of heterodyne amplitude on non-linearity coefficient γ.

The result of a heterodyne amplitude simulation as a function of the non-linearity coefficient $\gamma$ is presented in FIG. 6.

According to this simulation, the heterodyne signal appears only in the case of the presence of non-linear contributing signals, unlike conventional heterodyne detection and consistently with experimental results provided in the Examples below. According to the methods disclosed herein, the laser excitation sources are both co-incident on the same region of interest (ROI) of the semiconductor sample without one source acting as an external local oscillator. The physical optoelectronic origin of signal non-linearity for silicon wafers and solar cells will be discussed below.

According to PCR theory [5,7], in the case of a silicon wafer the optically generated excess free-carrier-density wave (CDW) $\Delta N(z,\omega)$ at depth z and angular modulation frequency $\omega$ depends on the minority carrier-wave lifetime, the ambipolar diffusion coefficient, and front-surface and back-surface recombination velocities. All four transport parameters depend on the excess minority carrier concentration, which leads to one type of non-linearity of $\Delta N(z,\omega)$. Additionally, radiative band-to-band recombination in silicon depends non-linearly on the excess minority carrier density [13]. The exponent $\gamma$ is the degree of the non-linearity of the recombination process, indicating the radiative recombination probability into valence and bandgap trap states. Thus the carrierographic signal can be expressed as $$S(\omega) \approx F(\lambda_1, \lambda_2) \int_0^L [\Delta N(z, \omega)]^\gamma dz, \qquad [21]$$

where F is a function of the spectral bandwidth $(\lambda_1, \lambda_2)$ of the NIR detector, L is the thickness of the wafer. It is important to note that Equation 21 describes a single-layer system.

In case of a silicon solar cell with p-type base, the excess minority CDW $\Delta N(x,\omega)$ can be expressed by [14, 14a]

$$\Delta N(x, \omega) = \Delta p(x, \omega)|_{n-type\ layer} + \Delta n(x, \omega)|_{p-type\ layer}, \qquad (22)$$

where $$\Delta p(x) = A\cosh\left(\frac{x}{L_{wp}}\right) + B\sinh\left(\frac{x}{L_{wp}}\right) + \frac{\beta N_0 L_{wp}^2}{D_p(1 - \beta^2 L_{wp}^2)} \exp[-\beta(x + d)] \qquad (23)$$

for the n-type layer and $$\Delta n(x) = C\cosh\left(\frac{x}{L_{wn}}\right) + D\sinh\left(\frac{x}{L_{wn}}\right) + \frac{\beta N_0 L_{wn}^2}{D_n(1 - \beta^2 L_{wn}^2)} \exp[-\beta(x + d)]. \qquad (24)$$

For the p-type layer.

Coefficients A, B, C, D (integration constants) can be determined from conventional boundary conditions [14, 14a]

$$A = p_{n_0}\left[\exp\left(\frac{qV_p}{k_B T}\right) - 1\right] - \frac{\beta N_0 L_{wp}^2}{D_p(1 - \beta^2 L_{wp}^2)} \exp(-\beta d), \qquad (25)$$

$$B = A\left[\frac{v_{sf}\cosh(d/L_{wp}) + (D_p/L_{wp})\sinh(d/L_{wp})}{(D_p/L_{wp})\cosh(d/L_{wp}) + v_{sf}\sinh(d/L_{wp})}\right] + \qquad (26)$$

$$\frac{\beta N_0 L_{wp}^2}{D_p(1 - \beta^2 L_{wp}^2)}\left[\frac{v_{sf} + \beta D_p}{(D_p/L_{wp})\cosh(d/L_{wp}) + v_{sf}\sinh(d/L_{wp})}\right],$$

$$C = n_{p_0}\left[\exp\left(\frac{qV_p}{k_B T}\right) - 1\right] - \frac{\beta N_0 L_{wn}^2}{D_n(1 - \beta^2 L_{wn}^2)} \exp(-\beta d), \qquad (27)$$

$$C = n_{p_0}[[]]\left[e\exp\left(\frac{qV_p}{k_B T}\right) - 1\right] - \frac{\beta N_0 L_{wn}^2}{D_n(1 - \beta^2 L_{wn}^2)} \exp(-\beta d)$$

$$D = C\left[\frac{-v_{sb}\cosh(l/L_{wn}) - (D_n/L_{wn})\sinh(l/L_{wn})}{(D_n/L_{wn})\cosh(l/L_{wn}) + v_{sb}\sinh(l/L_{wn})}\right] - \qquad (28)$$

$$\frac{\beta N_0 L_{wn}^2}{D_n(1 - \beta^2 L_{wn}^2)}\left[\frac{v_{sb} + \beta D_n}{(D_n/L_{wn})\cosh(l/L_{wn}) + v_{sb}\sinh(l/L_{wn})}\right]$$

$$\exp[-\beta(d + l)],$$

$$L_{wn} \equiv \frac{L_n}{\sqrt{1 + i\omega\tau_n}}, \qquad (29)$$

$$L_{wp} \equiv \frac{L_p}{\sqrt{1 + i\omega\tau_p}}.$$

The PCR signal can be found according to $$S(\omega) = F\int_{-d}^{0} (\Delta p(x, \omega))^\gamma dx + F\int_0^L (\Delta n(x, \omega))^\gamma dx, \qquad (30)$$

where d is the depth of the p-n junction. Usually the depth of the junction is very shallow and significantly shorter than the base thickness. In this case only the first term in Equation (30) may be negligible. As can be seen from equations (25) and (27), an additional source of nonlinearity appears to be the photovoltage generated at the p-n junction.

Quantitative Solar Cell Carrierographic Imaging

Würfel [28] and Würfel et al. [29] have discussed non-equilibrium radiative electronic recombination transitions associated with non-thermal infrared photon emissions in semiconductors, in terms of a radiation chemical potential $\mu_\gamma$. The essence of their theory was to link these non-equilibrium optical (non-thermal luminescence) phenomena to their limiting (equilibrium) case $\mu_\gamma = 0$ in the framework of a thermodynamic treatment of radiation involving the generalization of Planck's radiation law for luminescence. Würfel's theory adapted to the case of the excitation of a solar cell p-n junction by an incident superband-gap photon flux of energy $E_i = \hbar\omega_i$ yields a relationship between the photovoltage appearing across the junction and the chemical potential of electron-hole pairs $$qV_{\hbar\omega} = \mu_e + \mu_h = \mu_\gamma, \qquad (31)$$

where q is the elementary charge. Here $\mu_e$, $\mu_h$ are the electron and hole quasi-Fermi levels.

The Stokes-shifted (photocarrier radiometric, PCR) photon flux [cm$^{-2}$ s$^{-1}$] emitted with infrared energy $E = \hbar\omega$ in response to the incident photon excitation and absorption is given by [28]

$$F_R(\hbar\omega; V_{\hbar\omega}, T) = \frac{A(\hbar\omega)}{4\pi^2\hbar^3 c^2}\left\{\frac{(\hbar\omega)^3}{\exp[(\hbar\omega - qV_{\hbar\omega})/kT] - 1}\right\}, \qquad (32)$$

where A is the absorptivity of the non-blackbody emitter of non-thermal radiation at energy $\hbar\omega$ and c is the speed of light in the medium ($= c_0/n_r$; $n_r$: medium refractive index). For indirect gap semiconductors like Si, the chemical potential $\mu_\gamma$ also includes the energy of either an emitted or an absorbed phonon acting as a mediator of the indirect band-to-band electronic transition [29].

This extra term can be incorporated in the (shifted, effective) value of $\hbar\omega$ in Equation (32), which essentially leaves the form of the equation unchanged. For semiconductor materials of bandgap energy $E_G > 1$ eV, the exponent of the denominator gives $\hbar\omega - qV_{\hbar\omega} \gg kT$, so that the emitted flux can be accurately approximated as $$F_R(\hbar\omega; V_{\hbar\omega}, T) \cong \left[\left(\frac{A(\hbar\omega)(\hbar\omega)^3}{4\pi^2\hbar^3 c^2}\right)e^{-\hbar\omega/kT}\right]\exp\left(\frac{qV_{\hbar\omega}}{kT}\right). \qquad (33)$$

In Equation (32) setting $V_{\hbar\omega} = 0$ results in the well-known equilibrium black-body Planck emission equation, the limit of zero chemical potential $\mu_\gamma$.

Non-radiative processes affect the excess photoexcited carrier density available for radiative recombination in dc-excitation processes, and the carrier density wave in ac-processes resulting from optical power modulation. The effect involves photon emission and absorption processes with energies $E_{NR} = \hbar\omega_{NR}$, especially important in indirect semiconductors like Si [29]; it is manifested as decreased photovoltage $V\hbar_\omega = \mu_\gamma$, which also decreases the PCR photon flux. The total flux is $$F_T(V\hbar_\omega, T) = \eta_R(T)F_R(\hbar\omega, V\hbar_\omega, T) + \eta_{NR}F_{NR}(\hbar\omega_{NR}, T), \quad (34)$$

where $\eta_R$ and $\eta_{NR}$ are the radiative and non-radiative (quantum) efficiencies, respectively.

These efficiencies can be expressed in terms of radiative and non-radiative recombination probabilities [30]:

$$\eta_R(T) = \frac{P_R(T)}{P_R(T) + P_{NR}(T)}, \quad (35)$$

$$\eta_{NR}(T) = \frac{P_{NR}(T)}{P_R(T) + P_{NR}(T)},$$

provided no other energy conversion pathways exist. For solar or other optical superband-gap illumination, $\eta_R$ becomes a function of the generated photovoltage:

$$\eta_R(T) = \frac{F_R(\hbar\omega, T) - F_R(0, T)}{F_A(\hbar\omega_i)} = \frac{F_R(0, T)}{F_A(\hbar\omega_i)}\left[\exp\left(\frac{qV_{\hbar\omega}}{kT}\right) - 1\right]. \quad (36)$$

Here $F_A$ is the absorbed flux of incident photons and $F_R(0, T)$ is the background (residual) equilibrium flux (in the dark), given by Equation (33) with $V\hbar_\omega = 0$. Under equilibrium conditions Kirchhoff's law applies and the residual radiative emission becomes thermal. The emission rate is then equal to the absorption rate.

Equation (36) can be written in terms of the photon flux incident on the solar cell and the non-radiative recombination (thermal generation) flux can be added to the overall photon conversion. Simplifying the notation:

$$F_A(\hbar\omega_i) = \frac{1}{\eta_R}[F_R(V_{\hbar\omega}) - F_R(0)] + \eta_{NR}F_{NR}. \quad (37)$$

This equation is valid under open-circuit conditions, assuming that both radiative and non-radiative recombinations can occur. Under closed-circuit conditions (the most general case), an optical-to-photocurrent energy conversion pathway must be added which gives rise to a photocurrent flux, $F_C$, on the right hand side of Equation (37):

$$F_A(\hbar\omega_i) = \frac{1}{\eta_R}[F_R(V_{\hbar\omega}) - F_R(0)] + \eta_{NR}F_{NR}F_C. \quad (38)$$

Now we define the following current densities (charge fluxes, [A/m²]):

$$J(V_{\hbar\omega}) \equiv qF_c(V_{\hbar\omega}) \quad (39)$$

$$J_{SC}(\hbar\omega_i) \equiv qF_A(\hbar\omega_i)$$

$$J_0(\hbar\omega) \equiv \frac{1}{\eta_R}[qF_R(0)] = \frac{1}{\eta_R}\left[\frac{qA(\hbar\omega)(\hbar\omega)^3}{4\pi^2\hbar^3c^2}\right]\exp\left(-\frac{\hbar\omega}{kT}\right)$$

$$J_{NR} \equiv \eta_{NR}qF_{NR}$$

Rearranging Equation (38) while taking Equation (36) into account, and introducing definitions (39) results in $$J(V_{\hbar\omega}) = J_{sc}(\hbar\omega_i) - J_0(\hbar\omega)\left[\exp\left(\frac{qV_{\hbar\omega}}{kT}\right) - 1\right] - J_{NR}. \quad (40)$$

This equation can now be compared to the solar cell diode equation without series resistance and ideality factor n:

$$J(V) = J_{SC} - J_0\left[\exp\left(\frac{qV}{nkT}\right) - 1\right] - (V/SR_{sh}), \quad (41)$$

where S is the surface area of the solar cell and $R_{sh}$ is the shunt resistance. The comparison reveals that the radiative diode equation (40) involves unity ideality factor, and a reverse optical flux (saturation current density-equivalent factor) $J_0$, which depends on $F_R(0)\eta_R$, where $F_R(0)$ is the blackbody flux radiated by the solar cell (and equally absorbed at equilibrium) in the dark and $\eta_R$ includes the non-equilibrium (non-thermal) radiation processes, Equation (36). Higher radiative efficiencies produce less optical saturation current, as expected. Similarly, $\eta_{NR}F_{NR}$ is the thermal current flux and produces effects similar to the electrical shunt resistance: $\eta_{NR}F_{NR} = 0$ corresponds to $R_{sh} \to \infty$, i.e. there are no losses (thermal emissive or electrical).

Despite their formal similarity, the important difference between equations (40) and (41) is that the latter connects purely electrical quantities: the measurable current density, J, flowing out of the solar cell as a function of the photovoltage, V, across the junction, whereas the former links an optically measurable quantity, the non-equilibrium radiative flux $J_0(\hbar\omega)\exp(qV\hbar_\omega/kT)$, to the electrical current density. Therefore, the importance of Equation (40) lies in the fact that it provides a linkage between fully non-contacting, remote photocarrier radiometric measurements of radiative emission rates (like DC PL, modulated PCR signals, and carrierographic images) and solar cell electrical parameters which otherwise require contacting electrical measurements and the presence of electrode grids.

As a byproduct of the formal similarity between equations (40) and (41), a number of expressions can be derived from Equation (40) between radiative fluxes, current densities and photovoltages by using well-known electrical relations for solar cells stemming from Equation (41). The relevant quantities are: the open-circuit photovoltage $$V_{\hbar\omega}^{OC} = V_{\hbar\omega}(J = 0) = \left(\frac{kT}{q}\right)\ln\left(1 + \frac{\Delta J}{J_0}\right) \cong \left(\frac{kT}{q}\right)\ln\left(\frac{\Delta J}{J_0}\right), \quad (42a)$$

where $\Delta J \equiv J_{SC} - J_{NR}$ (for conventional solar cells $J_0 \ll \Delta J$); and the closed-circuit photovoltage $$V_{\hbar\omega}(J) = \left(\frac{kT}{q}\right)\ln\left(1 + \frac{\Delta J}{J_0} - \frac{J}{J_0}\right) \cong \left(\frac{kT}{q}\right)\ln\left(\frac{\Delta J - J}{J_0}\right). \quad (42b)$$

The output photovoltaic power density is $P\hbar_\omega = JV\hbar_\omega$. Maximizing the power density with respect to photovoltage, $$\frac{\partial P_{\hbar\omega}}{\partial V_{\hbar\omega}} = 0,$$

yields the optical equivalent of the well-known transcendental equation for the photovoltage, $V\hbar_\omega^{mp}$, at maximum output power $$\exp\left(\frac{qV_{\hbar\omega}^{mp}}{kT}\right)\left[1+\left(\frac{qV_{\hbar\omega}^{mp}}{kT}\right)\right] = 1 + \frac{\Delta J}{J_0} = \exp\left(\frac{qV_{\hbar\omega}^{OC}}{kT}\right), \quad (43)$$

which, when combined with the expression $$J_{mp} \equiv J(V_{\hbar\omega}^{mp}) = \Delta J - J_0\left[\exp\left(\frac{qV_{\hbar\omega}^{mp}}{kT}\right) - 1\right], \quad (44)$$

obtained from Equation (40), results in the following expression for the maximum power density $$P_{max} = J_{mp}V_{\hbar\omega}^{mp} = \frac{(qV_{\hbar\omega}^{mp}/kT)V_{\hbar\omega}^{mp}\Delta J}{1+(qV_{\hbar\omega}^{mp}/kT)}\left(1+\frac{J_0}{\Delta J}\right). \quad (45)$$

The maximum solar conversion efficiency is given by $$\eta_{max} = \left[\frac{(qV_{\hbar\omega}^{mp}/kT)}{1+(qV_{\hbar\omega}^{mp}/kT)}\right]\frac{V_{\hbar\omega}^{mp}\Delta J}{P_i}, \quad (46)$$

where $P_i$ is the incident superband-gap optical or solar power. With $qV\hbar_\omega^{mp}$~0.5-0.6 eV for Si solar cells [30] and room-temperature kT=0.026 eV, Equation (46) can be simplified:

$$\eta_{max} = \frac{V_{\hbar\omega}^{mp}\Delta J}{P_i} \cong \frac{V^{OC}\Delta J[FF]}{P_i}. \quad (46a)$$

An expression for the fill factor has been provided by Ghosh et al. [31]

$$FF \cong \left[1-\frac{1}{\ln(J_{SC}/J_0)}\right]\left[1-\frac{\ln[\ln(J_{SC}/J_0)]}{\ln(J_{SC}/J_0)}\right] \approx 1 - \frac{1}{\ln(J_{SC}/J_0)} \quad (47)$$

Therefore, from Equation (42a), to first order with $J_{SC} \gg J_0$:

$$\eta_{max} = \left(\frac{nkT}{q}\right)\frac{\Delta J}{P_i}[\ln(\Delta J) + \ln(J_0)]. \quad (48)$$

This equation indicates that for an ideal solar cell there is a logarithmic decrease of solar conversion efficiency with reverse radiative saturation current. Its electronic counterpart has been confirmed by Fahrenbruch and Bube (Ref. [30], p. 216, FIG. 6.5) for a wide range of non-ideality factors. When using Equation (40) instead of the conventional Equation (41), the solar conversion efficiency is given by $$\eta_{max} = \left(\frac{nkT}{q}\right)\frac{\Delta J}{P_i}\left[\ln\left(\frac{\Delta J}{qF_R(0)}\right) + \ln(\eta_R)\right]. \quad (49)$$

Here a non-ideality factor n was added ad hoc, in order to account for physical PCR and carrierographic responses of the p-n junction. In the framework of the chemical potential formalism of non-thermal radiation [28], $\eta_{max}$ plays the role of the maximum chemical potential, $\mu_{\chi max}$ (quasi-Fermi level difference) of the radiative emission by recombining free electron-hole photocarriers.

From the definition of $\eta_R$, Equation (36)

$$\eta_R(T) = \frac{F_R(\hbar\omega, T) - F_R(0, T)}{F_A(\hbar\omega_i)} = \frac{J_R(V_{\hbar\omega}) - J_R(0)}{J_{SC}} \equiv \frac{J_{PCR}(V_{\hbar\omega})}{J_{SC}} \quad (50)$$

where $J_R(V\hbar_\chi) \equiv qF_R(V\hbar_\omega)$, and $J_{PCR}(V\hbar_\omega) \equiv q[F_R(V\hbar_\omega) - F_R(0)]$ is the photocarrier radiometric photon (luminescence) current density, a non-equilibrium quantity which can also be used for the definition of radiative non-thermal emission rates which generate carrierographic imaging. The radiatively recombining carriers are generated by the absorbed photon flux $F_A$, and their density is limited by competing non-radiative and external electrical current generation processes.

For photocarrier excitation modulated at frequency $\omega_M$, leading, e.g., to PCR signals from a laser spot and single photodetector element detection, or to AC carrierographic (LIC) imaging (broad surface excitation and camera detection), the emitted non-thermal optical current density identified as $J_{PCR}(V\hbar_\omega)$ is proportional to the depth integral of the excess photogenerated carrier density $\Delta N(z, \omega)$ [8] over the wafer thickness L, generalized for the physics of non-linear radiative recombination processes [32] with non-linearity coefficient $\gamma$ $$J_{PCR}(V\hbar_\omega;\omega_M) = K\int_0^L \Delta N^\gamma(z,\omega_M)dz = CS_{cG}(\omega_M) \quad (51)$$

Here K and C are constants independent of the photocarrier depth profile. Equation (51) shows that the same depth integral is responsible for the carrierographic signal, $S_{CG}(\omega_M)$, as captured by a near-infrared camera. From equations (49)-(51) the following expression is obtained for the maximum solar conversion efficiency:

$$\eta_{max} = \left(\frac{nkT}{q}\right)\frac{\Delta J}{P_i}\left[\ln\left(\frac{\Delta J}{qF_R(0)}\right) + \ln[CS_{CG}(\omega_M)]\right] \quad (52)$$

This expression predicts a logarithmic relationship between the local carrierographic signal and the measured solar conversion efficiency. It should be noted that for signals at angular modulation frequency $\omega_M$, such as PCR and LIC imaging, complex quantities $\Delta J$, $P_i$ and $S_{CG}(\omega_M)$ are implied in Equation (52). The general form of these quantities is $Z(\omega_M) = |Z(\omega_M)|e^{i\Phi(\omega_M)}e^{i\omega_M t}$ and Equation (52) remains valid in its complex version: An amplitude expression is obtained upon substitution of |Z| for each complex quantity Z.

Equation (52) can be used for quantitative measurements of CG images of optoelectronically inhomogeneous solar cells with respect to local maximum radiative recombination efficiency. Introducing mean-value definitions over the illuminated surface, S, of a solar cell:

$$\langle\eta\rangle = \frac{1}{S}\iint_{x,y}\eta_{max}(x,y)dxdy \quad (53)$$

-continued $$\langle S_{CG}(\omega_M) \rangle = \frac{1}{S} \int\!\!\int_{x,y} S_{CG}(x, y; \omega_M) dx dy$$

and using an approximation based on the smaller change of spatially variable logarithmic functions compared to linear functions, one obtains:

$$\left\langle \Delta J \ln\left(\frac{\Delta J}{qF_R(0)}\right)\right\rangle = \frac{1}{S}\int\!\!\int_{x,y} \Delta J(x, y)\ln\left[\frac{\Delta J(x, y)}{qF_R(0)}\right] dx dy \cong \quad (54)$$

$$\frac{1}{S}\left\langle \ln\left[\frac{\Delta J(x, y)}{qF_R(0)}\right]\right\rangle \int\!\!\int_{x,y} \Delta J(x, y) dx dy = \langle \Delta J \rangle \left\langle \ln\left[\frac{\Delta J(x, y)}{qF_R(0)}\right]\right\rangle$$

Similarly, the approximation $$\langle \Delta J \ln [CS_{CG}(\omega_M)]\rangle \approx \langle \Delta J \rangle \ln [CS_{CG}(\omega_M)] \quad (55)$$

can be adopted by means of the same approximation, and Equation (52) can be rearranged and written in a mean-value form, averaged over the extent of the illuminated solar cell surface $$\langle \ln[CS_{CG}(\omega_M)]\rangle = \left(\frac{qP_i}{nkT}\right)\langle \eta_{max}(\omega_M)\rangle - \left\langle \ln\left[\frac{\Delta J}{qF_R(0)}\right]\right\rangle \quad (56)$$

This equation assumes a constant flux of optical illumination power over the illuminated surface of the solar cell. It also assumes that each pixel of the recombination-radiation-capturing camera receives a photon flux at the maximum local chemical potential, i.e. at $V\hbar_\omega^{OC}$. This is the case with the CG response of a solar cell irradiated at open circuit or even during the fabrication process, before electrodes are attached to it.

Owing to the strongly damped distribution of the carrier diffusion wave, a function of $\omega_M$, as a function of subsurface depth, the mean value $\langle \eta \rangle$ will depend on $\omega_M$ as indicated in Equation (56), because integration over the wafer thickness, Equation (51), will yield different depth distributions of local radiative recombination efficiencies at different modulation frequencies in strongly electronically depth-inhomogeneous devices like solar cells, on account of the frequency-dependent AC carrier diffusion length (Eq. 1) [7].

This implies that CG images of the same device obtained at different modulation frequencies will generally be different, the result of contrast variations generated by the local values of $\eta_R(x,y,z)$ radiative recombination efficiency.

Now, turning to the complex nature of the rhs of Equation (52), one may write $$CS_{CG}(\omega_M) = |CS_{CG}(\omega_M)| \exp[i\phi_{CG}(\omega_M)] \Delta J(\omega_M) = |\Delta J(\omega_M)| \exp[i\phi_{\Delta J}(\omega_M)] P_i = |P_i| \quad (57)$$

where the common time modulation factor $e^{i\omega x}$ has been omitted for simplicity. Rearrangement of Equation (52) with $P_i$ transferred to the lhs, and separation of real and imaginary parts yields the following equation for the imaginary part, a relation between the CG phase and the maximum solar conversion efficiency:

$$\phi_{CG}(\omega_M) = -\left(\frac{q|P_i|\sin(\phi_{\Delta J})}{kT|\Delta J(\omega_M)|}\right)\eta_{max}(\omega_M) - \phi_{\Delta J}(\omega_M) \quad (58)$$

This relation can be extended to the mean-value (average) of the phase over the illuminated surface area in a manner and approximations similar to those used in the derivation of Equation (56):

$$\langle \phi_{CG}(\omega_M)\rangle = -\left\langle\left(\frac{q|P_i|\sin(\phi_{\Delta J})}{kT|\Delta J(\omega_M)|}\right)\right\rangle\langle\eta_{max}(\omega_M)\rangle - \langle\phi_{\Delta J}(\omega_M)\rangle \quad (59)$$

The foregoing theory can also be used to predict the dependence of the carrierographic amplitude on photovoltage. From the definition of $V\hbar_\omega$, Equation (42b), with $J_0$ from Equation (9) and $J_{PCR}(V\hbar_\omega) \equiv q[F_R(V\hbar_\omega) - F_R(0)]$, the following expression can be derived:

$$V_{\hbar\omega} = \left(\frac{nkT}{q}\right)\frac{\Delta J}{P_i}\left[\ln\left(\frac{\Delta J - J}{qF_R(0)}\right) + \ln[CS_{CG}(\omega_M)]\right] \quad (60)$$

which also yields $$V_{\hbar\omega}^{OC} = \left(\frac{nkT}{q}\right)\frac{\Delta J}{P_i}\left[\ln\left(\frac{\Delta J}{qF_R(0)}\right) + \ln[CS_{CG}(\omega_M)]\right] \quad (61)$$

A relationship between the DC photovoltage, V, and the excess minority carrier density has been presented by Trupke et al. [32] in the form $$qV = \Delta\eta \approx kT \ln\left(\frac{\Delta N(\Delta N + N_D)}{n_i^2}\right) \approx kT \ln(I_{PL}) + C \quad (62)$$

Equation (62) bears a similarity to Equation (60) in terms of the functional dependence between excess carrier density-dependent quantities and photovoltage, but it does not account for depth inhomogeneity or the depth-integrated nature of radiative emission efficiencies, nor does it specify what constitutes the empirical constant C. Here, $\Delta\eta$ is the separation of the quasi Fermi energies, $N_D$ is the doping density, $\Delta N$ is the excess minority carrier concentration, $n_i$ is the equilibrium carrier density, and $I_{PL}$ is DC photoluminescence intensity.

The derivation of Equation (62) assumed $\Delta\eta$ to be constant along the width of the solar cell base. The mean-value form of Equation (60), averaged over the extent of the illuminated solar cell surface is $$\langle V_{\hbar\omega}(\omega_M)\rangle \cong \left(\frac{nkT}{q}\right)\frac{\langle\Delta J\rangle}{P_i}\left[\left\langle\ln\left(\frac{\Delta J - J}{qF_R(0)}\right)\right\rangle + \langle\ln[CS_{CG}(\omega_M)]\rangle\right] \quad (63)$$

The corresponding expression for $\langle V\hbar_\omega^{OC}(\omega_M)\rangle$ with J=0 can be readily derived from Equation (63). There are several methods for quantitative determination of wafer and device parameters from lock-in carrierography (LIC) and heterodyne carrierography (HDC). According to one embodiment, pre-determined calibration data can be employed to extract parameters from the carrierographic images.

According to another example embodiment, theoretical PCR curves can be obtained from frequency-scanned data obtained from localized focused laser excitation. This predetermined calibration data may be used for both LIC and HDC. For example, a correlation may be made between the intensity of LIC or HDC and measurements determined from frequency scan lifetime for two locations on the surface of sample with high and low intensity, which allows for a determination of calibration dependence between intensity and lifetime under assumption of linear proportionality.

In the case of wafer substrates the fundamental carrier transport parameters, such as the minority carrier recombination lifetime, electronic diffusivity, and front and back surface recombination velocities, can be extracted from PCR frequency scans. The same procedure can be applied to solar cells which, however, require a theoretical model according Eqs. 22-30 or in [14]. Additionally, other parameters of the solar cell, such as the open circuit voltage, volt-current characteristics, efficiency, shunt resistance, and series resistance may be extracted on the basis of the theory. It should be mentioned that calculation and fitting should be performed for all image pixels, a time-consuming procedure.

Alternative implementations include a) calibrated statistical pixel-captured radiative emission distributions over the illuminated surface and their dependence on device parameters as described in the foregoing theory; and b) effective lifetime images of the illuminated area with quantitative values as interpolations of PCR frequency scan-derived transport properties obtained at several surface locations with different carrierographic amplitudes.

Lock-in Carrierographic Phase Image for Effective Lifetime Mapping of Wafers

In this example embodiment, quantitative self-calibrating LIC imaging of wafers is introduced and described. Unlike previous methods resulting in qualitative LIC images, the present embodiment employs quantitative LIC imaging to provide effective lifetime maps of a semiconductor wafer or substrate. The method is based on a simplified version of the integrated diffuse carrier-wave density presented by Eq.21. Eq. 21 can be replaced by a rate equation model:

$$S(\omega) = \frac{\tau_e K}{1 + i\omega\tau_e} \quad (64)$$

where K is a material-property-dependent constant and $\tau_e$ is the effective lifetime which is a combination of the bulk and surface lifetimes [36]

$$\tau_e = \left(\frac{1}{\tau_b} + \frac{1}{\tau_s}\right)^{-1}. \quad (65)$$

Here $\tau_s$ is the surface lifetime, a function of the surface recombination velocity (SRV). The phase of the simplified model has the form $$\phi(\omega) = -\tan^{-1}(\omega\tau_e) \quad (66)$$

With the phase-frequency dependence of all pixels in the carrierographic image fitted to Eq. 66, the effective carrier lifetime map can be obtained. In principle, the one phase image at fixed frequency is enough for extracting of quantitative effective lifetime map. In this case the frequency should be enough to allow sufficient value of phase on all ROI with high SNR. The use of several frequencies and following fit increase significant the precision of lifetime map. Additionally, there may be instrumental phase offset issues which prevent the self-calibration of the technique.

It should be mentioned, that the effective carrier lifetime map can also be obtained from amplitude images according to Eq. 64. In this case a minimum of two images at different frequencies should be used, because there is additional parameter K.

All above-mentioned considerations and procedures can be used for lifetime mapping of a wide range of semiconductor substrates and devices. For example, the methods may be employed for lifetime mapping of wafers with p-n junctions (solar cells).

Experimental results from an example implementation of this model are shown below in Example 8.

Lock-in Carrierographic Image Pixel Brightness Dependence on Solar Cell Electrical Parameters In some embodiments, additional electrical parameters pertaining to a solar cell may be extracted using the statistical distribution of LIC images. The calculations are based on modification of Eq. 40, for only related to the non-equilibrium radiative processes and definitions:

$$J[\hbar\omega, V(\hbar\omega), T]_R = J_R - J_{R0}\left[\exp\left(\frac{qV(\hbar\omega)}{n_j k_B T}\right) - 1\right] \quad (67)$$

where $$J[\hbar\omega, V(\hbar\omega), T]_R = q \cdot C_{LIC}[\langle|LIC(V_{OC})|\rangle - \langle|LIC[V(\hbar\omega)]|\rangle] \quad (68)$$

$$J_R = q \cdot \eta\eta_R(\hbar\omega, V_{OC}, T)F_i(\hbar\omega) \quad (69)$$

$$J_{R0} = qF_R(0, T) \quad (70)$$

$$\eta\eta_R(V_{OC}, T)F_i(\hbar\omega) = C_{LIC}[\langle|LIC(V_{OC})|\rangle - \langle|LIC(0)|\rangle] \quad (71)$$

$$F_R(0, T) \cdot \left[\exp\left(\frac{qV(\hbar\omega)}{n_j k_B T}\right) - 1\right] = C_{LIC}[\langle|LIC(V(\hbar\omega))|\rangle - \langle|LIC(0)|\rangle] \quad (72)$$

Here $C_{LIC}$ is calibration factor for LIC; $n_j$ is optoelectronic ideality factor related to radiative recombination processes; $\eta$ is quantum efficiency for carrier photogeneration; $\langle|LIC(V(\hbar\omega))|\rangle$ is LIC amplitude-averaged.

Equation (68) can be compared to the conventional solar cell diode equation without series and shunt resistance:

$$J(V) = J_g - J_0\left[\exp\left(\frac{qV}{nk_B T}\right) - 1\right] \quad (73)$$

It can be found on basis these equations the calibration factor and correlation between electrical parameter and LIC parameters as $$C_{LIC} = \frac{|I_i|(1-R)\eta}{\hbar\omega_{in}[\langle|LIC(V_{OC})|\rangle - \langle|LIC(0)|\rangle]}\left(\frac{1 - \eta_{ce}(\hbar\omega, 0, T)}{1 - \lambda_{in}\lambda_{em}^{-1}}\right) \quad (74)$$

$$J_g = qC_{LIC}J_R\left[\frac{1 - \lambda_{in}\lambda_{em}^{-1}}{\eta_{ce}(\hbar\omega, 0, T)^{-1} - 1}\right] \quad (75)$$

$$J_0 = qC_{LIC}J_{R0}\left[\frac{1 - \eta_{ce}(\hbar\omega, 0, T)}{1 - \lambda_{in}\lambda_{em}^{-1}}\right]^2 \quad (76)$$

$$n = n_j\frac{\ln\left(\frac{J_R}{J_{R0}}\right)}{\ln\left[\eta_R\frac{J_R}{J_{R0}}\right]} \quad (77)$$

-continued $$V_{OC} \approx n\frac{k_B T}{q}\ln\left(\frac{J_g}{J_{D0}}\right) = n_j\frac{k_B T}{q}\ln\left(\frac{J_R}{J_{R0}}\right) \quad (78)$$

$$FF \cong \left[1 - \frac{1}{\ln(J_g/J_0)}\right]\left[1 - \frac{\ln[\ln(J_g/J_0)]}{\ln(J_g/J_0)}\right] \approx \quad (79)$$

$$1 - \frac{1}{\ln\left(\frac{J_R}{J_{R0}}\frac{1-\lambda_{in}\lambda_{em}^{-1}}{\eta_{ce}(\hbar\omega, 0, T)^{-1} - 1}\right)}$$

Here $J_g$ is photogeneration current density; $J_0$ is saturation current density, $I_i$ is peak value of incident modulated illumination intensity; is photon wavelengths corresponding incident illumination, $\lambda_{in}$ is photon wavelengths corresponding to photoemission; $\eta_{ce}$ is photocarrier-to-current collection efficiency. In one example implementation, one or more of the electrical parameters listed above are obtained by measuring a plurality of lock-in-carrierography images at different load resistances, obtaining average lock-in-carrierography signals from the measured images, and fitting the average signals to the mathematical relationships provided above. In another example implementation, one or more of the electrical parameters listed above are obtained in a non-contact manner by measuring a plurality of lock-in-carrierography images at different optical intensities, obtaining average lock-in-carrierography signals from the measured images, and fitting the average signals to the mathematical relationships provided above.

Experimental results from an example implementation of this model are shown below in Example 9.

The following examples are presented to enable those skilled in the art to understand and to practice the present invention. They should not be considered as a limitation on the scope of the invention, but merely as being illustrative and representative thereof.

EXAMPLES

Example 1

DC Photoluminescence, Direct and Heterodyne Lock-in Carrierography of a Multicrystalline Solar Cell and a Silicon Wafer To highlight the features of lock-in HDC, compared to conventional optoelectronic imaging methods such as DC photoluminescence and direct LIC, experimental results with these imaging methods and heterodyne lock-in carrierography of multicrystalline Si solar cell of various dimensions are shown in FIGS. 7-10.

The apparatus 200 employed to perform the carrierographic measurements is shown in FIG. 1(b), and consisted of a high-speed NIR InGaAs snapshot camera 205 with windowing, two fiber coupled 808-nm 9-W diode lasers 210 and 212, optical blocks 214 and 216 with collimator and diffuser, a two-channel function generator 220, a data acquisition module 225 and a frame grabber 230. A long-pass filter 235 is used to prevent the excitation laser beams from interfering with the NIR camera 200.

The near infrared InGaAs camera employed (SU320KTSW-1.7RT/RS170 from Goodrich Sensors Unlimited) had a 320×256 pixel active element, spectral bandwidth 0.9-1.7 μm, noise equivalent irradiance <2.5×10⁹ photons/cm²·s, and maximum frame-rate 119 fps for 320×256 window size and 11700 fps for 16×16 window size full-frame, exposure times 16.6 ms to 0.13 ms (at full frame) and up to 0.035 ms for 8×8 window size electronic shutter.

A long-pass filter LP-1000 nm from Spectrogon with >70% transmission for spectral range 1000-2200 nm was used to block the excitation laser beam from the InGaAs camera. Fiber coupled 808 nm infrared diode lasers IMLF-808-9WFMDA4M from Lasermate Group, Inc., with power stability <1% at the maximum output power 9 W operate in the CW mode with adjustable output power and TTL/Analog modulation up to 10 kHz without decreasing modulation depth. AC amplitude decreases twice at approximately 80 kHz.

The optical block provided homogeneous illumination of a sample or device 240 and consisted of a collimator F810SMA-780 from THORLABS and Square Pattern Engineered Diffuser ED1-S20-MD from THORLABS.

A two-channel high-precision Agilent Pulse Function Arbitrary Generator 81150A from Agilent Technologies provided 1 μHz-120 MHz pulse generation with variable rise/fall time of versatile waveforms and modulation capabilities. The data acquisition module USB 6259 (National Instruments, not shown) was used to generate sinusoidal or square waveform modulation and reference signals from one of its analog outputs and the trigger signal of the infrared camera from its digital I/O.

The camera images are read by the computer using a PCI-1427 frame grabber 230 from National Instruments to produce computer-generated amplitude and phase images. The software for processing and synchronization (direct and heterodyne lock-in processing) was developed using the LabVIEW™ environment.

Direct lock-in carrierography can also be implemented in apparatus shown in FIG. 1(b) with a change in modulation pattern of two lasers used as optical sources. For direct lock-in carrierographic imaging, both (or one) lasers are sinusoidally or square-waveform modulated using the data acquisition card (or 2 channel function generator). Synchronous undersampling with external triggering of the camera is implemented for lock-in in-phase (IP) and quadrature (Q) images. In this case $f_1=f_2$, $\Delta f=0$. As an example, 16 frames per correlation period are scanned and the number of skipping cycles is chosen as a function of the modulation frequency.

FIG. 1(c) illustrates another example apparatus 300 for performing heterodyne lock-in carrierography in a non-imaging configuration, in which a point-by point scanned imaging and photocarrier radiometric (PCR) frequency-scan setup is shown. The setup consists two 830 nm diode lasers 310 and 312 (Model 561CS115/HS from MELLES GRIOT), one channel 3.1 MHz synthesized Function Generator 315 (Model DS335 from Stanford Research Systems), two channel function generator 320 (Agilent Pulse Function Arbitrary Generator 81150A from Agilent Technologies), single InGaAs diode detector 325 (model PDA400 from THORLABS) or camera, two paraboloidal mirrors 330 and 332 from THORLABS, long-pass filter 335 LP-1000 nm from Spectrogon to block the excitation laser beams from interfering with the InGaAs camera or single InGaAs detector, optical block with collimator and focusing lens 340, lock-in amplifier 350 (model 5210 from EG&G Princeton Applied Research), and motorized XYZ stage 360.

In the example apparatus shown in FIG. 1(c), the laser spot size can be decreased down to 100 μm, and the step size is variable from 25 μm. For point-by-point imaging scans, the InGaAs camera can be replaced with an InGaAs single-element detector, as described above. As an example, a semiconductor substrate or a device such as a solar cell is irradiated with a square-wave-modulated laser beam at fixed modulation frequency leading to high-frequency PCR direct or heterodyne lock-in images, or at fixed coordinate points leading to single-point PCR frequency scans. Software of spot-by-spot imaging and frequency scans was developed in MATLAB environment.

Figure 7:
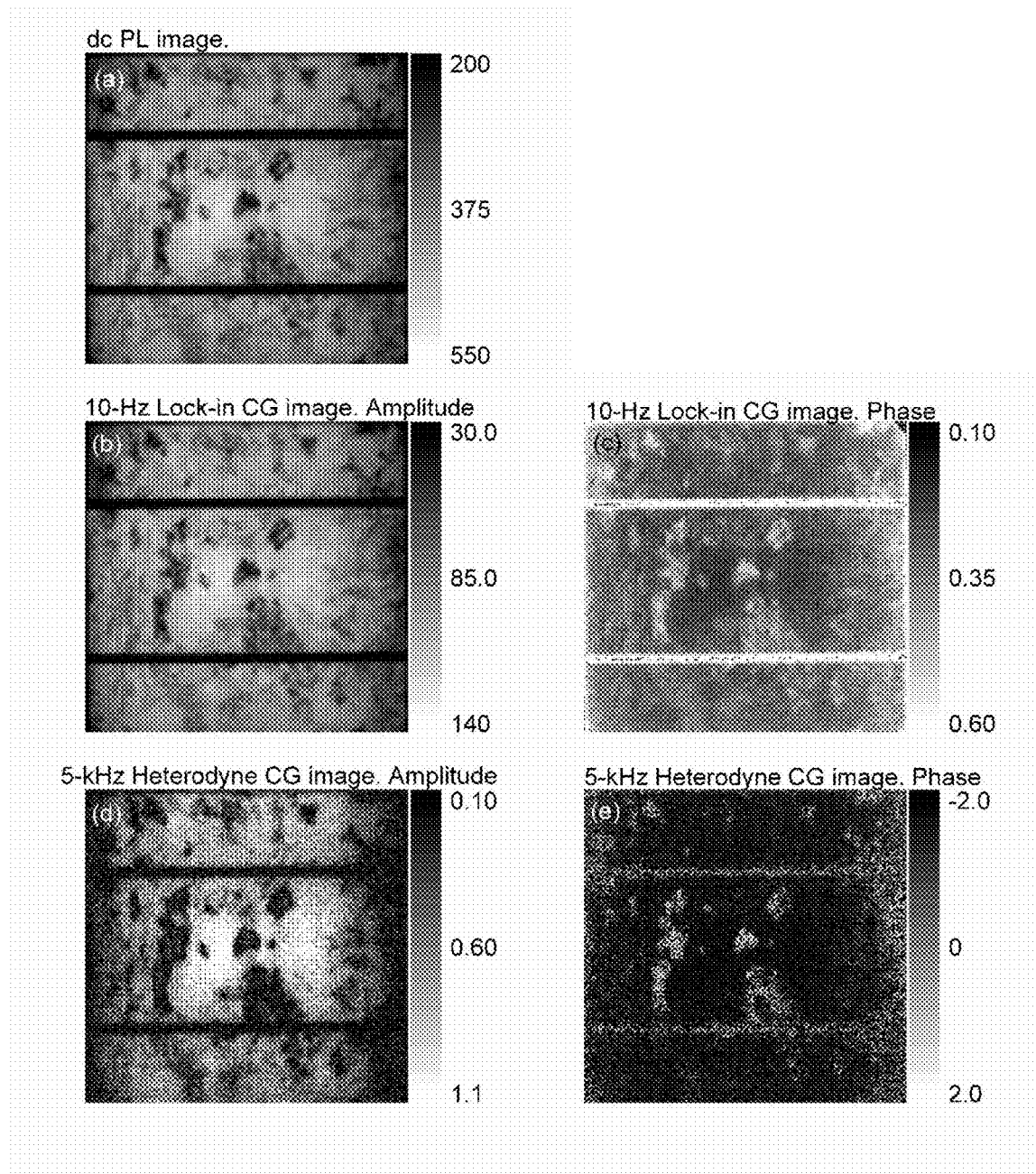
FIG. 7 shows images of (a) DC photoluminescence, (b) and (c) direct lock-in carrierography (f=10 Hz), and (d) and (e) heterodyne lock-in carrierography ($f_1$=5 kHz, Δf=10 Hz), of a 15.6×15.6 cm² multicrystalline Si solar cell (sinusoidal waveform modulation). In this and later figures depicting carrierographic images, no instrumental correction for phase images was made.

All images demonstrate the highly inhomogeneous spatial distribution of DC photoluminescence and both kinds of carrierography responses (low frequency direct lock-in and heterodyne lock-in). This inhomogeneity is caused by inhomogeneous transport properties in multicrystalline Si wafers as well as the quality of p-n junction and metal contacts. High photocarrier densities are usually associated with long recombination lifetimes. The DC photoluminescence image spatial resolution in FIG. 7(a) is limited by the long DC diffusion length, $L_{dc} = \sqrt{D^*\tau}$, of excess minority carriers. It is important to note that no significant differences are observed in the structures of DC photoluminescence and low-frequency lock-in PCR carrierography (FIG. 7(b, c)) up to 900 Hz. As expected, the HDC image shows higher contrast of solar cell optoelectronic inhomogeneities and more detailed features, FIG. 7(d, e). It also generates a phase image which carries additional depth resolved information and is largely independent of illuminations source spatial intensity fluctuations and anisotropy.

Figure 8:
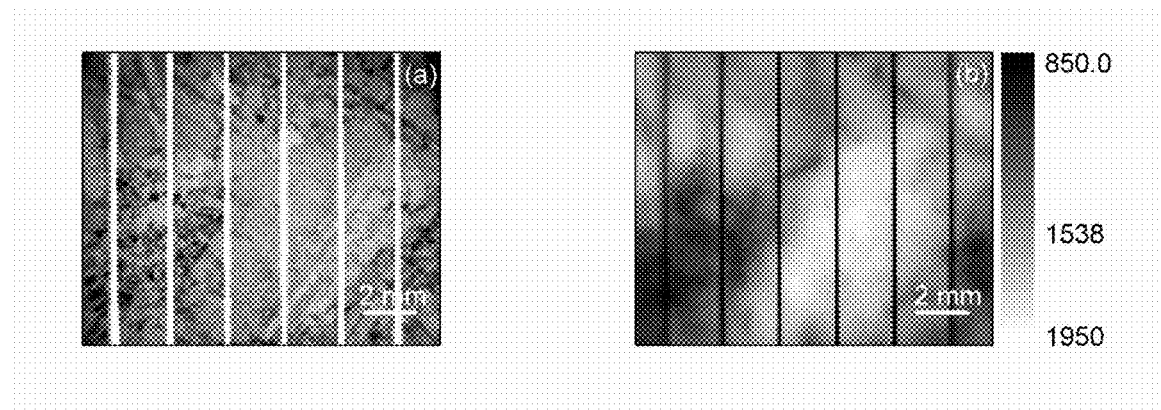
FIG. 8 provides (a) halogen-lamp illumination image of a region of interest in a mc-Si solar cell; and (b) DC photoluminescence image of the same region of interest illuminated with laser beam intensity 1.3 W/cm².
Figure 9:
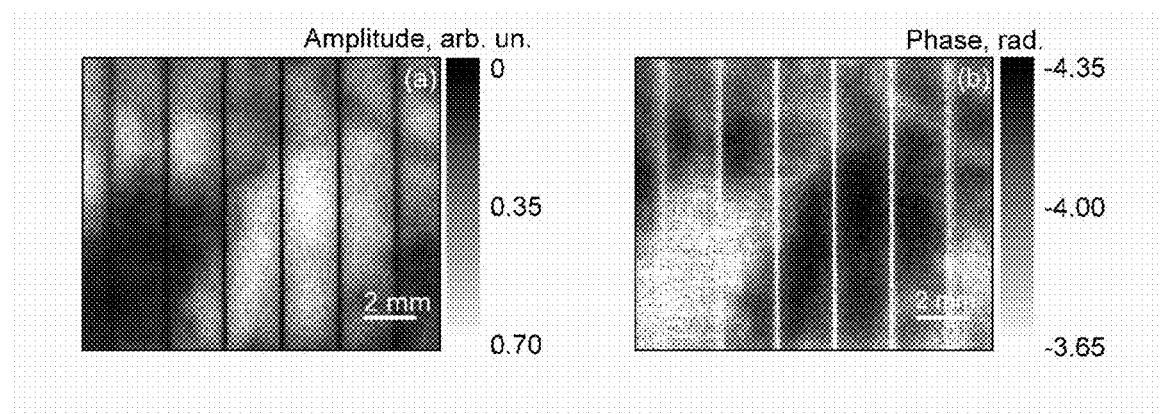
FIG. 9 shows direct lock-in carrierographic amplitude and phase images of the mc-Si solar cell region of interest in FIG. 8, with the InGaAs camera at exposure time 0.13 ms and laser beam intensity 1.3 W/cm²; modulation frequency: 900 Hz; (a) amplitude; (b) phase.

The NIR picture using a halogen lamp and the corresponding DC photoluminescence image of a small (1.4×1.2 cm$^2$) region of interest (ROI) in a mc-Si solar cell, both taken with the same InGaAs camera, are presented in FIG. 8. A grain-boundary-rich region of interest on the cell was chosen. From FIG. 8(b) it is possible to see that the spatial distribution of photoluminescence intensity is very inhomogeneous: high signal levels are closely linked to large crystallite formations visible in the halogen picture, FIG. 8(a), whereas low signals correspond to areas with small grains, large grain-boundary networks and defect areas with enhanced nonradiative recombination center concentrations. FIG. 9 is a higher frequency (900 Hz) lock-in carrierography image which reveals that there are significant numbers of highly electronically active "islands" interspersed within small-grain areas while retaining the broad amplitude features of the region of interest shown in the DC photoluminescence image. These highly active regions exhibit large phase lags (FIG. 9(b)), as expected from a deep reaching carrier density wave with long lifetime. Nevertheless, the exposure-time limitations, coupled with the low illumination intensity, tend to compromise the quality of the image due to the decreased SNR.

In order to overcome the severe frame-rate (undersampling) and exposure-time issues limiting direct high-frequency lock-in carrierography imaging, the present heterodyne scheme was introduced as described above. This scheme has the (stroboscopic) advantage of down-shifting the operating frequency into the range of the InGaAs camera capture capabilities even without undersampling, including setting the exposure time at the maximum value (16.6 ms) to yield optimum image SNR.

Figure 10:
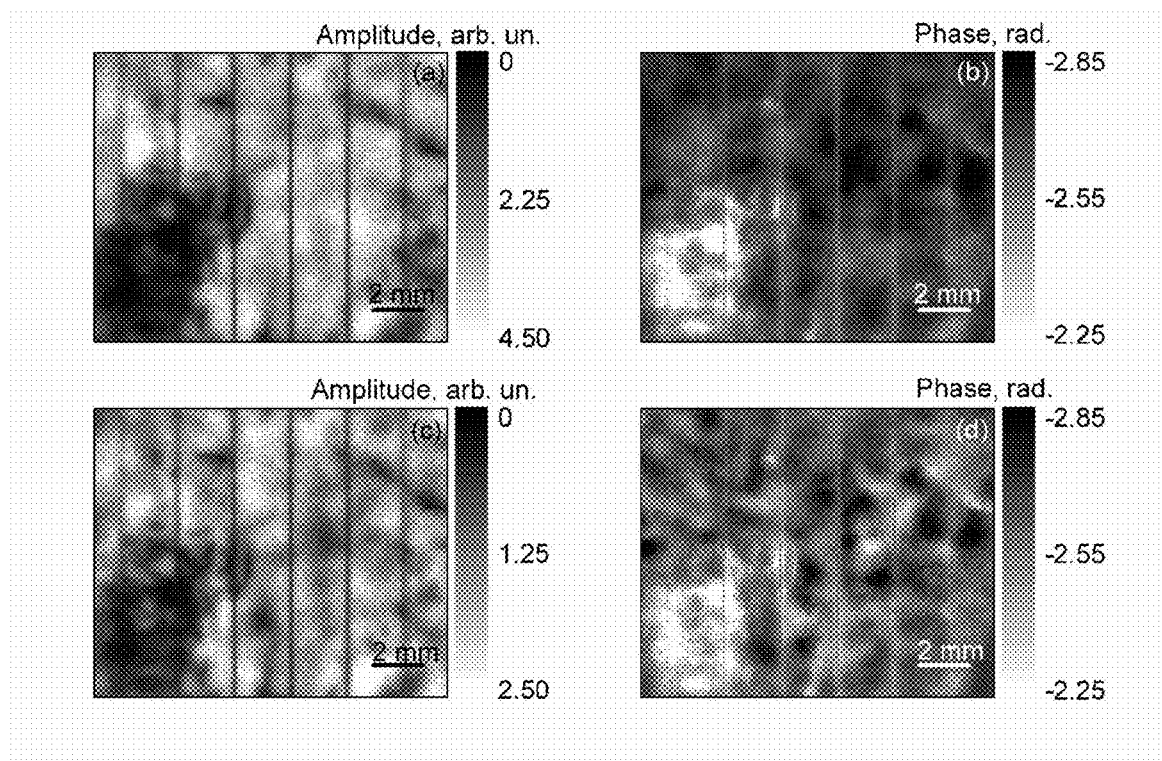
FIG. 10 shows heterodyne lock-in carrierography amplitude and phase images of the region of interest depicted in FIG. 8; (a, b): frequency $f_1$=5 kHz; and (c, d) $f_1$=10 kHz; beat frequency Δf=10 Hz; camera exposure time: 16.6 ms and beam intensity for both superposition lasers: 0.65 W/cm².
Figure 11:
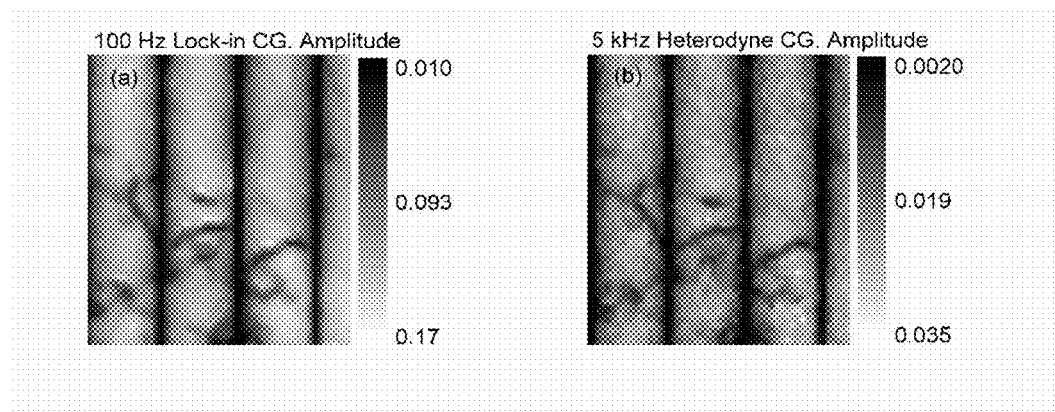
FIG. 11 provides (a) point-by-point direct lock-in carrierography images (f=100 Hz) and (b) point-by-point heterodyne lock-in carrierography images (h=5 kHz, Δf=100 Hz) of a multicrystalline Si solar cell fragment under a focused laser beam (spot size ~100 μm; square waveform modulation).

The lock-in heterodyne carrierographic amplitude and phase images at frequencies 5 and 10 kHz are presented in FIG. 10. Here spatial resolution has improved dramatically over both DC photoluminescence and low frequency lock-in carrierography and near-surface electronically active regions are delineated with sharp boundaries. They are effectively shrunk due to the high-frequency containment of lateral carrier diffusion. Considering that the higher frequency images represent a CDW depth distribution with carrier centroid [7] closer to the surface and to the active photovoltage generation region (junction), it is clear from the heterodyne amplitude images that the DC photoluminescence and low frequency lock-in amplitude shape are dominated by contributions deeper than the near surface region, which may not greatly affect the junction-localized photovoltaic energy conversion. The heterodyne amplitude image indicates that the very near surface optoelectronic activity is spread much more uniformly than amplitude images at lower frequencies and deeper contributions indicate. Note that there is little similarity between the DC photoluminescence and 10 kHz HDC images Similar results are observed in point-by-point imaging under a focused laser beam. The heterodyne lock-in image shows much more detail in spatial parameter distribution of a mc Si solar cell compared with the low frequency direct lock-in image (see FIG. 11). It is noted that the amplitude of the carrierographic signal significantly decreases in the direction of a grid line for both kinds of images compared to the carrierographic camera image. This is caused by the higher value of the local photovoltage due to the significant voltage drop on a series resistance.

Figure 13:
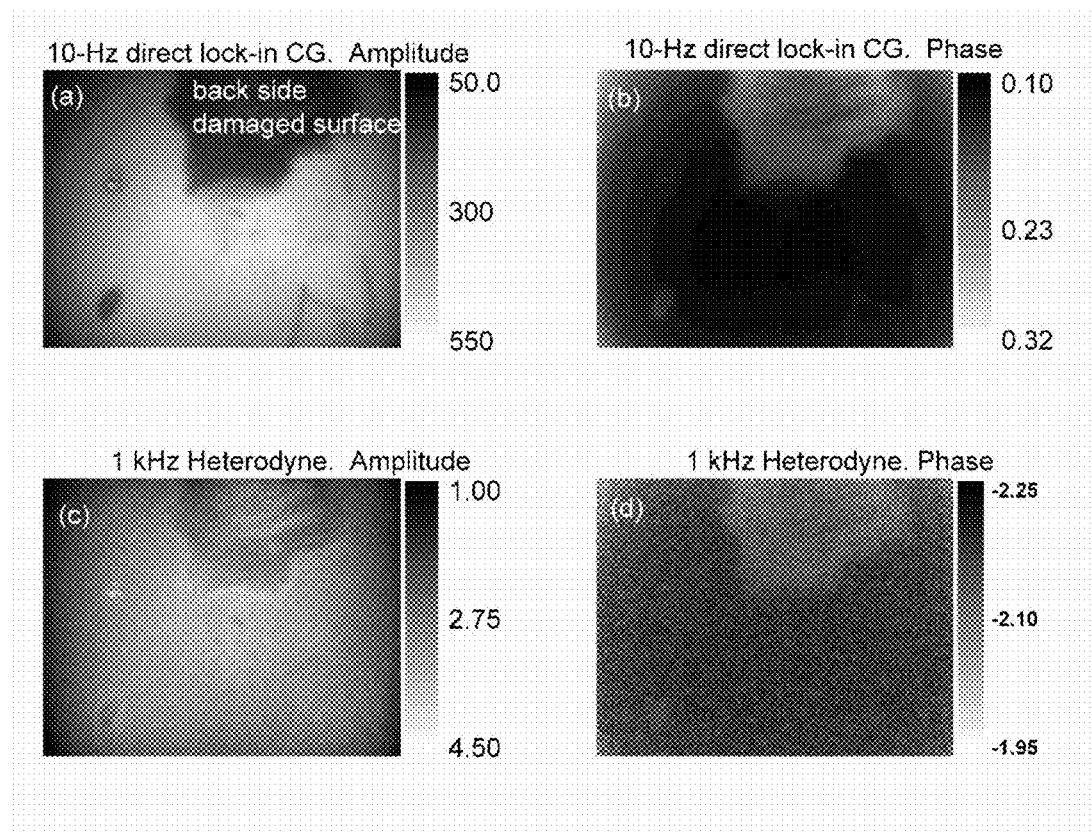
FIG. 13 shows amplitude and phase images obtained by (a,b) direct lock-in carrierography (f=10 Hz), and (c,d) heterodyne lock-in carrierography (f1=1 kHz, Δf=10 Hz) of a crystalline Si wafer with partial mechanical damage on the backside surface (sinusoidal waveform modulation, exposure time 8.3 ms).
Figure 14:
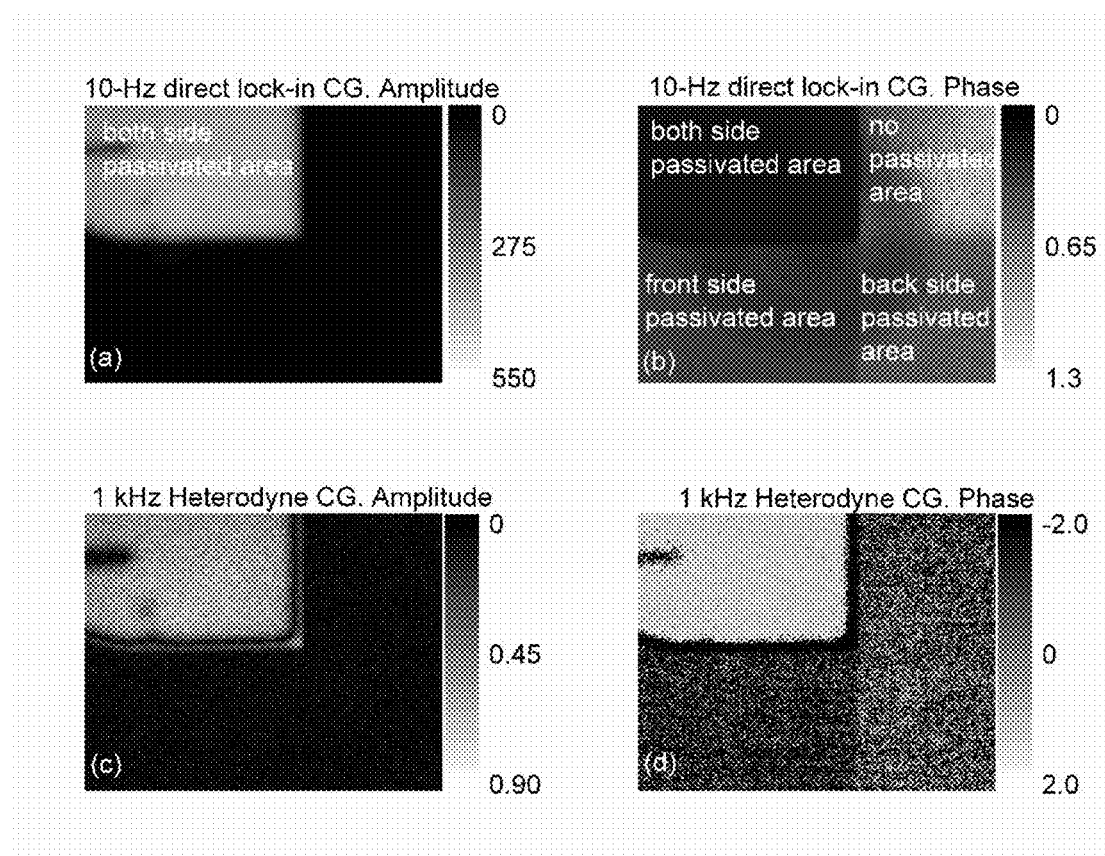
FIG. 14 shows amplitude and phase images obtained by (a,b) direct lock-in carrierography (f=10 Hz), and (c,d) heterodyne lock-in carrierography (f1=1 kHz, Δf=10 Hz) of a crystalline Si wafer passivated by amorphous i-Si (sinusoidal waveform modulation, exposure time 2.08 ms).

The direct lock-in and heterodyne lock-in carrierography images of some silicon wafers are shown in FIGS. 13 and 14. The structure of these images is similar to that of the solar cell (device) while in this case the p-n junction is absent. FIGS. 13,14 clearly show that the heterodyne carrierographic phase has a higher axial resolution than the amplitude, as it can resolve regions of different surface quality (surface recombination velocities). The 1-kHz images also show the CDW distribution in the front and near-front-surface region without the interference of back-surface effects which are evident in the 10-Hz image due to the longer AC carrier diffusion length.

Example 2

Figure 12:
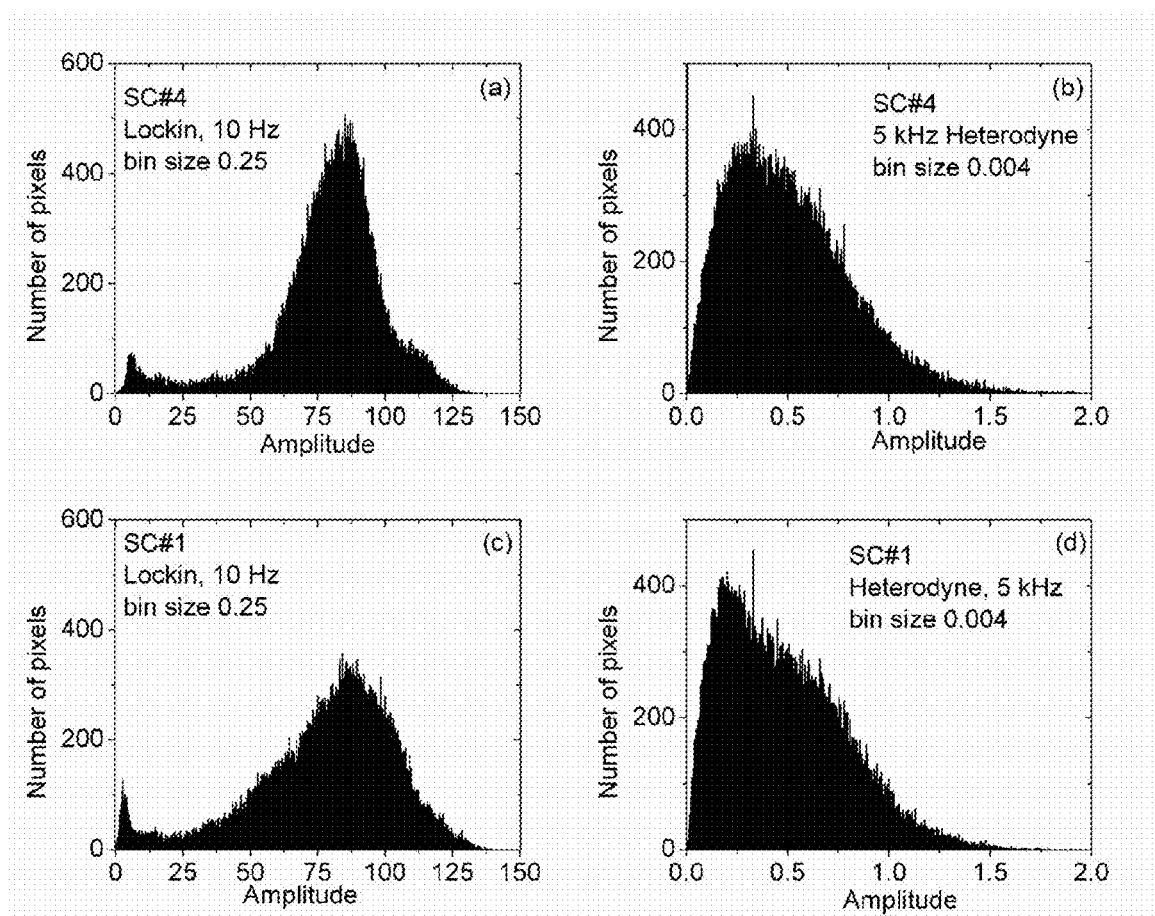
FIG. 12 plots statistical distributions of (a,c) direct and (b,d) heterodyne lock-in amplitudes of first (a,b) and second (c,d) mc Si solar cells (the second cell is shown in FIG. 7).

Statistical Optoelectronic Quality Monitoring Method Via Lock-in Heterodyne Carrierography Imaging Statistical distributions of direct and heterodyne lock-in amplitudes of two mc Si solar cells can be generated and are shown in FIG. 12. The statistical distribution was created by counting the number of pixels with amplitude within the range a and a+(bin size), that is proportional to the area of a solar cell or a substrate with pixel amplitudes within this range. The statistical distribution of the direct lock-in carrierography amplitude clearly shows the fraction of the area which does not generate photocurrent. This method of surface-integrated carrierographic amplitude (Sum of pixels) characterizes the optoelectronic quality of a solar cell. The statistical distribution heterodyne lock-in carrierography amplitude shows similar trends. However, the heterodyne carrierography images provide more features compared with the direct lock-in images as will be shown below.

Example 3

Figure 15:
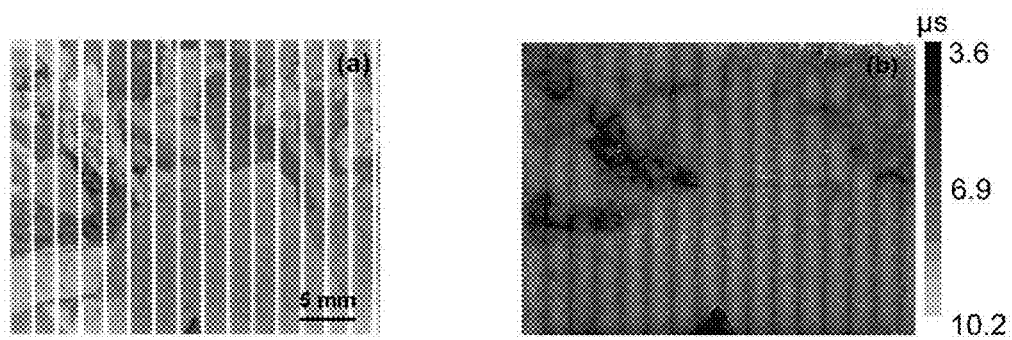
FIG. 15 provides (a) near-infrared optical image (halogen lamp illuminated picture) of a region of interest in a mc-Si solar cell, and (b) lifetime map of the same fragment of solar cell, measured with the μ-PCD method with 125-μm step using a 904-nm laser and 10 GHz microwave frequency.

Correlation Between Heterodyne Lock-in Image and Lifetime Map of MC Silicon Solar Cell It follows from the foregoing theory (Eqs. 9, 11, 23, 24, 29, 30) that the heterodyne signal depends on the transport parameters of a solar cell as well as the nonlinearity coefficient γ. The most important transport parameter is the bulk recombination lifetime. For experimental confirmation of this correlation, the same fragment of a solar cell (FIG. 15a) was measured with the help of a conventional technique: A map of recombination lifetimes was generated using the microwave reflectance PCD (μ-PCD) technique with a Semilab WT2000 system and is shown in FIG. 15).

Figure 16:
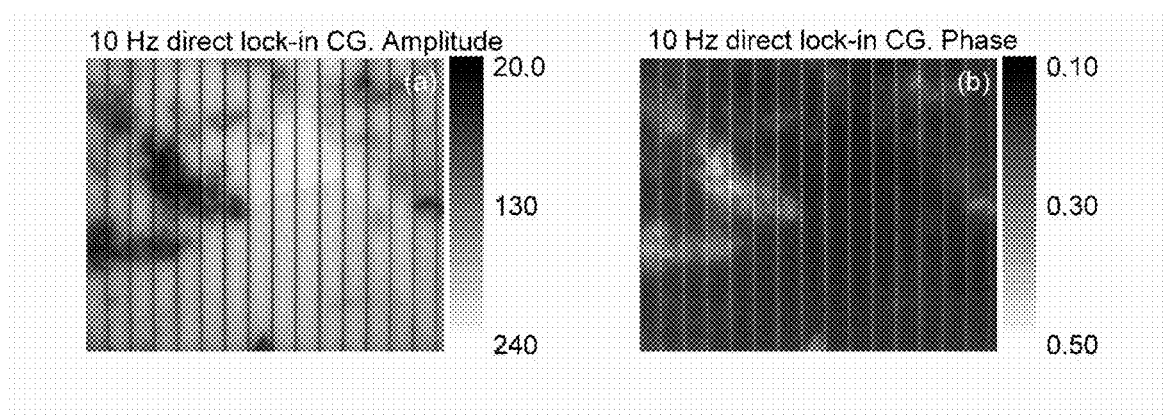
FIG. 16 plots direct lock-in camera carrierographic (a) amplitude and (b) phase images of the fragment mc-Si solar cell region of interest shown in FIG. 15 at 16-ms exposure time and 0.25 W/cm² laser beam intensity; modulation frequency: 10 Hz.
Figure 17:
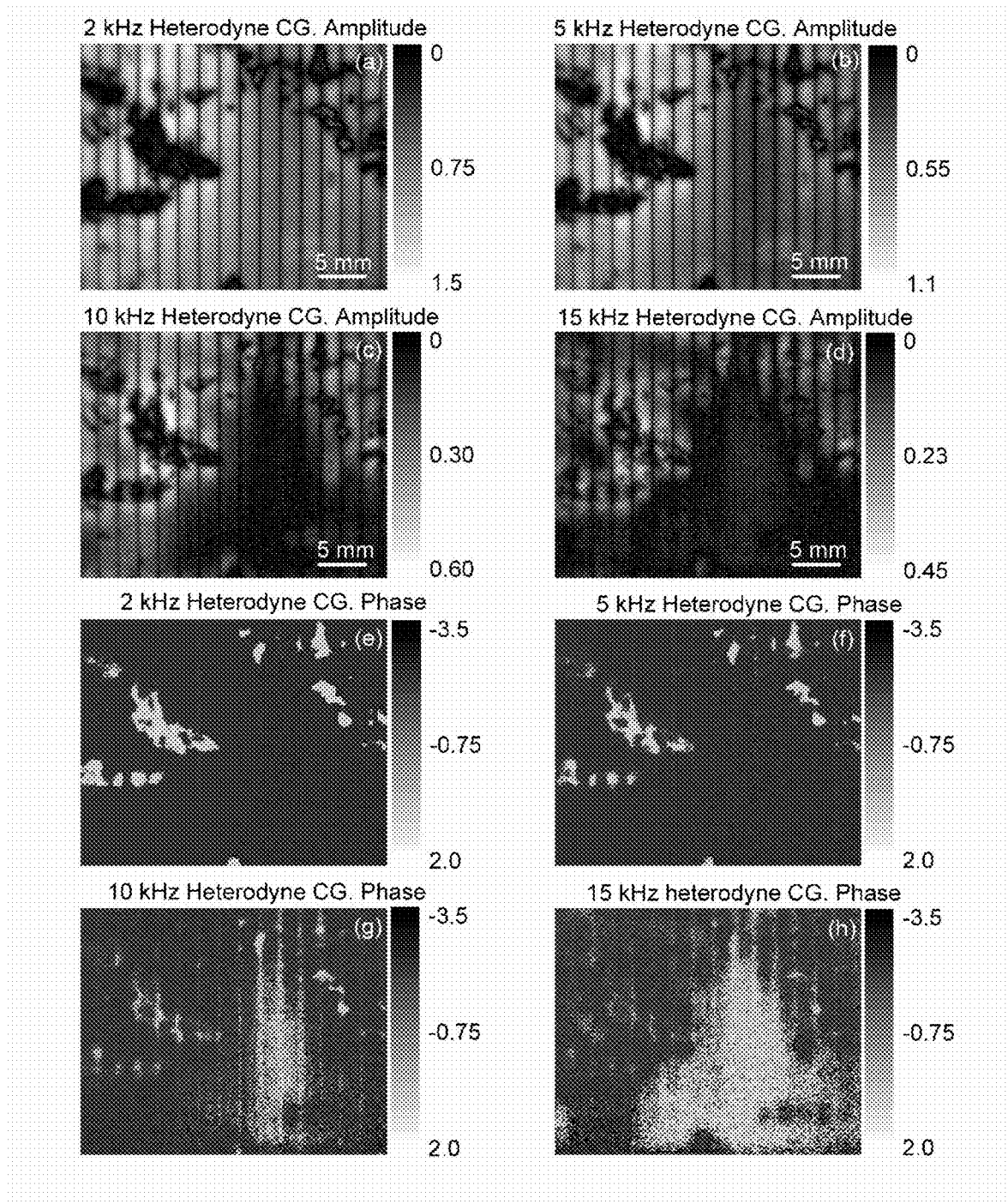
FIG. 17 shows heterodyne lock-in carrierography amplitude images of the solar cell depicted in FIG. 15(a): (a) frequency $f_1$=2 kHz, (b) $f_1$=5 kHz, (c) $f_1$=10 kHz, (d) $f_1$=15 kHz; and corresponding carrierography phase images (e), (f), (g), and (h); beat frequency Δf=10 Hz; camera exposure time: 16.6 ms and beam intensity for each superposition laser: 0.125 W/cm².

The 10-Hz direct lock-in and heterodyne lock-in carrierographic images of the same area are shown in FIG. 16 and FIG. 17, respectively.

It is seen that lower-frequency carrierographic amplitude images correlate with the lifetime map. Areas with higher amplitude correspond to areas with higher recombination lifetime. The HDC images show higher resolution compared with low-frequency images, as expected. For f≥5 kHz the shallower low-optoelectronic activity regions appear to increase in size considerably. As a result, the 10 kHz FIG. 17c,g amplitude and phase appear very different from those of FIG. 16a,b. The areas with extremely low recombination lifetime show large deviations of the heterodyne phase. The observed suppression of the 10-kHz heterodyne amplitude in areas with high recombination bulk lifetime, FIG. 15, is the result of the hidden effects of surface recombination in the latter figure. It shows a) the inadequacy of today's DC and low-frequency imaging state-of-the-art methodologies and b) the value of high-frequency carrierography in characterizing the important near-surface optoelectronic quality of industrial silicon solar cells upon which the cell efficiency hinges.

Example 4

Figure 18:
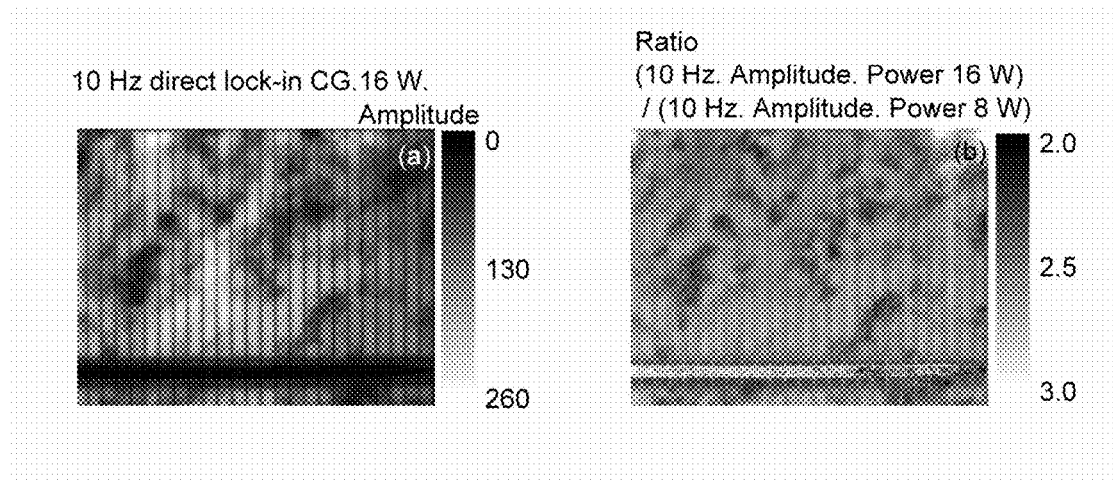
FIG. 18 plots (a) a direct 10-Hz lock-in carrierography amplitude image of a mc solar cell fragment at ~16 W laser power and (b) a ratio image of 10-Hz lock-in carrierography amplitude image at ~16 W laser power and 10-Hz lock-in carrierography amplitude image at ~8 W laser power; square waveform modulation.
Figure 19:
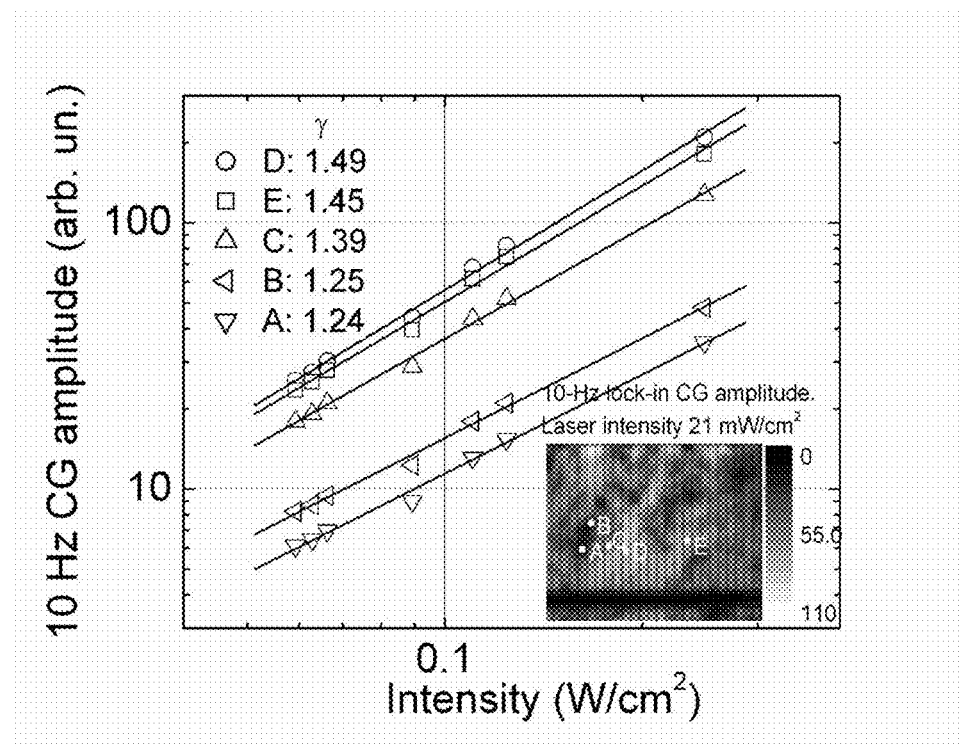
FIG. 19 plots the dependence of 10-Hz lock-in carrierography amplitude on laser beam intensity for various points on the carrierography image of the mc solar cell fragment of FIG. 18 with the non-linearity coefficient γ as a parameter; square waveform modulation.
Figure 20:
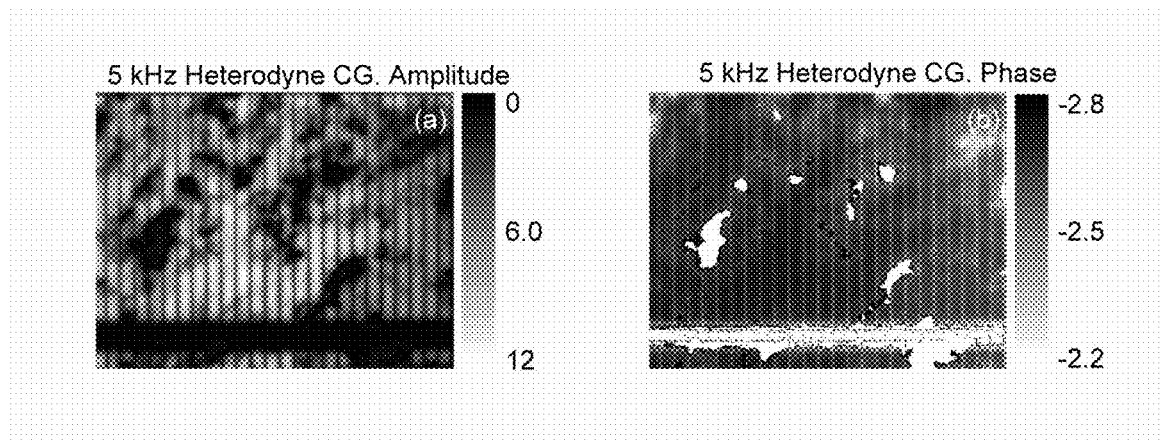
FIG. 20 shows 5 kHz heterodyne lock-in carrierography (a) amplitude and (b) phase images of the mc solar cell shown in FIG. 18; square waveform modulation.
Figure 21:
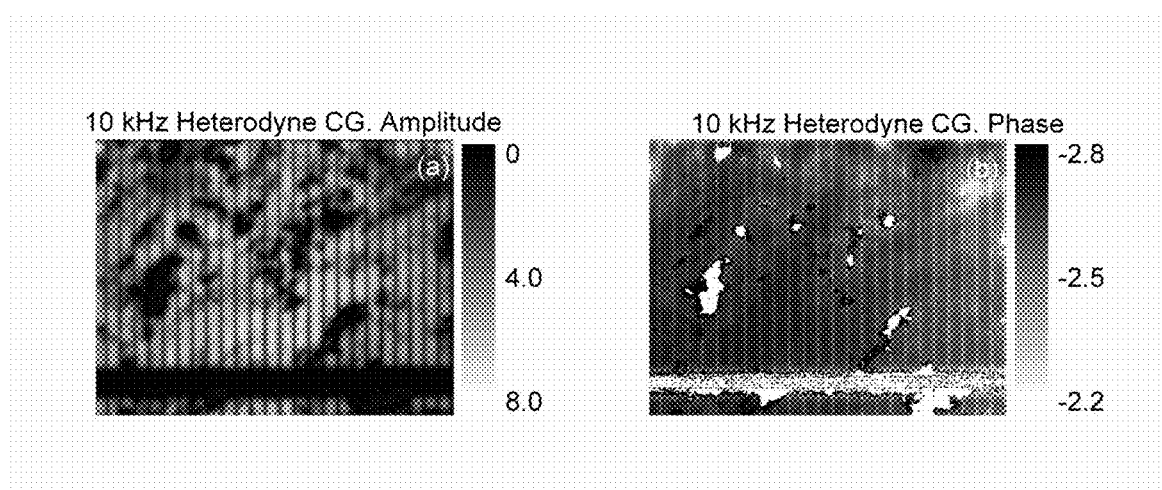
FIG. 21 shows 10-kHz heterodyne lock-in carrierography (a) amplitude and (b) phase images of the mc solar cell depicted in FIG. 18; square waveform modulation.

Influence of Non-Linearity on Heterodyne Lock-in Carrierography Signal of a MC Silicon Solar Cell Another important parameter, that strongly affects the heterodyne carrierography signal, is the non-linear nature of these signals. In the case of mc solar cells, where p and n layers are highly doped and there exist many defects (traps), the main source of non-linearity is likely to be the p-n junction. FIGS. 18 and 19 clearly demonstrate that different areas of a solar cell exhibit various degrees of non-linearity. The ratio of two CG images under different illumination intensity clear shows its inhomogeneity (FIG. 18b) that confirms various degrees of non-linearity along solar cell. It is important to note that areas with smaller lifetimes demonstrate a smaller degree of non-linearity. The ratio image is similar to heterodyne images of the same sample (FIGS. 20, 21). This demonstrates and motivates additional enhancing of contrast by heterodyne CG images.

The same features are observed in full solar-cell area images. It is observed that full solar-cell area images with small non-linearity coefficient γ are characterized by small heterodyne amplitude and small phase shift. It is important to note that square waveform modulation instead of sine waveform modulation leads to increased signal amplitudes and SNR without qualitative changes in image structures and frequency dependencies.

In conclusion, high-frequency non-linear heterodyne carrierography images and their dependence on transport parameters (mainly bulk lifetime and surface recombination velocity) in a non-linear manner exhibit enhanced contrast and resolution display of optoelectronic inhomogeneity areas compared with low frequency LIC.

Example 5

Figure 22:
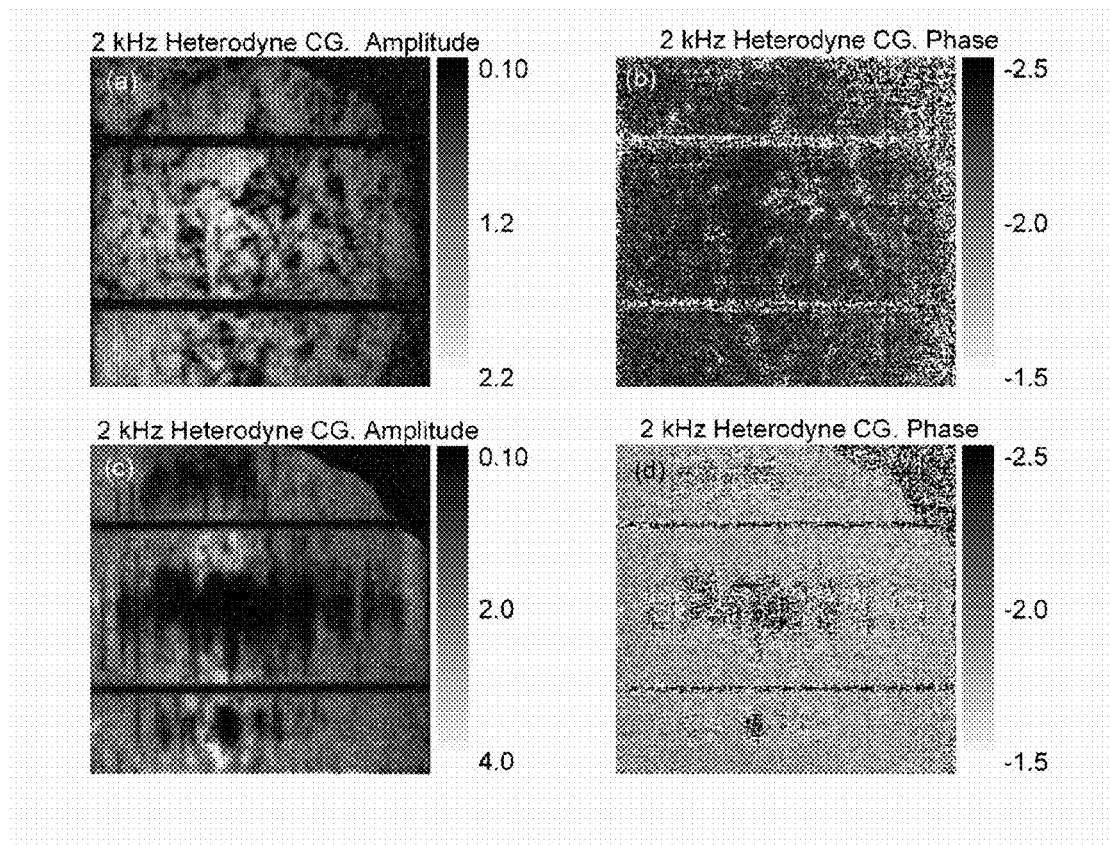
FIG. 22 provides 2-kHz heterodyne lock-in carrierography (a,c) amplitude and (b,d) phase images of a mc solar cell before and after mechanical treatment; sine waveform modulation.

Influence of Surface Damage on the Heterodyne Lock-in Image a of MC Silicon Solar Cell Surface damage of a mc silicon solar was induced by sequential rubbing with sand paper. Surface rubbing leads to increased front surface recombination velocity as well as damage to the p-n junction. As a result, the I-V characteristic was changed and the solar cell efficiency decreased. The voltage on the solar cell could be changed by means of a load resistance. The heterodyne lock-in carrierography images are presented in FIG. 22(a, b) before and FIG. 22(c, d) after mechanical treatment correspondingly. The damaged areas are clearly observed in the heterodyne image, FIG. 22(c, d). It is important to note that the heterodyne amplitude of the solar cell after mechanical treatment increases although the photovoltage decreases and therefore, the excess minority carrier concentration decreases, too. These opposite trends are probably caused by the changing non-linearity factor related to increased local resistance which forces photoexcited carriers to recombine locally, thereby enhancing the emitted recombination photon flux intercepted by the detector. The corresponding statistical distributions are presented in FIG. 23 and confirms this trend.

Figure 24:
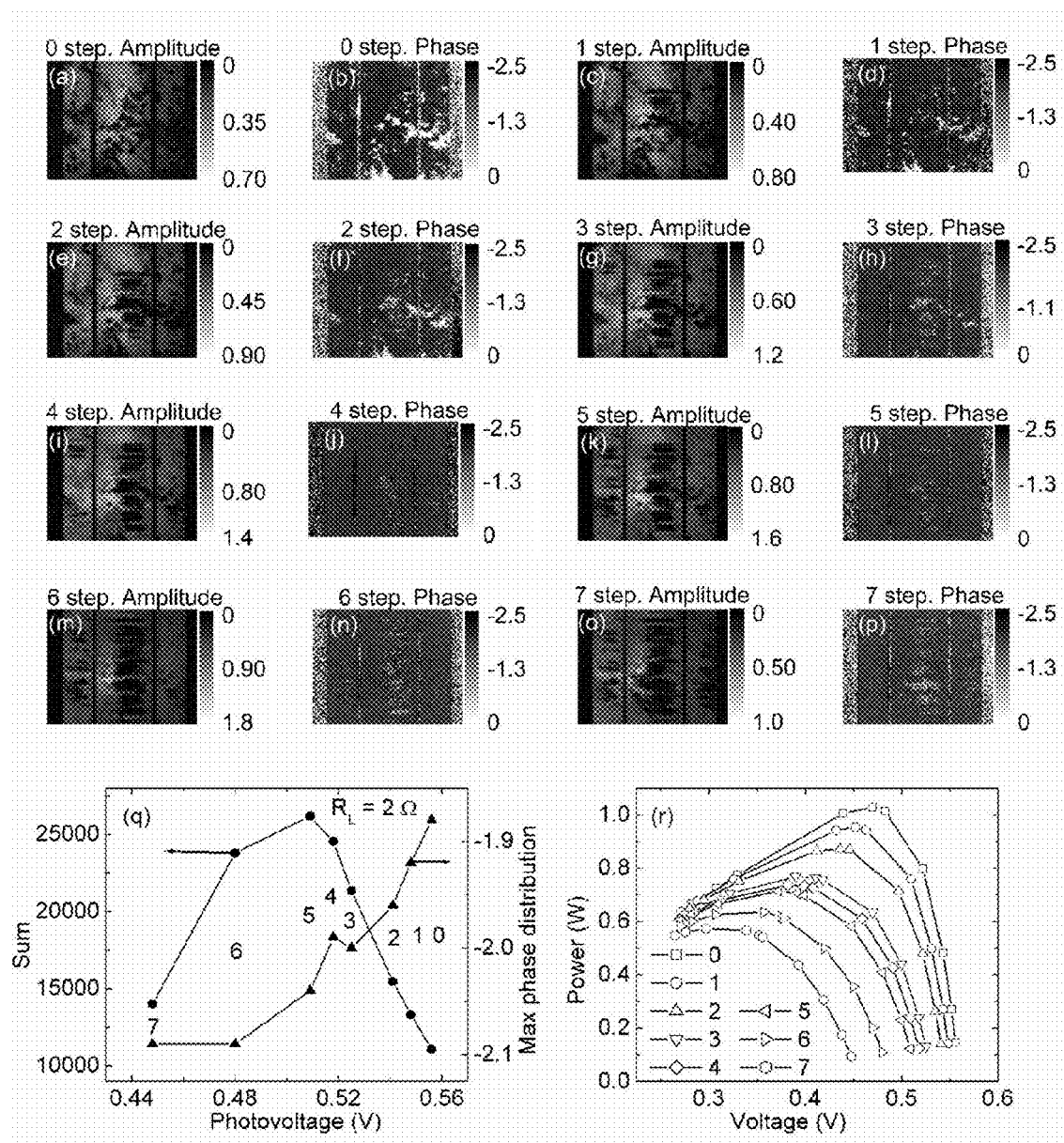
FIG. 24 plots 1-kHz heterodyne lock-in carrierography amplitude (a,c,e,g,i,k,m,o) and phase (b,d,f,h,j,l,n,p) images of a solar cell with sequential mechanical damage, under 2-Ω load resistance, (q) surface integrated amplitude and phase distribution maxima dependence on corresponding photovoltage; sine waveform modulation, and (r) correspondent power dependencies.

A more detailed evolution of heterodyne lock-in carrierography images with sequential mechanical surface damage is presented in FIG. 24(a-p). The major unexpected result is that the heterodyne amplitude increases after the onset of the mechanical damage and subsequently decreases after the appearance of large damaged areas. This may be the result of damage acting as a localization parameter and effective increased resistance of nearby photoexcited carriers. With increasing resistance photocarriers would tend to linger longer in the neighborhood of their creation, increasing the probability of a local recombination event and an increased radiative flux to the detector. This is accompanied by smaller phase lag in the region of damage, as expected, but the localization of photocarriers also becomes a recombination source within pre-existing nearby defect locations. Defect states in those locations tend to become occupied by recombined carriers and no longer act as trapping states, as shown in the sequence of the phase images FIG. 24. It leads to presence the pronounced peak in the surface integrated amplitude dependence vs. damage step corresponding photovoltage as shown in FIG. 24(q). While the correspondent phase distribution maxima dependence monotonically decreases with decreasing of photovoltage. The corresponding electrical characteristics of the solar cell during the damage process are shown in FIG. 24(r). The increasing of mechanical damage of surface leads to decreasing of photovoltage and maximum of power of solar cell and, as result, decreasing of efficiency.

Example 6

Figure 25:
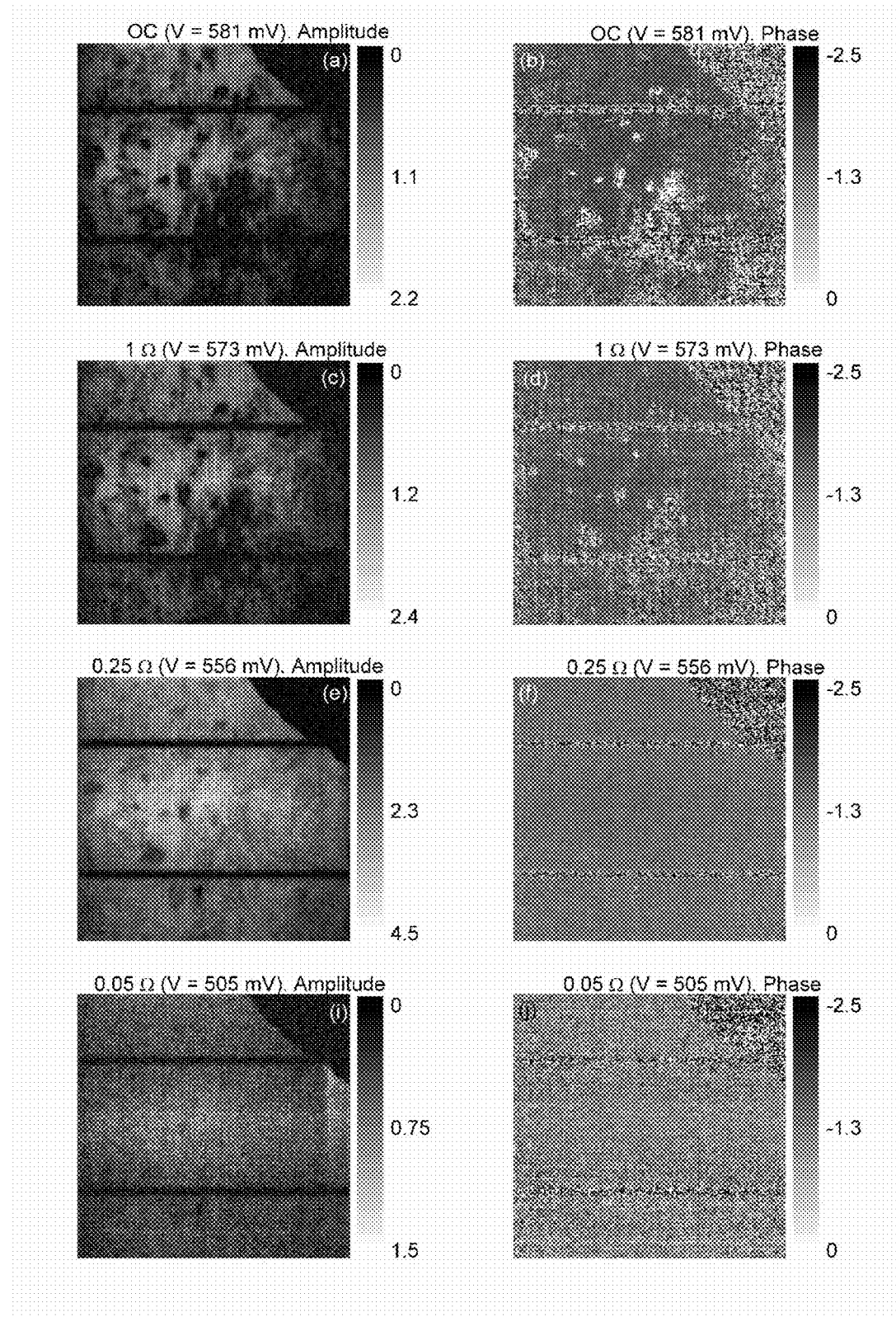
FIG. 25 shows 5-kHz heterodyne lock-in carrierography amplitude (a,c,e,g,i) and phase (b,d,f,h,j) images of a solar cell under various load resistances; sine wave form modulation.
Figure 26:
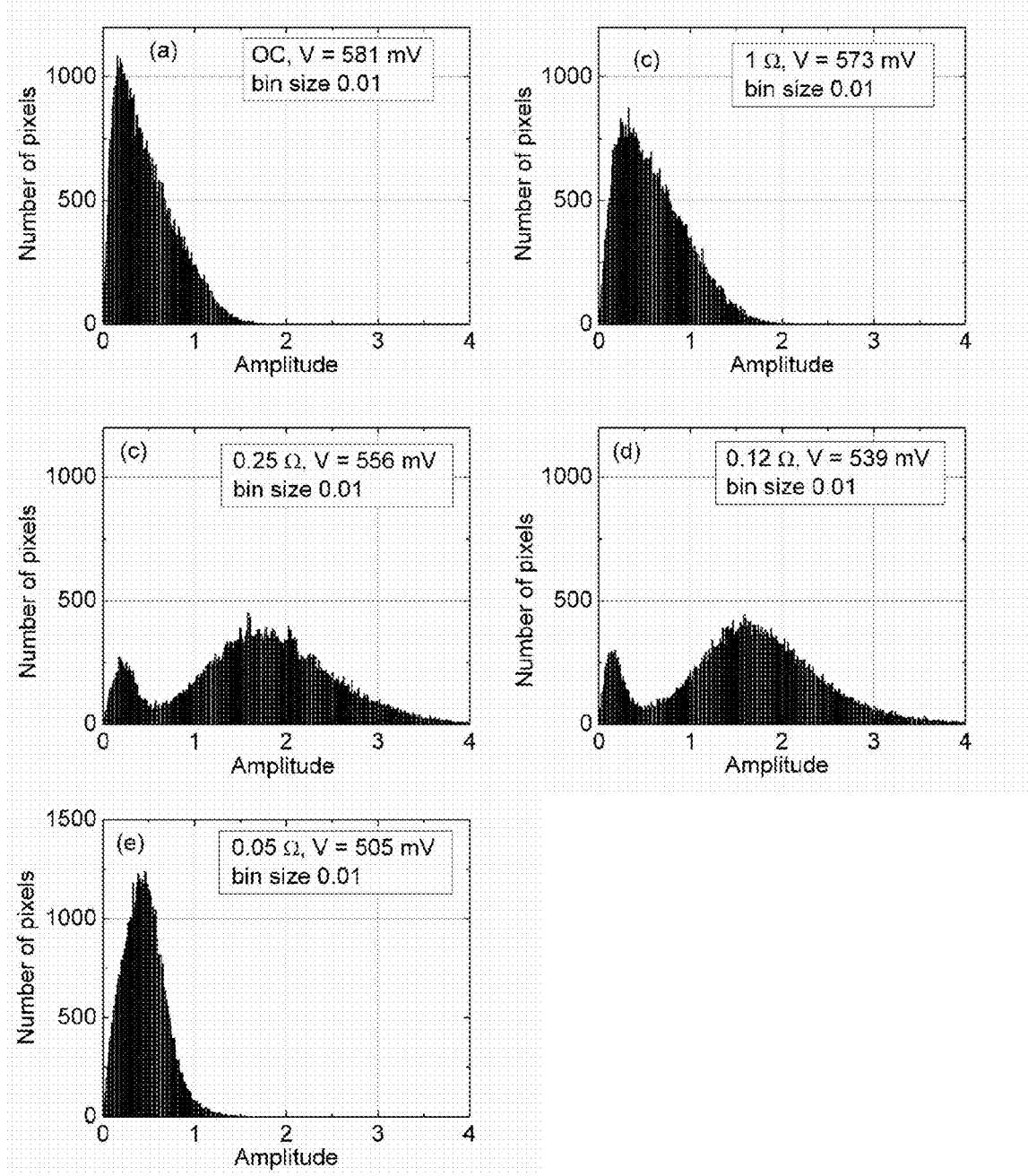
FIGS. 26 (a)-(e) show 5-kHz heterodyne lock-in carrierography amplitude statistics of the solar cell of FIG. 25 under various load resistances; sine waveform modulation.

Influence of Load Resistance on the Heterodyne Lock-in Image of a MC Silicon Solar Cell 5-kHz heterodyne lock-in carrierography images under various load resistances and the corresponding statistical distributions are shown in FIGS. 25 and 26, respectively. The signal amplitude increases with decreasing load resistance and decreases after reaching a maximum. These trends are probably caused by the same reasons as those described above in the case of the mechanically damaged solar cell. Under small load resistances (past the maximum CG amplitude) near short circuit, practically all the excess minority carriers move to the external circuit instead of generating photons at the location of the camera. This leads to significant decrease in the HDC image amplitude. The fact that CG amplitude increases with decreasing load resistance for values of the resistance from OC down to levels above that of the maximum CG amplitude, points to the effect the p-n junction lowering has to enhanced recombination of photocarriers transported over the decreasing potential barrier.

Figure 23:
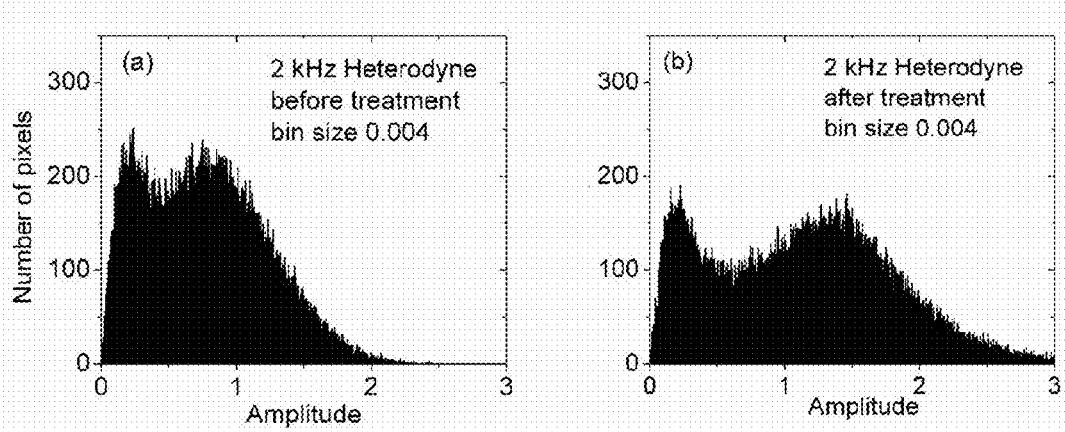
FIG. 23 plots statistical distributions of the mc Si solar cell heterodyne lock-in amplitude (a) before and (b) after mechanical treatment.
Figure 27:
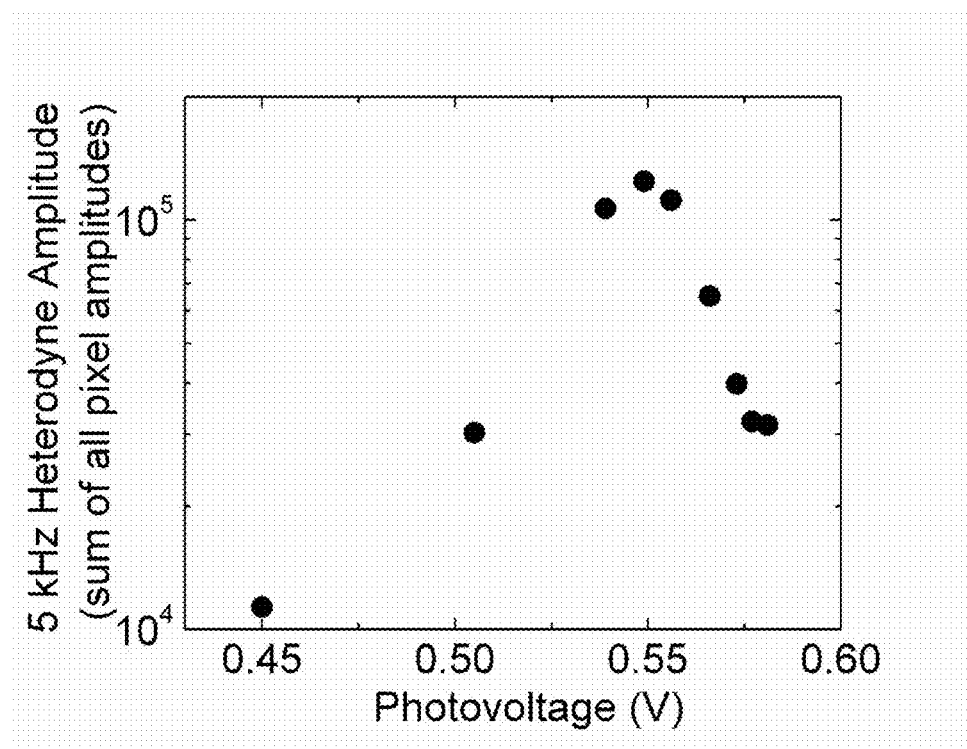
FIG. 27 plots the dependence of surface-integrated heterodyne carrierography amplitude on photovoltage under variable load resistance.

The dependence of the surface-integrated heterodyne carrierography amplitude of FIG. 26 on voltage, which in turn depends on the load resistance value, is shown in FIG. 27. This figure clearly shows the maximum active pixel voltage. A similarity between the trend in surface-integrated heterodyne carrierography amplitude upon decrease of load resistance and that of increasing mechanical damage, FIG. 23, shows the sensitivity of HDC to the shunt resistance.

Example 7

Applications of Lock-in Carrierographic Image Pixel Brightness Dependence on Multi-Crystalline Si Solar Cell Efficiency and Load Resistance In this example, the aforementioned methods of lock-in carrierographic image analysis of solar cells, based on the concept of non-equilibrium radiation chemical potential, are applied to the analysis of several multi-crystalline Si solar cells. The present methods may be employed for the analysis of heterodyne carrierographic lock-in images, and for the extraction of relevant device parameters based on statistical values.

Materials and Apparatus

Ten industrial multicrystalline solar cells (156×156 mm$^2$ area, 0.2 mm thickness) from Enfoton Solar Ltd., Cyprus, were used for LIC measurements. Subsequently, one solar cell was selected and sequentially damaged through gentle front-surface rubbing with fine sandpaper. Imaging measurements were made before and after each procedure.

A schematic of the LIC apparatus is shown in FIG. 1(b). The two lasers were used so as to attain sufficient optical flux over the full surface of our solar cells. The laser beams were spread and homogenized by engineered microlens arrays forming a square illumination area with intensity 0.04 W/cm$^2$ or 0.3 Suns (1 Sun=1353±21 W/m$^2$ [NASA value given in ASTM E 490-73a].

The system was reconfigured in such manner that a data acquisition module USB 6259 (from National Instruments) was used to generate sinusoidal waveforms for laser current modulation, as well as to trigger frame acquisition signals in the infrared camera from its digital I/O. The modulation frequency was set at 10 Hz. To acquire high signal-to-noise-ratio (SNR) lock-in in-phase and quadrature images, a 16× undersampling lock-in method was applied to the output image frames.

Results and Analysis

Equation (51) gives the LIC signal, $S_{CG}(\omega_M)$, in the one-dimensional carrier-density-wave approximation as a function of the radiative recombination efficiency. The proportionality constants C and K link the NIR detector/camera signal to the radiative emission process and can be consolidated as follows [5]:

$$S(\omega) \approx F(\lambda_1, \lambda_2) \int_0^L \Delta N^\gamma(z, \omega) dz \quad (80)$$

where the subscripts of $S_{CG}$ and $\omega_M$ are henceforth dropped for simplicity. F is a function of the spectral bandwidth ($\lambda_1$, $\lambda_2$) of the IR detector/camera and of the excess electron and hole carrier densities $\Delta N(z, \omega) \Delta P(z, \omega)$. Under nearly intrinsic and transport property conditions, this implies a quadratic dependence of the excess photocarrier density integrand ($\gamma=2$) [33]. The expected quadratic dependence is usually expressed as $B_{rad} \Delta N(z,\omega)[\Delta N(z,\omega)+N_D]$ as shown in Equation (62), where $N_D$ is the doping density. Under low injection conditions, however, the linear dependence on $\Delta N(z,\omega)$ dominates [5,34] and the LIC signals can be simplified with $\gamma=1$ which allows the integral in Equation (80) to be calculated analytically [5]. In many PCR situations the focused laser beam leads to intermediate injection conditions, or to recombination of free carriers not involving the conduction and valence bands (e.g. from band-to-impurity or band-to-defect), both of which can be modeled with $\gamma$ between 1 and 2 [20].

As discussed above, in addition to bulk-averaged recombination lifetimes which characterize DC PL image contrast, the spatial (lateral as well as depth) resolution and contrast of LIC images is due to variations in modulated CDW amplitude and phase which are controlled by the AC carrier diffusion length and its dependence on the local band-to-band and (or) band-to-defect decay lifetime $\tau$ within the diffusion length. Other transport properties generic to semiconductor optoelectronics [13] or to specific solar cell parameters (shunt resistance, series and load resistances, junction capacitance) also contribute to contrast.

Solar Cell LIC Image Pixel Brightness Distributions

Figure 28:
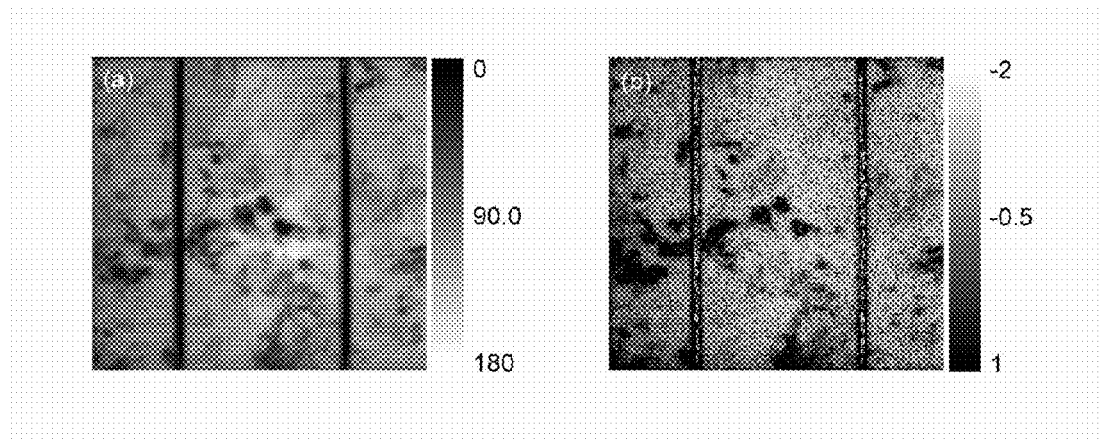
FIG. 28 provides LIC images of solar cell #8 at 10 Hz, showing (a) amplitude and (b) phase images.

The ten industrial solar cells labeled #1 to #10 were used for LIC measurements at room temperature at open circuit. LIC amplitude and phase images of #8 are shown in FIG. 28, in which the metal electrodes on the front surface of the sample appear as two vertical strips. FIG. 28(a) shows contrast due to a highly inhomogeneous distribution of radiative recombination processes across the solar cell, at the junction and mainly in the base of solar cell. The phase contrast in FIG. 28(b) is controlled by $L_e(\omega)$, Eq. (1), and is due to the phase lag contributed by depth variations of the CDW centroid [7] below the surface a function of the recombination lifetime $\tau$, and/or by the non-linearity exponent $\gamma$.

In some embodiments, phase images may be corrected for instrumental phase shifts which, unless accounted for, lead to changes of absolute phase values. However, all relative image features remain unaltered with or without correction.

Figure 29:
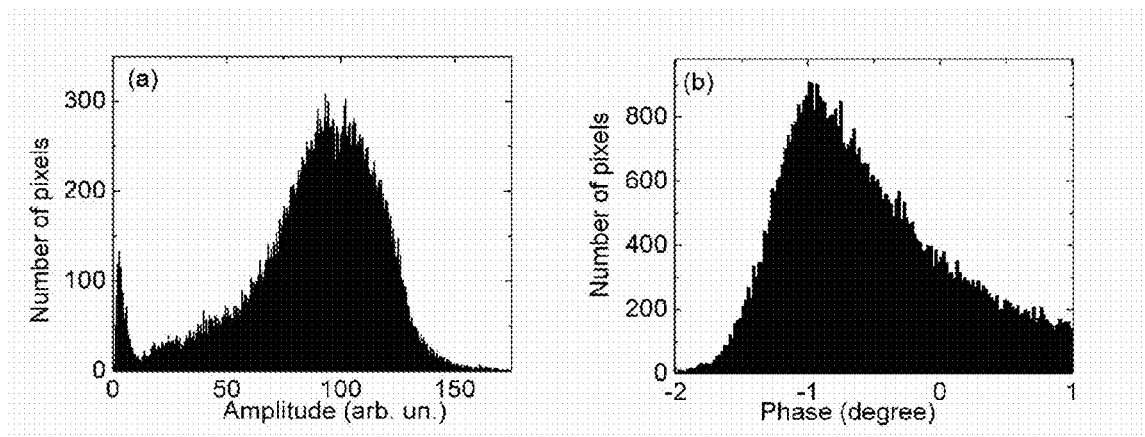
FIG. 29 plots the statistical pixel brightness distributions of LIC image (a) amplitudes with bin size 0.25 and (b) phases with bin size 0.002; of solar cell #8 obtained at 10 Hz.

Statistical histograms (camera pixel modulated brightness intensity distributions) over fully-illuminated surfaces were obtained from all LIC images for the purpose of validating the method described above with respect to quantitative dependencies of image pixel averages on solar conversion efficiency and photovoltage. The histograms show the number of pixels with amplitude (or phase) values within a range x and x+Δx (Δx: "bin size"). The number of pixels in Δx is proportional to the corresponding area of the solar cell so it describes the fraction of the solar cell surface with signal values within the given range. FIG. 29 shows a (typical) pair of LIC amplitude and phase histogram obtained from solar cell #8 using the images of FIGS. 28(a) and 28(b), respectively. The amplitude image histogram at 10 Hz is broadly peaked at approx. 100 (arbitrary units). The narrow amplitude peak at, or near, zero is due to very low pixel readings contributed from regions on, or near, the electrodes. The phase image histogram is peaked at ca. −1°. The longer tail on the left side of the amplitude histogram and on the right side of the phase is associated with contributions from solar cell areas with very low LIC amplitude. The statistical results of the LICG image pixel modulated brightness distributions from all ten solar cells obtained at 10 Hz are shown in Table 1.

TABLE 1

Electrical and LIC statistical parameters of the 10 solar cells.

| Name of solar cell | Electrical parameters ($J_i$ = 20.5 mW/cm$^2$) | | | | | Surface-averaged LIC amplitude | LIC phase |
| --- | --- | --- | --- | --- | --- | --- | --- |
| | $J_{sc}$ (mA/cm$^2$) | $J_0$ (nA/cm$^2$) | n | η (%) | $P_M$/S (mW/cm$^2$) | Sum (arb.un./cm$^2$) | Max (degree.) |
| #1  | 7.85 | 1.550 | 1.41 | 16.6 | 3.398 | 21.2 × 10$^3$ | −0.79 |
| #2  | 8.04 | 1.709 | 1.42 | 17.1 | 3.497 | 27.3 × 10$^3$ | −0.55 |
| #3  | 7.91 | 1.583 | 1.41 | 16.6 | 3.411 | 21.2 × 10$^3$ | −0.61 |
| #4  | 7.91 | 1.914 | 1.43 | 16.6 | 3.416 | 20.9 × 10$^3$ | −0.87 |
| #5  | 7.92 | 1.511 | 1.41 | 16.8 | 3.44  | 20.1 × 10$^3$ | −0.67 |
| #6  | 7.88 | 1.224 | 1.39 | 16.8 | 3.437 | 21.3 × 10$^3$ | −0.90 |
| #7  | 7.93 | 1.109 | 1.38 | 16.9 | 3.466 | 25.1 × 10$^3$ | −0.93 |
| #8  | 8.09 | 1.74  | 1.42 | 17.2 | 3.519 | 24 × 10$^3$   | −0.96 |
| #9  | 8.36 | 1.76  | 1.41 | 17.7 | 3.63  | 31.5 × 10$^3$ | −0.97 |
| #10 | 8.2  | 1.68  | 1.38 | 17.4 | 3.56  | 23.8 × 10$^3$ | −0.68 |

Figure 30:
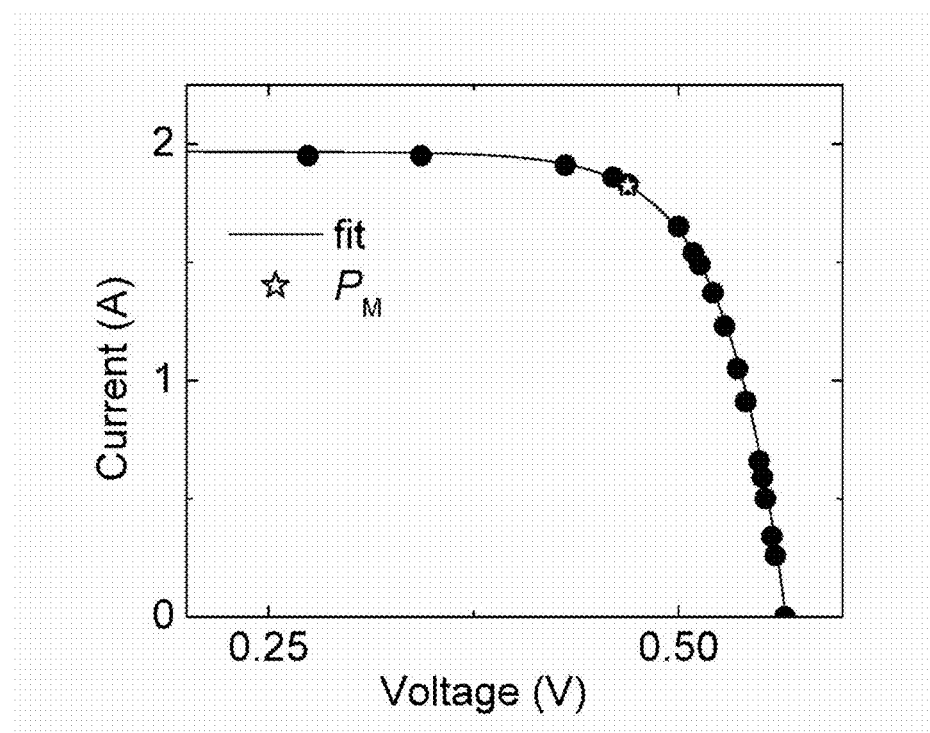
FIG. 30 plots I-V characteristics of solar cell #8; best-fit values: $J_{SC}$=8.096 mA/cm$^2$, $J_o$=1.740×10$^{-9}$ A/cm$^2$, n=1.422, $R_{sh}$=1000Ω; $\chi^2$=0.00027 and $R^2$=0.99945.
Figure 31:
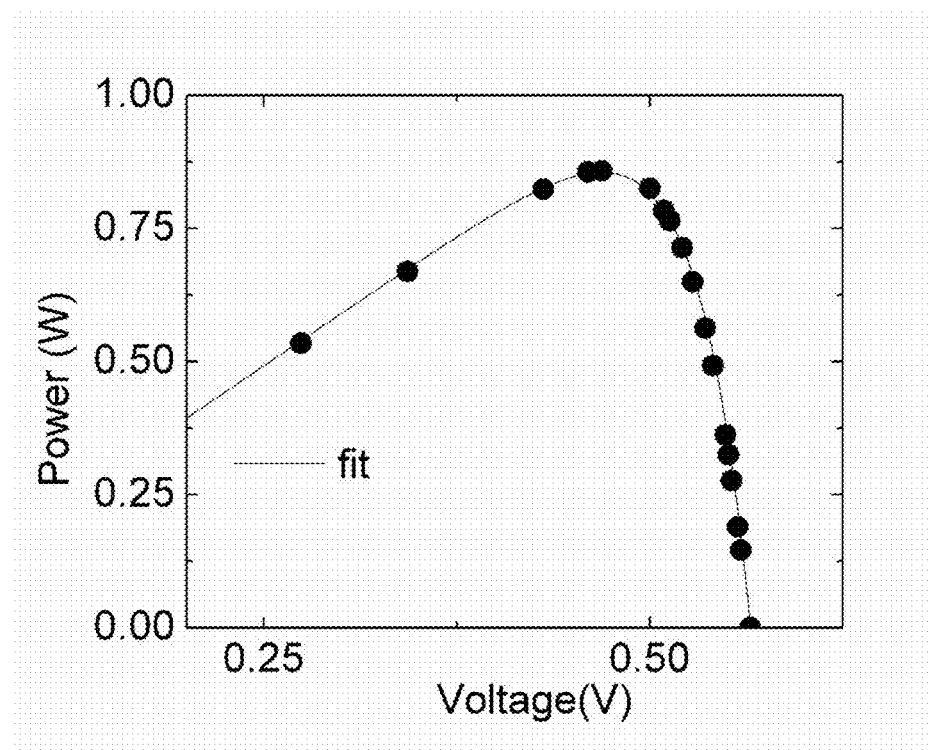
FIG. 31 plots the power vs. voltage curve for solar cell #8.

To calculate their solar conversion efficiencies, a load resistance box was used to measure the I-V characteristics with DC illumination provided by the two 808-nm diode lasers. The current I through the load resistance $R_L$ and the voltage V across $R_L$ were measured by changing the value of the resistive load. The experimental I-V characteristics of a solar cell were fitted to Equation (41) in the form I(V)=J(V)S (S: laser-beam illuminated solar cell surface area) which, however, does not take into account the series resistance in the solar cell. The values of $J_{SC}$, $J_0$, n and $R_{sh}$ were thus calculated for all cells. As an example, the I-V characteristics of solar cell #8 and the theoretical best fit are shown in FIG. 30. The maximum power, $P_M = V_{mp}I_{mp}$ [mW], was calculated from the voltage and current at the maximum power point, FIG. 37. Using the experimental $P_M$ values, the solar conversion efficiency was obtained from [35]:

$$\eta = \frac{P_M}{I_i \times S} \times 100\% \quad (82)$$

where $I_i$ is incident light irradiance [mW/cm$^2$] and S is the surface area of the solar cell [cm$^2$]. The calculated results in Table 1 show that the efficiencies of the ten solar cells ranged from 16.6% to 17.7%, values which are in agreement with those provided by the manufacturer. The table also includes the best-fitted values of the other electrical parameters of the solar cells, as well as the LIC results of the pixel histogram statistics. The parameter "Sum" is the sum of the amplitudes of all the pixels (excluding the pixels of the vertical dark strips corresponding to the front surface metal electrodes) divided by the area of the solar cell illuminated in the amplitude images. These are essentially numerical integrals of the distributions in FIG. 29 and correspond to the amplitude average of Equation (53) and a similar one for the mean phase surface integral implied in Equation (59).

Surface-Averaged η Dependence on LIC Image Pixel Brightness Distribution

Figure 32:
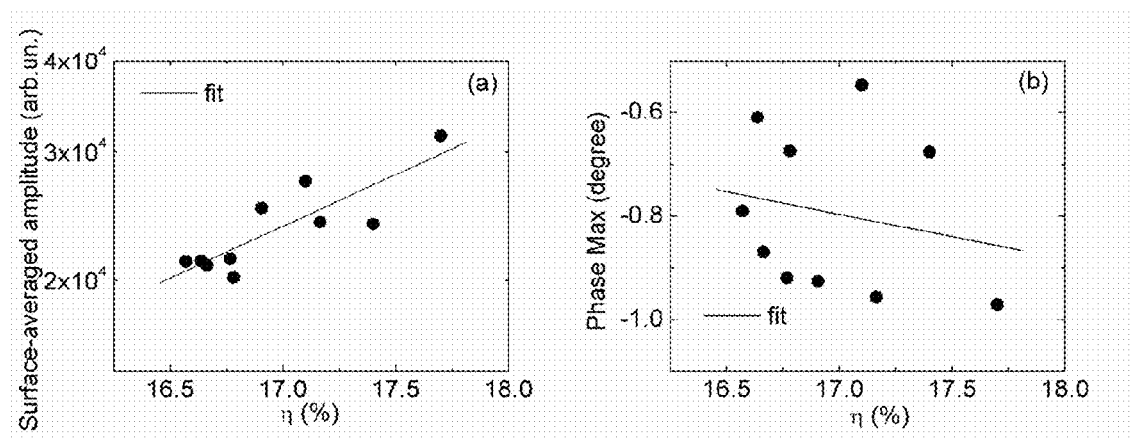
FIG. 32 plots the dependence of surface-averaged 10-Hz lock-in carrierographic (a) amplitude and (b) phase maximum distribution on the efficiency for 10 solar cells; best-fit slopes and intercepts are: amplitude 0.14 and 91, phase −0.087° and 0.68°, respectively.

The dependence of solar conversion efficiency and photovoltage on the full-surface pixel brightness statistical average was obtained for all solar cells under investigation, as the non-contacting lock-in carrierographic equivalent of the conventional electrical measurements averaged over a fully electroded solar cell surface. In view of equations (56) and (59) the plots of FIG. 32 were obtained in which solar conversion efficiencies are shown to be proportional to the Sum (logarithms) of the 10-Hz LIC amplitude images. The efficiencies are also seen to be linearly dependent on Max (phases). These results are in agreement with equations (26) and (30), respectively. The best fits to straight line shown in FIG. 32 yielded slope and intercept indicated in the caption of FIG. 32. It should be noted that, with typical Si solar-cell lifetimes τ normally ≤1 ms, at 10 Hz Equation (1) becomes $L_e(\omega) \approx \sqrt{D^*\tau}$. Therefore, the AC carrier diffusion length is equal to the DC carrier diffusion length which makes the LIC amplitude images exhibit the same features as their DC counterpart PL images.

However, LIC produces phase images as a second independent imaging channel, while the dark current in the camera pixels as well as noise and DC background are strongly suppressed in the lock-in method. The experimental results of FIG. 32a and additional PCR signal frequency measurements at several locations across the surface of the solar cells (not shown here) follow the general trends: Larger mean-value sum (amplitudes) correspond to higher solar conversion efficiencies and longer recombination lifetimes, as expected intuitively and concretely from the η proportionality to ΔJ, Equation (46a), with $\Delta J \equiv J_{SC} - J_{NR}$. High-optoelectronic-quality solar cells exhibit minimum $J_{NR}$ which maximizes η. Also, when the free-carrier-density wave which generates the CG signal is distributed closer to the surface (smaller phase lag), it can cross the electrode-semiconductor interface more efficiently and contribute to the solar cell electrical current density, resulting in a larger solar conversion efficiency η, as observed in FIG. 32b.

LIC Image Pixel Brightness Distribution Dependence on Surface Damage

To further investigate the applicability of the results of the statistical methodology theory to the non-contacting study of the solar conversion efficiency dependence on other device parameters shown in Equation (40) and its electrical counterpart, Equation (41), solar cell #2 was selected and sequentially front-surface-damaged 3 times through rubbing with fine sandpaper, followed by LIC imaging at 10 Hz. Moreover, the shunt resistance, $R_{sh}$, of the solar cell was also measured before and after each rubbing procedure. It was found that without damage $R_{sh}$ was 23.5 kΩ. After rubbing it changed to 0.80, 0.34, and 0.31 kΩ, sequentially.

The LIC pixel brightness amplitude distributions representing the rubbed area significantly shifted to lower values after the first rubbing and beyond. The results of mechanical damage are shown in FIGS. 33b-d. The pixel phase distributions are also significantly shifted to higher values for the same reason as that discussed in conjunction with FIG. 32, and shown in FIG. 34: Mechanical damage impedes the semiconductor-to-electrode charge transfer pathways, thereby diminishing or eliminating this carrier energy conversion venue, forcing the CDW to diffuse to deeper subsurface regions resulting in larger diffusion-wave centroid [7] mean phase lags, FIGS. 34b-d.

The $R_{sh}$ decreases recorded after each rubbing procedure are equivalent to non-radiative current density (energy decay pathways) increases, as follows from the comparison of equations (40) and (41). The worst damage images, FIGS. 33d and 34d, show that the decrease in radiative recombination events across the surface severely impacted image contrast. The large amplitude decreases due to the shift in recombination mechanism to non-radiative induced deteriorated image quality in both amplitude and phase channels. The contrast became so low that the damaged areas could not be distinguished with the intact parts of the surface while both regions exhibited compromised signal quality. This interesting lateral interaction effect may be due to the lateral diffusion and redistribution of photoexcited carriers: In isotropic high quality semiconductors large local carrier-wave densities diffuse spherically around their generation spot and in doing so they highlight contrast with neighboring low-quality regions, e.g., through rapid non-radiative decay mechanisms. As the high-quality locations become damaged, this lateral charge transfer decreases and ultimately ceases, resulting in poor or non-existent radiative recombination contrast even in the non-damaged regions.

Figure 33:
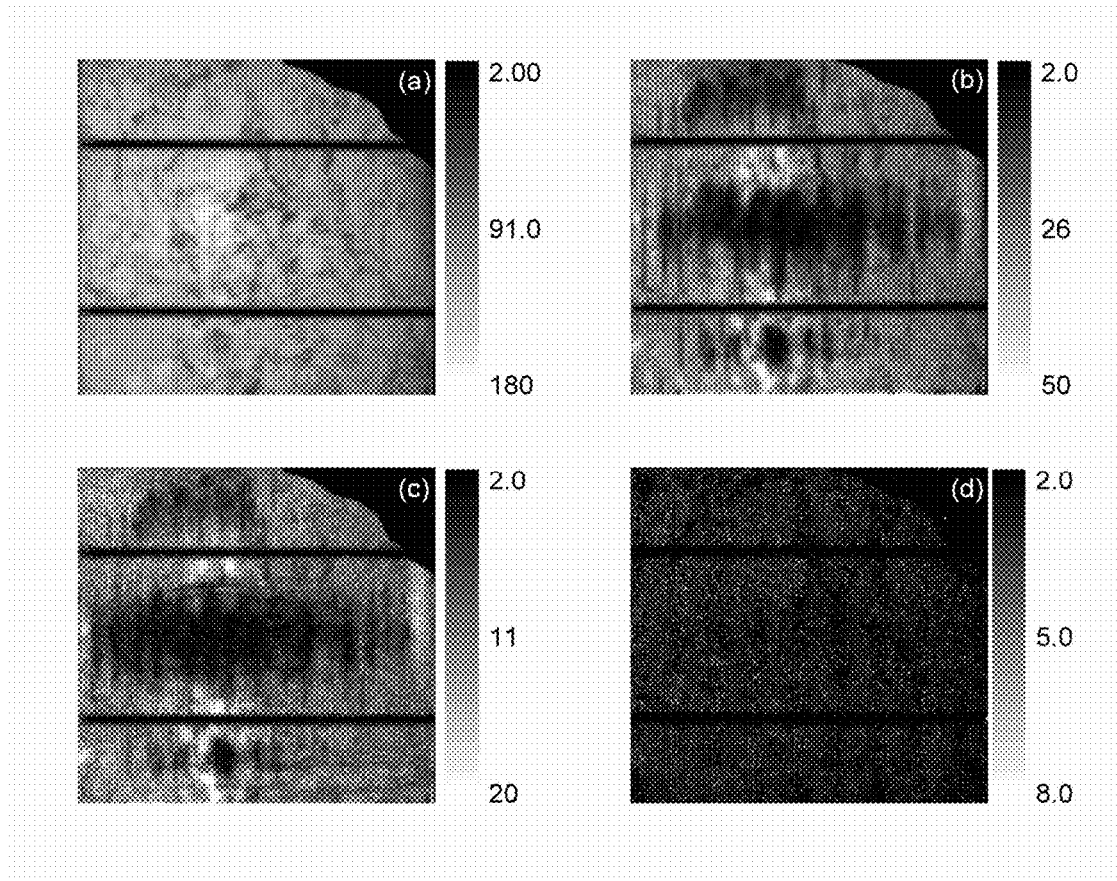
FIG. 33 provides LIC amplitude images of solar cell #2 before (a) and after (b-d) three rubbings with fine sandpaper imparting near-surface mechanical damage, exhibiting a monotonic amplitude distribution decrease.
Figure 34:
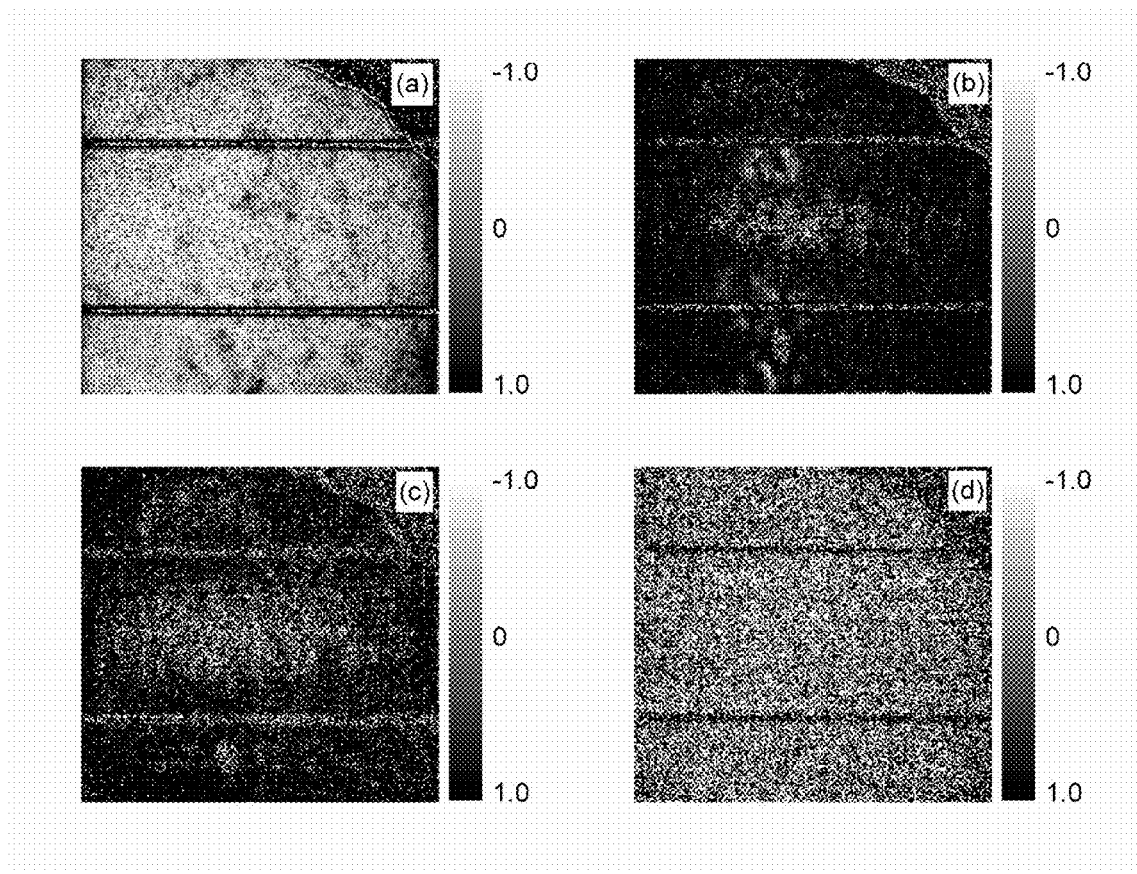
FIG. 34 plots LIC phase images of solar cell #2 before (a) and after (b-d) three rubbings with fine sandpaper imparting near-surface mechanical damage; exhibiting a monotonic phase distribution increase.
Figure 35:
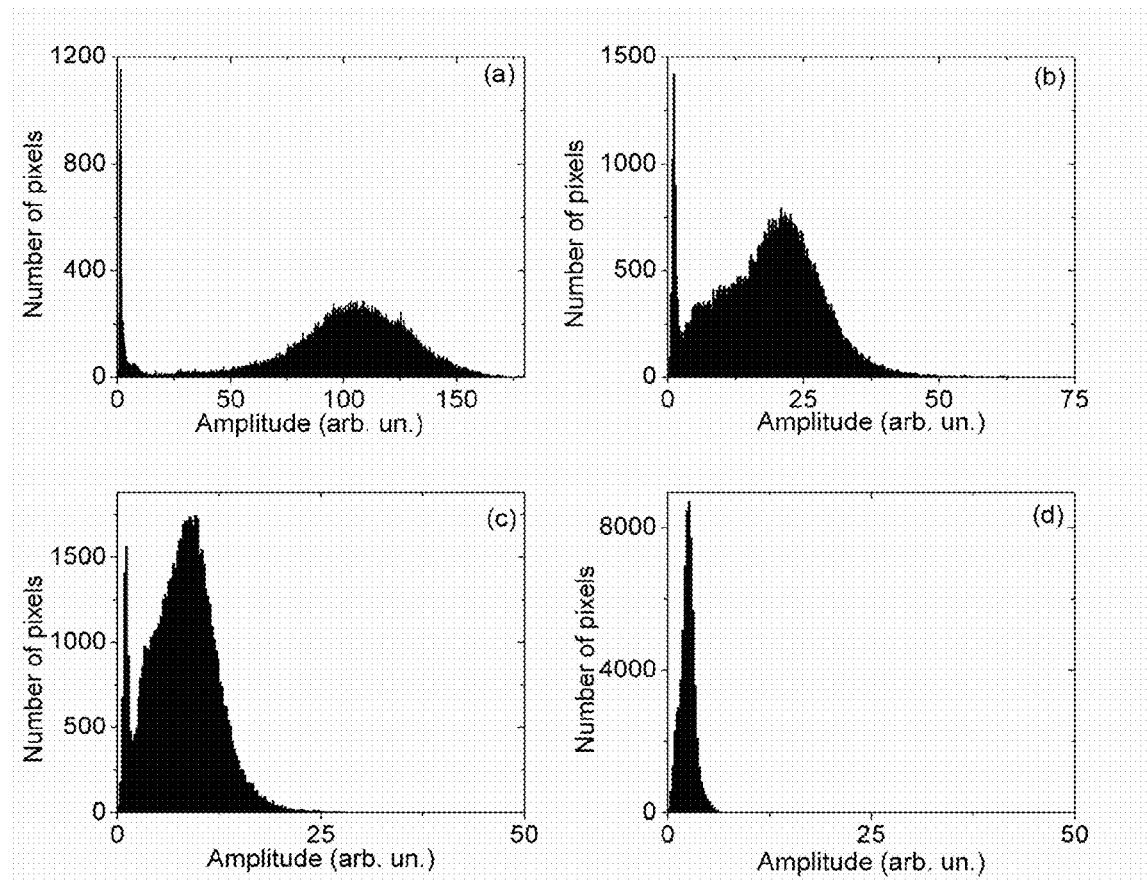
FIG. 35 plots statistical pixel brightness distributions of the amplitudes of the LIC images shown in FIG. 33.
Figure 36:
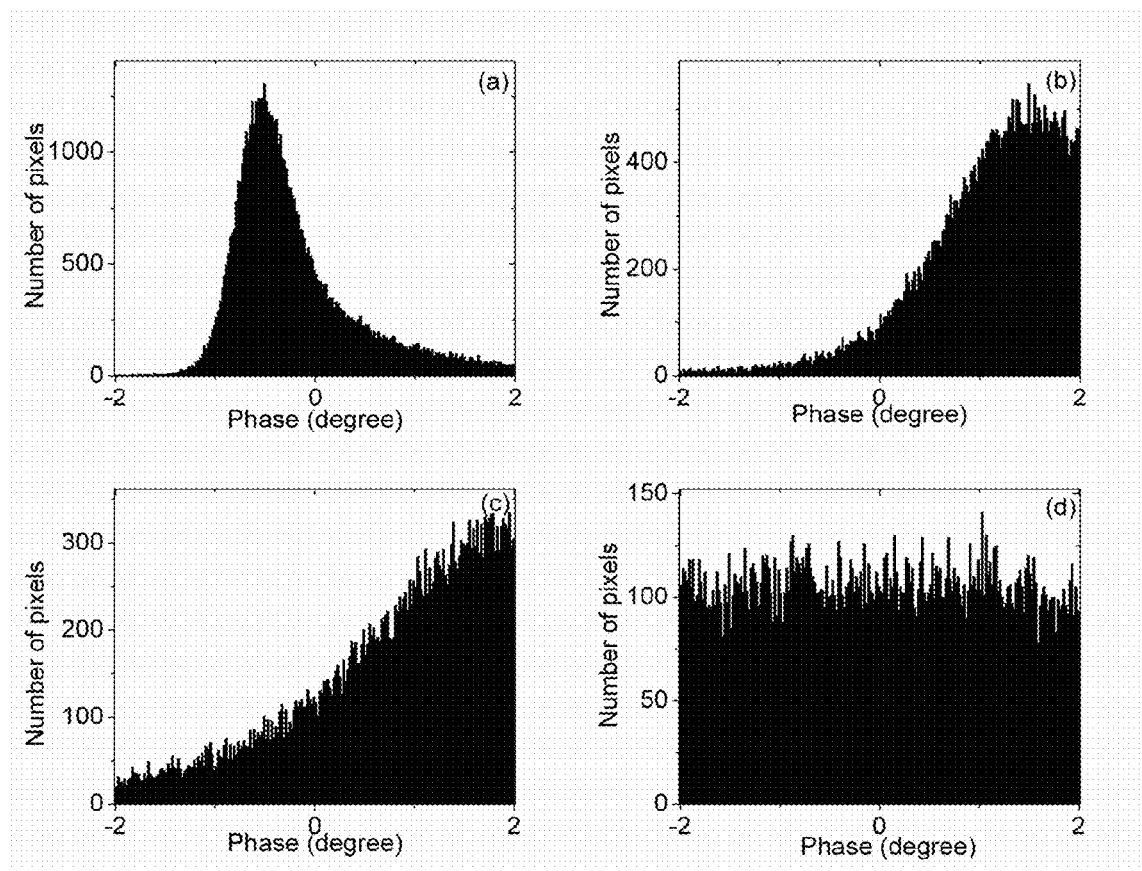
FIG. 36 plots statistical pixel brightness distributions of the phases of the LIC images shown in FIG. 34.

For quantitative purposes statistical pixel brightness distribution histograms were also constructed for all LIC amplitude and phase images shown in FIGS. 33 and 34. The results are shown in FIGS. 35 and 36, respectively. The amplitude histogram of solar cell #2 before damage is similar to that of #8, FIG. 29(a), except for a much higher peak of the left, which was contributed by a broken corner. The phase-image histogram also shows similarities to FIG. 29(b) without a spike at the origin, because the pixel phase distribution at the broken corner overlapped the lower phase range of the solar cell.

Figure 37:
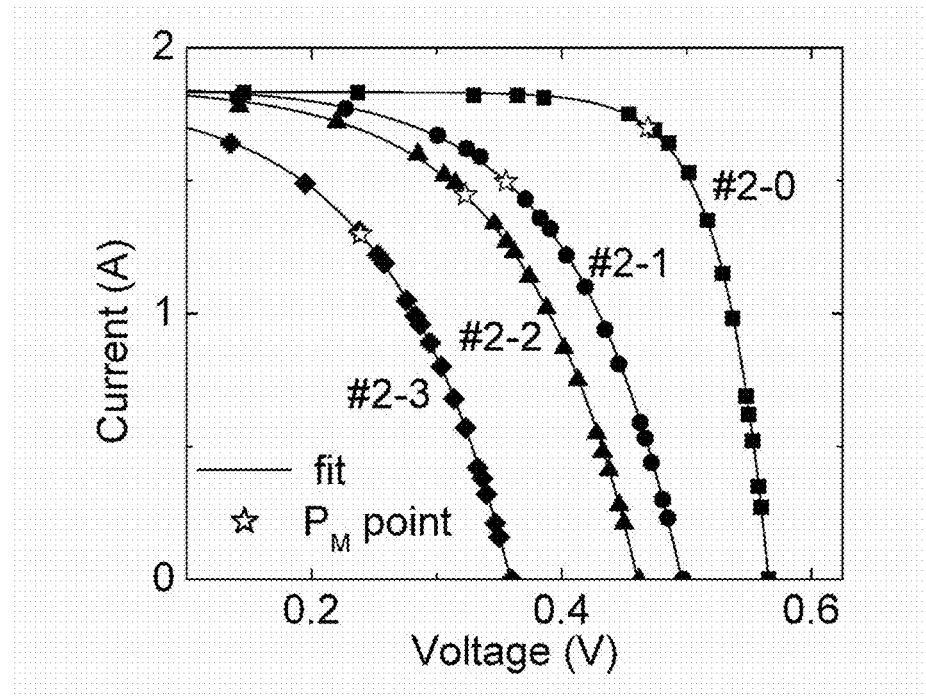
FIG. 37 plots I-V characteristics of solar cell #2 before (#2-0) and after (#2-1, #2-2, #2-3) three rubbings; S=228 cm$^2$.
Figure 38:
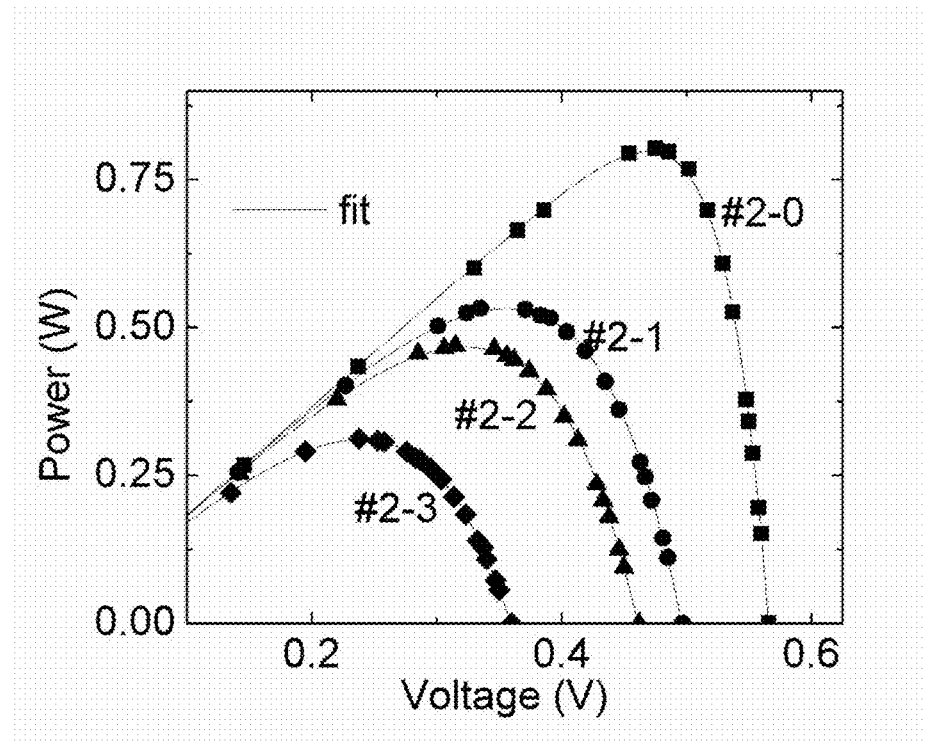
FIG. 38 plots power vs. voltage curves for solar cell #2; S=228 cm$^2$
Figure 39:
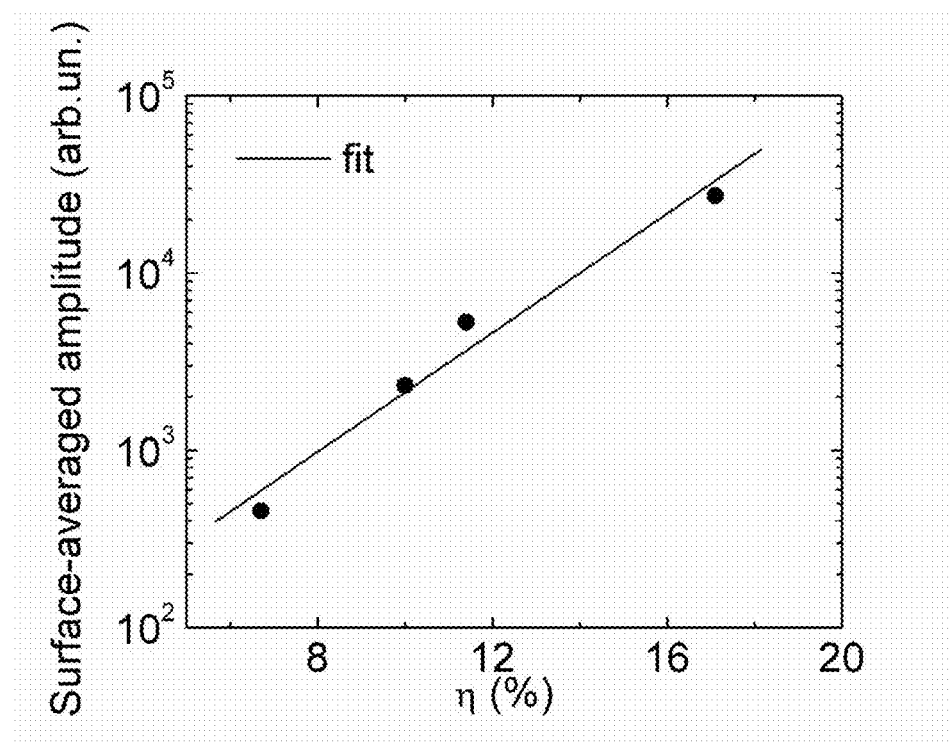
FIG. 39 plots the dependence of surface-averaged 10-Hz lock-in carrierographic amplitude on the solar conversion efficiency for surface damaged solar cell #2; best-fit slope and intercept is 0.17 and 44. Illumination power density: 0.041 W/cm$^2$.

After the first and second rubbings, with the exception of the near-zero contributions of the electrode and the broken corner, the main peak in the amplitude image significantly shifted to the left with the peak growing narrower and taller because the total pixel number remained fixed. After the third rubbing, the main peak in the amplitude image entirely overlapped the leftmost peak corresponding to the electrodes and the broken corner. The narrowness of this peak is a statistical manifestation of the fully deteriorated image contrast. On the contrary, in the pixel phase distribution, FIG. 36, the main peak shifted to the right (to larger phase values) in agreement with the imaging trends of FIG. 34. It is interesting to note that the phase distribution 36d corresponding to the nearly contrastless image FIG. 34d, does exhibit significant broadening unlike the amplitude distribution, FIG. 35d. This indicates that phase image pixel distribution may be more sensitive to subtle contrast variations than amplitude, The solar conversion efficiency and other parameters of solar cell #2 were obtained using the methods described above, including the maximum power before and after mechanical damage. The I-V characteristics are shown in FIG. 37. The best fits to Equation (11) are excellent for all stages of mechanical damage and the calculated parameters are shown in Table 2. FIG. 38 shows the power curves, FIG. 39 shows the dependence of surface-averaged 10 Hz lock-in carrierographic amplitude on the solar conversation efficiency and it is similar to FIG. 32(a), however, the plots show smaller scatter, thereby better validating the statistical method disclosed above.

TABLE 2

Electrical and LIC statistical parameters of solar cell #2 with mechanical damage

| Solar cell # vs. mechanical damage round | Electrical parameters ($J_i = 20.5$ mW/cm²) | | | | Surface-averaged LIC amplitude | LIC phase |
|---|---|---|---|---|---|---|
| | $J_{sc}$ (mA/cm²) | $J_0$ (nA/cm²) | n | η (%) | $P_M/S$ (mW/cm²) Sum (arb.un./cm²) | Max (degree.) |
| 2-0 | 8.04 | 1.72 | 1.42 | 17.1 | 3.498   27.3 × 10³ | −0.55 |
| 2-1 | 8.12 | 25.2 | 3.32 | 11.4 | 2.333   5.28 × 10³ | 1.5 |
| 2-2 | 8.09 | 52.4 | 3.53 | 10 | 2.048   2.32 × 10³ | 2 |
| 2-3 | 7.81 | 193.4 | 3.73 | 6.64 | 1.361   0.456 × 10³ | — |

LIC Image Pixel Brightness Distribution Dependence on Load Resistance

According to the theoretical expression (63) the closed- and open-circuit photovoltage is expected to have a logarithmic relationship to the surface-integrated LIC image pixel amplitude distribution. One solar cell was irradiated with laser intensity 0.045 W/cm². The statistical distribution peak, FIG. 40, shifted toward decreasing radiative recombination amplitudes with decreasing intensity and photovoltage under smaller load resistance, with a concomitant reduction of the half-width of the distribution.

As with the measurements reported above, it should be mentioned that owing to the surface metallic grid, the local photovoltage can be assumed constant over the surface of the investigated solar cell under small illumination intensity (0.045 W/cm²). The presence of the grid minimizes or eliminates areas of high series resistance and leads to out-diffusion of excess minority carriers from areas with long recombination lifetime (high carrier-wave density) to areas with short lifetime (low density), as well as to shunt resistance (non-radiative recombinations) under open-circuit conditions. As a result, PL from areas with long carrier lifetime significantly decreases and the surface-integrated CG amplitude reflects terminal voltage as well as average transport parameters that determine the generation current across the entire solar cell.

Figure 41:
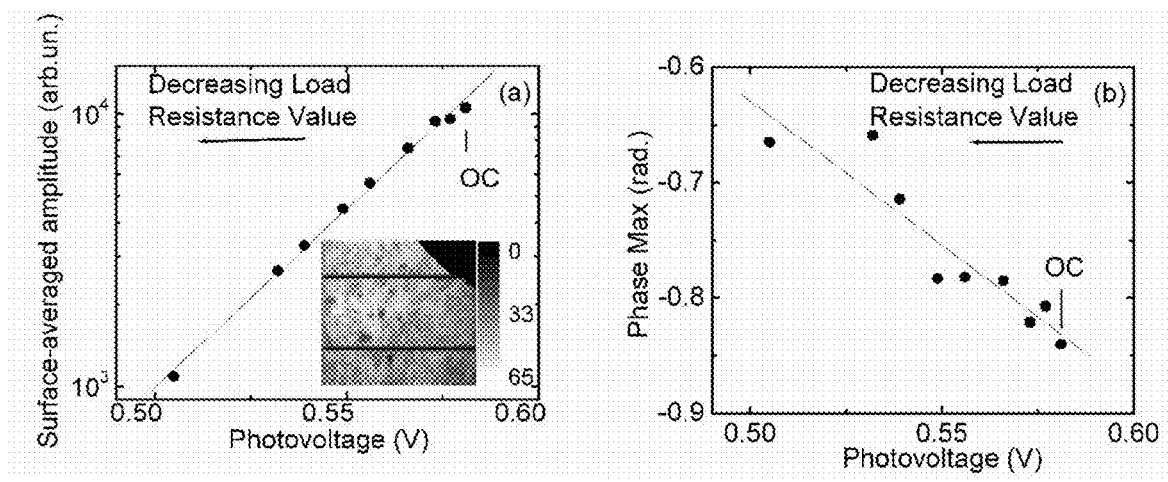
FIG. 41 plots surface-integrated 10-Hz LIC (a) amplitude and (b) phase distribution maximum dependence on terminal photovoltage; laser intensity 0.045 W/cm$^2$; photovoltage was varied as a function of load resistance and was measured at maximum laser power.

FIG. 41 clearly confirms experimentally the theoretical prediction of Equation (60) and its open-circuit special case, Equation (61), written in the form:

$$\langle \ln(CS_{CG}) \rangle = \left\langle \left( \frac{qP_i}{nkT\Delta J} \right) \right\rangle \langle V_{\hbar\omega} \rangle - \left\langle \ln\left( \frac{\Delta J - J}{qF_R(0)} \right) \right\rangle. \quad (83)$$

Example 8

Application of Lock-in Carrierographic Phase Image for Effective Lifetime Mapping of Silicon Wafer Unlike previous qualitative LIC images, in this example, quantitative self-calibrating LIC imaging of wafers is introduced and described. The method is based on the simplified version of the integrated diffuse carrier-wave density presented by Eq.21, in which Eq. 21 is replaced by the rate equation model of Eqn. 64.

With the phase-frequency dependence of all pixels in the carrierographic image fitted to Eq. 66, the effective carrier lifetime map was obtained. The silicon wafer, shown in FIG. 13, was used in this experiment. The experimental setup is shown in FIG. 1($b,c$). The exposure time of the camera was chosen to be 0.52 ms, so the modulation frequency of the laser could reach 400 Hz. A data acquisition module USB 6259 from National Instruments was used to generate a square waveform for laser current modulation, as well as to trigger frame acquisition signals in the camera. The overall measurement and data acquisition time was ca. 3 minutes, corresponding to 100 averages.

Figure 42:
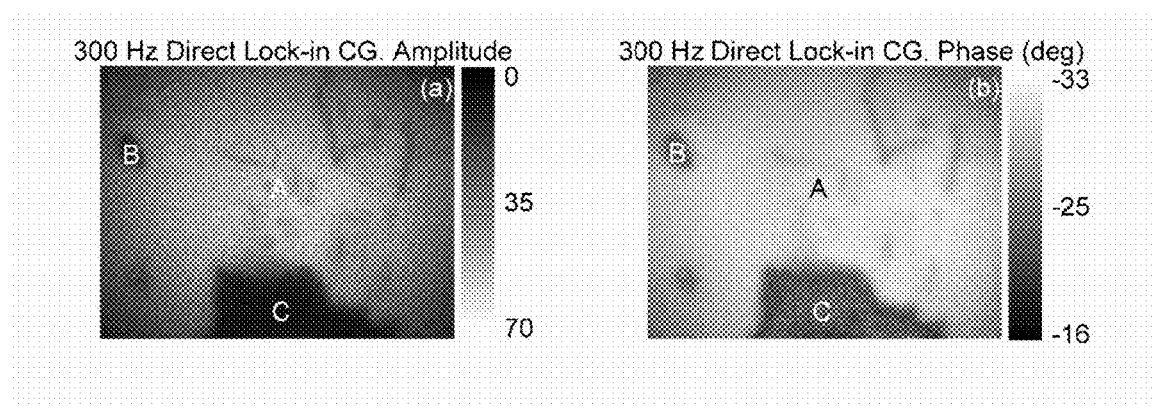
FIG. 42. LIC (a) amplitude and (b) phase images of a Si wafer with mechanical back-side damage. Points A-C were selected for full PCR frequency scans.

The LIC amplitude and phase images of silicon wafer obtained at 300 Hz modulation frequency is shown in FIG. 42. The physical origin of the contrast in the carrierographic images is related to variations in modulated photocarrier-wave density. Qualitative comparison between amplitude and phase images shows the expected correspondence: large amplitude is due to high photocarrier density, i.e. long local effective carrier recombination lifetime and thus large phase lag. The phase lag has a range 20-30 degrees, that in principle allows to use only one frequency phase image for determination of lifetime map.

Figure 43:
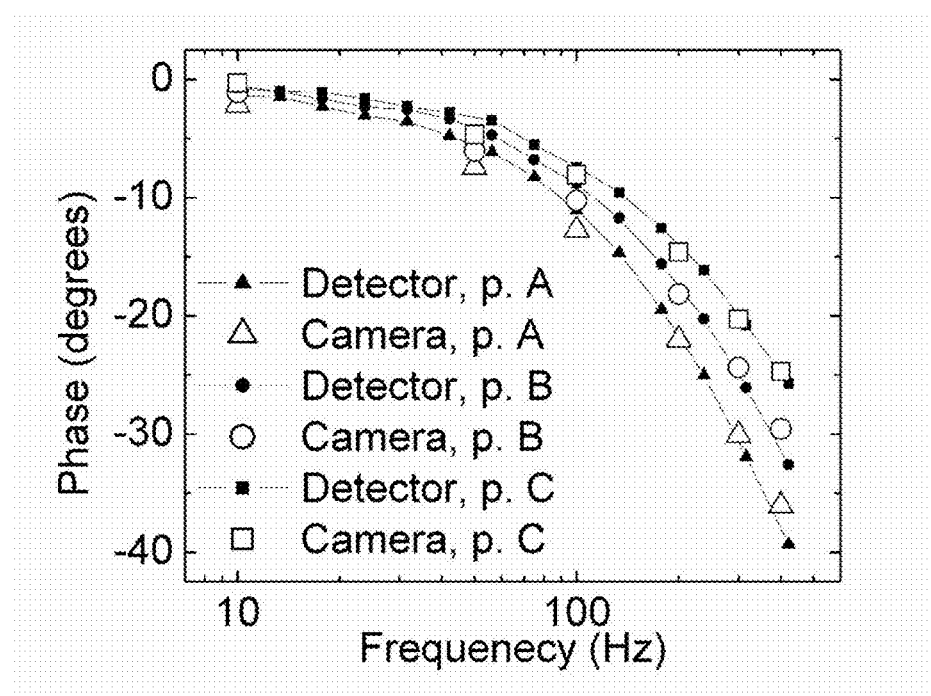
FIG. 43. Comparison of the phase-frequency dependence between camera and single-element InGaAs detector. The modulation frequencies of the camera-based measurement were chosen to be 10 Hz, 50 Hz, 100 Hz, 200 Hz, 300 Hz, and 400 Hz.

To ensure proper quantitative functionality of the LIC system, PCR frequency scans with a single-element InGaAs detector were also carried out. For comparison of our camera results with the single-element detector, PCR frequency scans were also performed from 10 to 400 Hz. FIG. 43 demonstrates the excellent agreement of phase-frequency dependence between the InGaAs camera and single-element detector measurements, which is convincing evidence that quantitatively accurate lifetime images were possible with our camera-based system. Three characteristic locations on the wafer were investigated: Point A at the central intact part and points B and C, located in areas with different degrees of damage.

Figure 44:
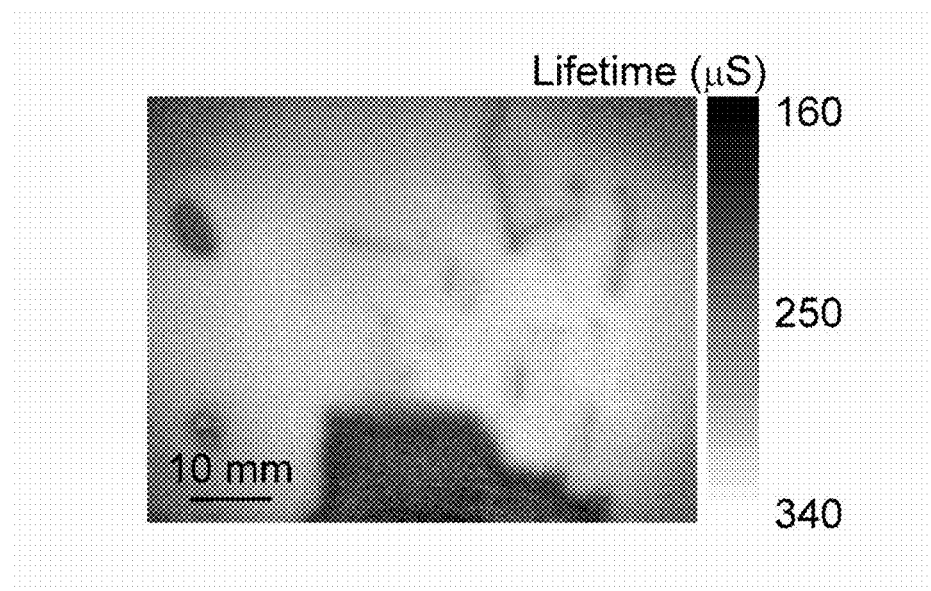
FIG. 44. Lifetime map calculated from the phase-frequency dependence of six carrierographic images.

With the phase-frequency dependence of all pixels in the carrierographic image fitted to Eq. 66, the effective carrier lifetime map was obtained and is shown in FIG. 44. The lifetime map in FIG. 44 shows similar features to the amplitude and phase images of FIG. 42. However, FIG. 44 is a quantitative lifetime image because it is extracted from six phase images at different frequencies including the $\omega\tau_e>1$ range which is sensitive to bulk and surface recombination rates. Therefore, the fitting procedure to Eq. (66) can offset measurement errors and yield high LIC self-consistency, self-calibration and stand-alone reliability.

Example 9

Applications of Lock-in Carrierographic Image Pixel Brightness Dependence on Multi-Crystalline Si Solar Cell Electrical Parameters Obtained at Various External Load Resistances In the present example, additional electrical parameters pertaining to a solar cell may be extracted using the statistical distribution of LIC images. The calculations are based on modification of Eq. 40, resulting in the model described in Eqns. 67-79.

Figure 40:
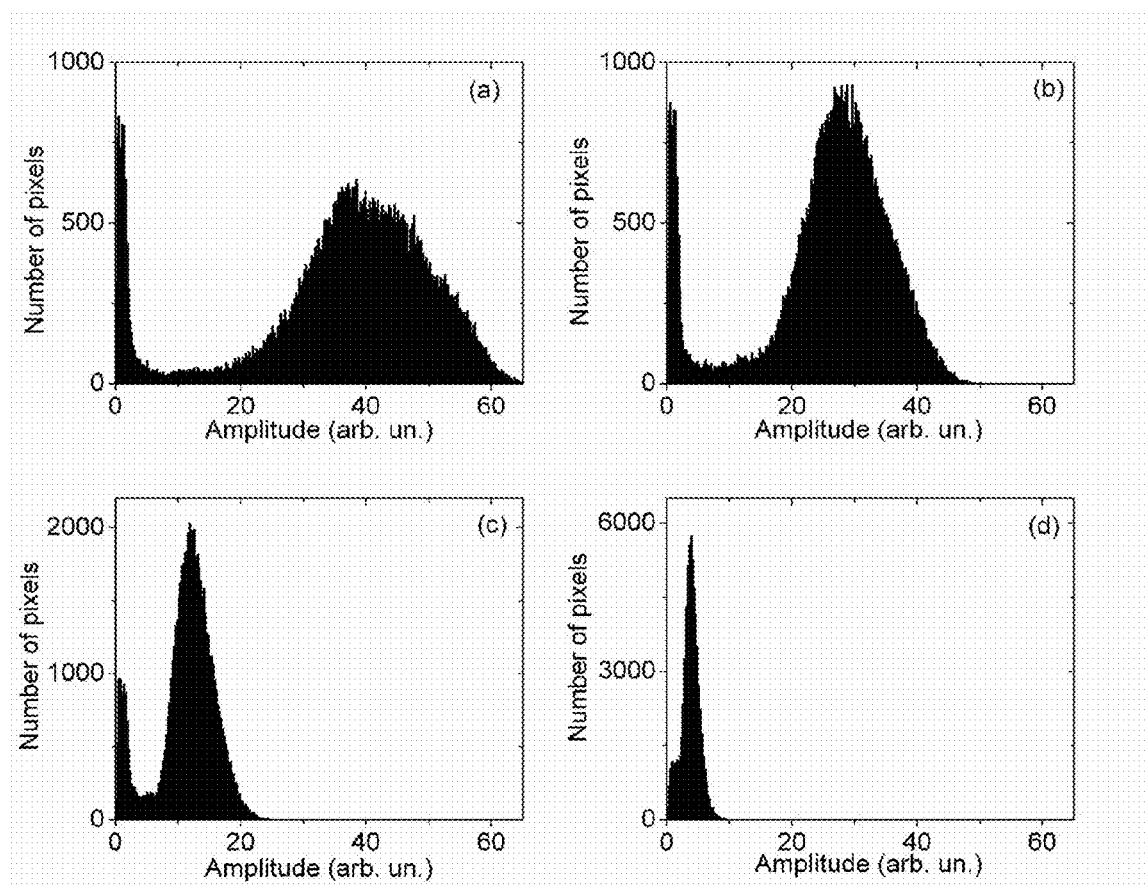
FIG. 40 plots statistical pixel brightness distributions of LIC image amplitudes shown in the inset of FIG. 41 for photovoltage (a) 581 mV, (b) 566 mV, (c) 539 mV, and (d) 505 mV; photovoltage was varied as a function of load resistance and was measured at maximum laser power; Bin size=0.25.

The LIC 10 Hz amplitude images employed in this example were obtained for the various external load resistances under the peak illumination intensity condition of 0.038 W/cm² similar manners as in FIG. 40. The surface-averaged amplitudes representing the radiative recombination emission flux were calculated from the pixel statistics of the images at various external load resistances.

Figure 45:
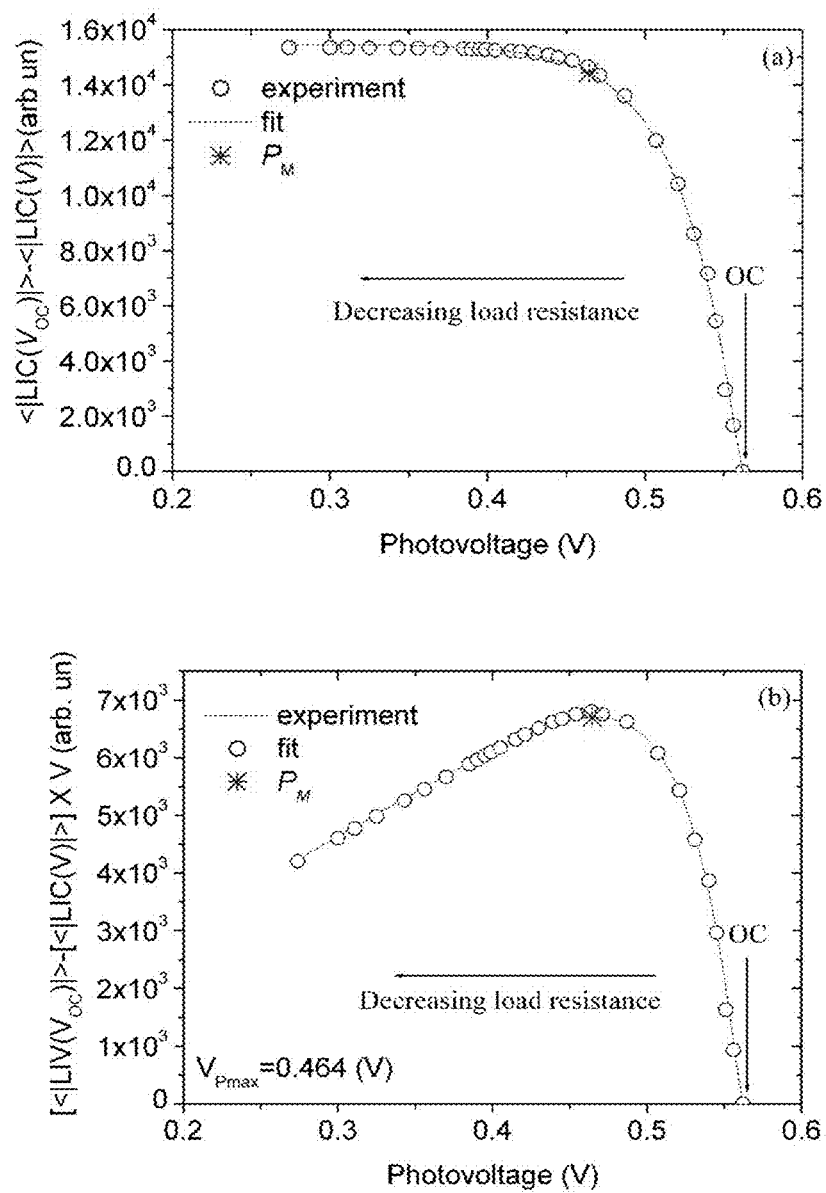
FIG. 45 (a) J[$\hbar\omega$,V($\hbar\omega$),T]$_R$–V characteristics and (b) output power curve. Theoretical fits to Eq. (67). Illumination power density: 0.038 W/cm$^2$, modulation frequency of 10 Hz.

The $J[\hbar\omega, V(\hbar\omega), T]_R$–V characteristics, where $J[\hbar\omega, V(\hbar\omega), T]_R$ is given by Eq. (68), and the best fit to Eq. (67) are shown in FIG. 45($a$). The corresponding power curve is shown in FIG. 45($b$). The parameters ($J_R$, $J_{R0}$ and $n_j$) of the radiative recombination emission process in Eq. (67) were determined from the best fit to the data. Assuming the radiative recombination quantum efficiency to be constant, the $\eta_{ce}(\hbar\omega,0,T)$ was calculated from the definitions of radiative and non-radiative quantum efficiencies by Eq. 35 and from:

$$\eta_{NR}(V_{OC}, T) = \frac{\eta_{ce}(\hbar\omega, 0, T) - \lambda_{in}\lambda_{em}^{-1}}{1 - \lambda_{in}\lambda_{em}^{-1}}, \quad (81)$$

$$\eta_R(V_{OC}, T) = \frac{1 - \eta_{ce}(\hbar\omega, 0, T)}{1 - \lambda_{in}\lambda_{em}^{-1}}.$$

The corresponding electrical parameters of the solar cell $J_g$, $J_0$, n, $V_{OC}$, FF were obtained according to Eqs. (75-79) using the best-fitted parameters to Eq. (67) and LIC images. They are listed in Table 3 and they are seen to be in very good agreement with those obtained from the electrical measurements.

TABLE 3

Electrical parameters obtained by electrical and LIC methods

| | $I_i = 0.038$ W/cm² | |
|---|---|---|
| | Method | |
| Parameters | E M | LIC |
| $J_g$ (mA/cm²) | 17.4 | 17.3 |
| $J_0$ (µA/cm²) | 0.117 | 0.124 |
| Ideality factor n, | 1.742 | 1.772 |
| Shunt resistance (Ω) | 1000 | — |
| $P_{max}$ voltage (V) | 0.460 | 0.464 |
| Open-circuit Voltage ($V_{OC}$) | 0.562 | 0.564 |
| Fill factor FF | 0.7224 | 0.7211 |
| Solar conversion efficiency $\eta_e$ % | 18.6 | 18.7 |
| $R^2$ (denotes best fit to Eqs used) | 0.997 | 0.998 |

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

[1] T. Fuyuki, H. Kondo, T. Yamazaki, Y. Takahashi, and Y. Uraoka, Appl. Phys. Lett. 86, 262108 (2005)
[2] P. Würfel, T. Trupke, T. Puzzer, E. Schäffer, W. Warta, S. W. Glunz, J. Appl. Phys. 101, 123110 (2007).
[3] J. A. Gisecke, M. Kasemann, W. Warta. J. Appl. Phys. 106, 014907 (2009).
[4a] D. Guidotti, J. S. Batchelder, J. A. Van Vechten, and A. Finkel, Appl. Phys. Lett. 48, 68 (1986)
[4b] S. Herlufsen, K. Ramspeck, D. Hinken, A. Schmidt, J. Müller, K. Bothe, J. Schmidt, and R. Brendel, Phys. Stat. Sol. RRL 1, (2010)
[5] A. Mandelis, J. Batista and D. Shaughnessy, Phys. Rev. B, 67 205208 (2003).
[6] A. Melnikov, A. Mandelis, J. Tolev, P. Chen, and S. Huq, J. Appl. Phys. 107, 114513 (2010).
[7] A. Mandelis, "Diffusion-Wave Fields: Mathematical Methods and Green Functions", Springer, New York (2001), Chap. 9.
[8] T. Ikari T, A. Salnick and A. Mandelis, J. Appl. Phys. 85, 7392 (1999).
[9] O. Breitenstein, W. Warta, M. Langenkamp, Lock-in Thermography, Springer Series in Advanced Microelectronics (Springer, New York, $2^{nd}$ Ed.) 2010, 255 p.
[10] S. Grauby, B. C. Forget, S. Hole and D. Fournier, Rev. Sci. Instrum. 70, 3603 (1999).
[11] S. Grauby, S. Dilhaire, S. Jorez and W. Claeys, Rev. Sci. Instrum. 74, 645 (2003).
[12] A. Mandelis, A. Melnikov, J. Tolev, J. Xia, S. Haq, and E. Lioudakis, Quant. Infra Red Thermogr. (QIRT) J. 7, 35 (2010).
[13] J. Tolev, A. Mandelis, and M. Pawlak, J. Electrochem. Soc. 154, H938 (2007)
[14] A. Mandelis. JAP, 66, 5572 (1989)
[14a] S.-Y. Zhang and J.-C. Cheng, Semicond. Sci. Technol. 6, 670 (1991)
[15] I. Latchford and J. B. True, in "Photovoltaics World", Issue 4, July/August 2011.
[16] M. Bail, M. Schulz and R. Brendel, Appl. Phys. Lett. 82, 757 (2003).
[17] J. Schmidt and A. G. Aberle, J. Appl. Phys. 81, (1997) 6186.
[18] T. Trupke, R. A. Bardos, M. C. Schubert and W. Warta, Appl. Phys. Lett. 89, 044107 (2006).
[19] M. The, M. C. Schubert, W. Warta, Proc. $22^{nd}$ EUPVSEC, 354 (2007).
[20] D. Macdonald, J. Tan and T. Trupke, J. Appl. Phys. 103, 073710 (2008).
[21] W. Shockley and H. J. Queisser, J. Appl. Phys. 32, 510 (1961)
[22] A. Mandelis, Solid-State Electron. 42, 1 (1998).
[23] J. Isenberg and W. Warta, Progr. Photovoltaics: Research and Applications 12, 339 (2004).
[24] O. Breitenstein M. Langenkamp, O. Lang and A. Schirrmacher, Solar Energy Mater. Solar Cells 65, 55 (2001).
[25] M. Kasemann, M. C. Schubert, M. The, M. Kober, M. Hermle, and W. Warta, Appl. Phys. Lett. 89, 224102 (2006).
[26] J. Batista, A. Mandelis and D. Shaughnessy, Appl. Phys. Lett. 82, 4077 (2003).
[27] A. Melnikov, A. Mandelis, J. Tolev, and E. Lioudakis. J. Phys. Conference Series 214, 012111 (2010).
[28] P. Würfel, J. Phys. C 15, 3967 (1982).
[29] P. Würfel, S. Finkbeiner, and E. Daub, Appl. Phys. A 60, 67 (1995).
[30] A. L. Fahrenbruch and R. H. Bube, "Fundamentals of Solar Cells", Academic, New York (1983).
[31] A. K. Ghosh, C. Fishman, and J. Teng, J. Appl. Phys. 51, 446 (1980).
[32] T. Trupke, R. A. Bardos, M. D. Abbott, J. E. Gotter, Appl. Phys. Lett. 87, 093503 (2005).
[33] D. Guidotti, J. S. Batchelder, A. Finkel, P. D. Gerber, and J. A. Van Vechten, J. Appl. Phys. 66, 2542 (1989).
[34] J. S. Blakemore, "Semiconductor Statistics", Dover, Mineola N.Y., (1987), Chap. 5.
[35] S. M. Sze, "Physics of semiconductor devices", $2^{nd}$ Ed., Wiley, New York (1981); chap. 14.
[36] D. K. Schroder, IEEE Trans. Electron Dev. 44, 160 (1997).

Therefore what is claimed is:

1. A method of producing an optical carrierographic image of a semiconductor sample, the method comprising:
    a) generating a first modulation signal having a first modulation frequency and a second modulation signal having a second modulation frequency, wherein a beat frequency between the first modulation frequency and the second modulation frequency is substantially less than both the first modulation frequency and the second modulation frequency;
    b) generating a reference signal having a reference frequency equal to the beat frequency;
    c) providing a first optical beam and a second optical beam, the first optical beam and the second optical beam having wavelengths selected for excitation of carriers within the semiconductor sample;
    d) focusing and spatially overlapping the first optical beam and the second optical beam onto a location of the semiconductor sample;
    e) modulating the first optical beam according to the first modulation signal and modulating the second optical beam according to the second modulation signal;
    f) detecting, with an infrared detector, infrared radiation emitted from the semiconductor sample in response to absorption of the first optical beam and the second optical beam, and obtaining a plurality of carrierographic signals at different points in time during at least one beat period; and
    g) providing the reference signal to a lock-in amplifier and processing the carrierographic signals with the lock-in amplifier to obtain an amplitude signal and a phase signal.

2. The method according to claim 1 further comprising the step of synchronizing the first modulation signal, the second modulation signal, and the reference signal prior to the step of obtaining the carrierographic signals.

3. The method according to claim 1 wherein the first optical beam and the second optical beam are focused onto the semiconductor sample.

4. The method according to claim 3 further comprising the step of repeating steps d) to g) for one or more additional locations of the semiconductor sample.

5. The method according to claim 4 wherein the first optical beam and the second optical beam are scanned over an area of the semiconductor sample, the method further comprising the step of forming an amplitude image and a phase image of the area based on the amplitude signals and the phase signals obtained while scanning the first optical beam and the second optical beam.

6. The method according to claim 1 wherein the infrared detector is an infrared camera, and wherein steps f) and g) include:
  detecting, with the infrared camera, infrared radiation emitted from the semiconductor sample in response to absorption of the first optical beam and the second optical beam, and obtaining a plurality of carrierographic signal frames at different points in time during at least one beat period, wherein an exposure time of the infrared camera exceeds the inverse of the first modulation frequency and the inverse of the second modulation frequency, and wherein a frame rate of the infrared camera exceeds the beat frequency;
  providing the reference signal to a lock-in amplifier and processing the carrierographic signal frames with the lock-in amplifier to obtain carrierographic images including an amplitude image and a phase image.

7. The method according to claim 6 wherein said lock-in amplifier is configured for parallel lock-in detection over all camera pixels using in-phase and quadrature operations.

8. The method according to claim 6 wherein a maximal value of the exposure time of the infrared camera is selected.

9. The method according to claim 6 wherein an optical power of the first optical beam and an optical power of the second optical beam are sufficiently low to avoid substantial optical flooding of the semiconductor sample.

10. The method according to claim 6 wherein the infrared camera is an InGaAs camera.

11. The method according to claim 6 further comprising the step processing one or both of the amplitude image and the phase image to determine one or more properties of the semiconductor sample.

12. The method according to claim 11 wherein the one or more properties are obtained by comparing one or both of the amplitude image and the phase image, or comparing a measure based one or both of the amplitude image and phase image, with previously measured calibration data.

13. The method according to claim 11 wherein the step of processing one or both of the amplitude image and the phase image includes obtaining one or more statistical measures of the semiconductor sample based on a statistical analysis of image pixel values.

14. The method according to claim 11 wherein the step of processing one or both of the amplitude image and the phase image includes inferring a spatially dependent carrier lifetime from one or both of the amplitude image and the phase image.

15. The method according to claim 11 wherein the step of processing one or both of the amplitude image and the phase image includes determining diffusion coefficient, surface recombination velocity, defects, series resistance, shunt resistance, quality of p-n junction, photoluminescence nonlinearity.

16. The method according to claim 11 wherein the semiconductor sample is a solar cell, and wherein the step of processing one or both of the amplitude image and the phase image includes calculating a surface averaged amplitude from the amplitude image and determining a solar cell efficiency based on calibration data relating the solar cell efficiency to the surface averaged amplitude.

17. The method according to claim 11 wherein the semiconductor sample is a solar cell, and wherein the step of processing one or both of the amplitude image and the phase image includes calculating a maximum phase from the phase image and determining a solar cell efficiency based on calibration data relating the solar cell efficiency to the maximum phase.

18. The method according to claim 1 wherein the first modulation frequency and the second modulation frequency exceed approximately 10 kHz.

19. The method according to claim 1 wherein the first modulation frequency and the second modulation frequency lie between approximately 10 kHz and 50 kHz.

20. The method according to claim 1 wherein the first modulation frequency and the second modulation frequency exceed approximately 50 kHz.

21. The method according to claim 1 wherein the beat frequency is less than 1 kHz.

22. The method according to claim 1 wherein the first optical beam and the second optical beam are provided by super bandgap lasers.

23. The method according to claim 1 wherein the first modulation frequency and the second modulation frequency are selected such the carrierographic images are sensitive to a recombination lifetime limiting one or more of defect-state densities and trap-state densities.

24. The method according to claim 1 wherein the first optical beam and the second optical beam have approximately equal average wavelengths.

25. The method according to claim 1 further comprising the step of filtering radiation incident on the infrared detector to avoid the detection of scattered light from one or more of the first optical beam and the second optical beam.

26. The method according to claim 1 wherein the first optical beam and the second optical beam are configured generate nonlinear carrierographic images.

27. The method according to claim 1 wherein the first optical beam and the second optical beam absorbed without acting as external local oscillator.

28. The method according to claim 1 wherein the semiconductor sample is a semiconductor substrate.

29. The method according to claim 1 wherein the semiconductor sample comprises silicon.

30. The method according to claim 1 wherein the semiconductor sample is a semiconductor device.

31. The method according to claim 30 wherein the semiconductor device is a solar cell.

32. A method of measuring the effective lifetime of carriers in a semiconductor substrate using lock-in-carrierography, the method comprising:
  measuring lock-in-carrierography images of the semiconductor substrate at a plurality of modulation frequencies, each lock-in-carrierography image comprising a plurality of lock-in-carrierography signals corresponding to different locations of the substrate, where the lock-in-carrierography images are measured according to the method of claim 1;
  fitting a frequency dependence of the lock-in-carrierography signals from the lock-in-carrierography images to a rate equation model having the effective lifetime as a parameter; and
  calculating the effective lifetime at a plurality of locations of the semiconductor substrate.

33. The method according to claim 32 further comprising generating a lifetime map of the substrate based on the calculated effective lifetimes.

34. The method according to claim 32 wherein rate equation model is of the form:

$$S(\omega) = \tau\_e * K / (1 + i * \omega * \tau\_e)$$

where S(omega) is the lock-in-carrierography signal, tau is the effective lifetime, omega is the modulation frequency, and K is a constant.

35. The method according to claim 32 wherein the fitting of the lock-in-carrierography image to the rate equation model is performed based on the phase of the lock-in-carrierography image.

36. The method according to claim 32 wherein the fitting of the lock-in-carrierography image to the rate equation model is performed based on the amplitude of the lock-in-carrierography image.

37. A method of optically measuring one or more electrical parameters of a solar cell using lock-in-carrierography, the method comprising:

determining a mathematical relationship between a lock-in-carrierographic signal and one or more electrical properties of the solar cell, the mathematical relationship involving a calibration factor relating the lock-in-carrierographic signal to an electrical model of the solar cell;

measuring a plurality of lock-in-carrierography images of the solar cell, where the lock-in-carrierography images are measured according to the method of claim 1;

calculating average signals from the lock-in-carrierography images; and determining the one or more electrical parameters by fitting the mathematical relationship to the average signals.

38. The method according to claim 37 wherein the plurality of lock-in-carrierography images are measured at different load resistances.

39. The method according to claim 37 wherein the plurality of lock-in-carrierography images are measured for different optical intensities in a non-contacting configuration.

40. The method according to claim 37 wherein the one or more electrical parameters are selected from the group consisting of $J_g$, $J_0$, the ideality factor n, shunt resistance, $P_{max}$ voltage, open-circuit voltage, fill factor, and solar conversion efficiency $\eta_e$.

\* \* \* \* \*